US012780894B2

(12) United States Patent
Tykocinski et al.

(10) Patent No.: US 12,780,894 B2
(45) **Date of Patent: *Nov. 3, 2026**

(54) PD1-41BBL FUSION PROTEIN AND METHODS OF USE THEREOF

(71) Applicant: KAHR Medical Ltd., Modiln Makabim-ReUt (IL)

(72) Inventors: Mark L. Tykocinski, Merion Station, PA (US); Noam Shani, Zikhron-Yaakov (IL); Yosi Gozlan, Rehovot (IL); Michal Dranitzki Elhalel, Shoresh (IL); Edwin Bremer, Groningen (NL); Ido Kaminsky, Ramat-Gan (IL)

(73) Assignee: KAHR Medical Ltd., Modiln Makabim-ReUt (IL)

( * ) Notice: Subject to any disclaimer, the term of this patent is extended or adjusted under 35 U.S.C. 154(b) by 628 days.

This patent is subject to a terminal disclaimer.

(21) Appl. No.: 18/212,218

(22) Filed: Jun. 21, 2023

(65) Prior Publication Data

US 2024/0010700 A1 Jan. 11, 2024

Related U.S. Application Data

(63) Continuation of application No. 16/475,705, filed as application No. PCT/IL2018/050015 on Jan. 4, 2018, now Pat. No. 11,702,458.

(60) Provisional application No. 62/442,471, filed on Jan. 5, 2017.

(51) Int. Cl.

| | |
|---|---|
| ***C07K 14/705*** | (2006.01) |
| ***A61K 38/17*** | (2006.01) |
| ***A61K 39/395*** | (2006.01) |
| ***A61P 35/00*** | (2006.01) |
| ***C07K 16/24*** | (2006.01) |
| ***C07K 16/28*** | (2006.01) |

(52) U.S. Cl.

CPC .. *C07K 14/70503* (2013.01); *C07K 14/70575* (2013.01); *C07K 16/241* (2013.01); *C07K 16/2827* (2013.01); *C07K 2319/21* (2013.01)

(58) Field of Classification Search

None

See application file for complete search history.

(56) References Cited

U.S. PATENT DOCUMENTS 5,287,386 A 2/1994 Wade et al.
5,674,704 A 10/1997 Goodwin et al.
6,046,048 A 4/2000 Ashkenazi et al.
6,740,739 B1 5/2004 Ashkenazi
7,142,018 B2 11/2006 Masleid et al.
7,279,925 B1 10/2007 Richmond et al.
7,569,663 B2 8/2009 Tykocinski et al.
8,039,437 B2 10/2011 Tykocinski et al.
8,216,805 B2 7/2012 Carter et al.
9,562,087 B2 2/2017 Ring et al.
10,040,841 B2 8/2018 Dranitzki Elhalel
10,183,060 B2 1/2019 Schreiber et al.
10,392,445 B2 8/2019 Amann
10,464,981 B2 11/2019 Amann et al.
11,130,796 B2 9/2021 Shani et al.
11,702,458 B2 * 7/2023 Tykocinski ........ C07K 16/2827 424/178.1
11,897,937 B2 2/2024 Shani
12,134,638 B2 11/2024 Pecker et al.
12,286,466 B2 * 4/2025 Pecker ............ C07K 14/70575
2003/0216546 A1 11/2003 Tykocinski et al.
2007/0036783 A1 2/2007 Humeau et al.
2007/0110746 A1 5/2007 Chung
2012/0189625 A1 7/2012 Wang et al.
2013/0039911 A1 2/2013 Bedi et al.
2013/0094307 A1 4/2013 Cheng
2013/0287802 A1 10/2013 Govindappa et al.
2015/0183881 A1 7/2015 Bedi et al.
2015/0353642 A1 12/2015 Tykocinski
2015/0376260 A1 12/2015 Elhalel et al.
2016/0039903 A1 2/2016 Ring et al.
2016/0200833 A1 7/2016 Amann et al.
2017/0095531 A1 4/2017 Schreiber et al.
2017/0107270 A1 4/2017 Pons et al.
2017/0274003 A1 9/2017 Shatz et al.

(Continued)

FOREIGN PATENT DOCUMENTS

CN 104968364 10/2015
CN 107001485 8/2017

(Continued)

OTHER PUBLICATIONS

Supplementary European Search Report and the European Search Opinion Dated Dec. 23, 2024 From the European Patent Offie Re. Application No. 22739265.1. (13 Pages).
Office Action Dated Aug. 7, 2023 From the Israel Patent Office Re. Application No. 267862. (3 Pages).
Examination Report Dated May 5, 2025 From the Australian Government, IP Australia Re. Application No. 2019301316. (5 Pages).
Request for Examination and Search Report Dated Apr. 17, 2025 From the (Rospatent), The Federal Service for Intellectual Property, Patents and Trademarks of the Russian Federation Re. Application No. 2023120654 and Its Machine Translation of Office Action Into English. (17 Pages).
International Preliminary Report on Patentability Dated Jul. 4, 2024 From the International Bureau of WIPO Re. Application No. PCT/IL2022/051378. (7 Pages).

(Continued)

*Primary Examiner* — Ilia I Ouspenski

(57) ABSTRACT

PD1-41BBL fusion proteins are provided. Accordingly, there is provided a PD1-41BBL fusion protein comprising a single amino acid linker between the PD1 and the 41BBL. Also there is provided a PD1-41BBL fusion protein, wherein the PD1 amino acid is 123-166 amino acids in length and/or wherein the PD1 amino acid sequence comprises SEQ ID NO: 2 and/or wherein the fusion protein is in a form of at least a homo-trimer. Also provided are polynucleotides and nucleic acid constructs encoding the PD1-41BBL fusion protein, host-cells expressing the PD1-41BBL fusion protein and methods of use thereof.

7 Claims, 11 Drawing Sheets

Specification includes a Sequence Listing.

(56) References Cited

U.S. PATENT DOCUMENTS

| | | | |
|---|---|---|---|
| 2017/0327588 | A1 | 11/2017 | Baca |
| 2019/0016782 | A1 | 1/2019 | Dranitzki Elhalel et al. |
| 2019/0151413 | A1 | 5/2019 | Schreiber |
| 2019/0315834 | A1 | 10/2019 | Shani et al. |
| 2019/0330304 | A1 | 10/2019 | Shani et al. |
| 2019/0352371 | A1 | 11/2019 | Tykocinski et al. |
| 2019/0352372 | A1 | 11/2019 | Shani et al. |
| 2020/0087377 | A1 | 3/2020 | Yue et al. |
| 2020/0216505 | A1 | 7/2020 | Schreiber et al. |
| 2020/0317773 | A1 | 10/2020 | Clark et al. |
| 2021/0214417 | A1 | 7/2021 | Pecker et al. |
| 2021/0284711 | A1 | 9/2021 | Pecker et al. |
| 2021/0301020 | A1 | 9/2021 | Yu et al. |
| 2021/0371500 | A1 | 12/2021 | Shani et al. |
| 2022/0204586 | A1 | 6/2022 | Shani et al. |
| 2022/0267409 | A1 | 8/2022 | Tykocinski et al. |
| 2023/0048361 | A1* | 2/2023 | Muthuswamy ...... C12N 5/0636 |
| 2023/0048719 | A1* | 2/2023 | Muthuswamy ......... A61P 35/00 |
| 2023/0220040 | A1 | 7/2023 | Shani et al. |
| 2024/0109952 | A1 | 4/2024 | Shani |

FOREIGN PATENT DOCUMENTS

| | | |
|---|---|---|
| CN | 107857819 | 3/2018 |
| CN | 108350055 | 7/2018 |
| CN | 110128550 | 8/2019 |
| JP | 2013-521311 | 6/2013 |
| JP | 2017-060462 | 3/2017 |
| JP | 2017-525354 | 9/2017 |
| JP | 2021-500829 | 1/2021 |
| JP | 2021-531265 | 11/2021 |
| JP | 7491495 | 5/2024 |
| KR | 10-2017-0017846 | 2/2017 |
| RU | 2636342 | 11/2017 |
| RU | 2736616 | 11/2020 |
| WO | WO 01/049318 | 7/2001 |
| WO | WO 01/75067 | 10/2001 |
| WO | WO 01/86003 | 11/2001 |
| WO | WO 03/046581 | 6/2003 |
| WO | WO 2005/087797 | 9/2005 |
| WO | WO 2010/027828 | 3/2010 |
| WO | WO 2010/070047 | 6/2010 |
| WO | WO 2010/130053 | 11/2010 |
| WO | WO 2011/109789 | 9/2011 |
| WO | WO 2012/042480 | 4/2012 |
| WO | WO 2013/064700 | 5/2013 |
| WO | WO 2013/109752 | 7/2013 |
| WO | WO 2013/112986 | 8/2013 |
| WO | WO 2013/144704 | 10/2013 |
| WO | WO 2014/072534 | 5/2014 |
| WO | WO 2014/106839 | 7/2014 |
| WO | WO 2014/121093 | 8/2014 |
| WO | WO 2014/164519 | 10/2014 |
| WO | WO 2014/180288 | 11/2014 |
| WO | WO 2015/148416 | 10/2015 |
| WO | WO 2015/179633 | 11/2015 |
| WO | WO 2016/022994 | 2/2016 |
| WO | WO 2016/023001 | 2/2016 |
| WO | WO 2016/023040 | 2/2016 |
| WO | WO 2016/024021 | 2/2016 |
| WO | WO 2016/063233 | 4/2016 |
| WO | WO 2016/065329 | 4/2016 |
| WO | WO 2016/075278 | 5/2016 |
| WO | WO 2016/090312 | 6/2016 |
| WO | WO 2016/139668 | 9/2016 |
| WO | WO 2016/169261 | 10/2016 |
| WO | WO 2016/187226 | 11/2016 |
| WO | WO 2017/012770 | 1/2017 |
| WO | WO 2017/019846 | 2/2017 |
| WO | WO 2017/027422 | 2/2017 |
| WO | WO 2017/059168 | 4/2017 |
| WO | WO 2017/068192 | 4/2017 |
| WO | WO 2017/152132 | 9/2017 |
| WO | WO 2017/181119 | 10/2017 |
| WO | WO 2017/194641 | 11/2017 |
| WO | WO 2017/207775 | 12/2017 |
| WO | WO 2018/006881 | 1/2018 |
| WO | WO 2018/032793 | 2/2018 |
| WO | WO 2018/053885 | 3/2018 |
| WO | WO 2018/085358 | 5/2018 |
| WO | WO 2018/091580 | 5/2018 |
| WO | WO 2018/114754 | 6/2018 |
| WO | WO 2018/127916 | 7/2018 |
| WO | WO 2018/127916 A9 | 7/2018 |
| WO | WO 2018/127917 | 7/2018 |
| WO | WO 2018/127918 | 7/2018 |
| WO | WO 2018/127918 A9 | 7/2018 |
| WO | WO 2018/127919 | 7/2018 |
| WO | WO 2018/127919 A9 | 7/2018 |
| WO | WO 2019/086499 | 5/2019 |
| WO | WO 2020/012485 | 1/2020 |
| WO | WO 2020/012486 | 1/2020 |
| WO | WO 2020/012485 A9 | 5/2020 |
| WO | WO 2020/146423 | 7/2020 |
| WO | WO 2020/242919 | 12/2020 |
| WO | WO 2021/005599 | 1/2021 |
| WO | WO 2022/153307 | 7/2022 |
| WO | WO 2023/119295 | 6/2023 |

OTHER PUBLICATIONS

Official Action Dated Sep. 5, 2024 from the US Patent and Trademark Office Re. U.S. Appl. No. 18/537,886. (84 pages).

Falk et al. "Bevacizumab: A Dose Review", Critical Reviews in Oncology/Hematology, 94(3): 311-322, Jun. 2015.

Requisition by the Examiner Dated Oct. 22, 2024 From the Innovation, Science and Economic Development Canada, Canadian Intellectual Property Office Re. Application No. 3,104,780. (5 Pages).

Requisition by the Examiner Dated Mar. 18, 2025 From the Innovation, Science and Economic Development Canada, Canadian Intellectual Property Office Re. Application No. 3,104,778. (5 Pages).

Restriction Official Action Dated Mar. 14, 2025 from the US Patent and Trademark Office Re. U.S. Appl. No. 17/626,185. (10 Pages).

Appeal Against Decision of Refusal Dated Nov. 19, 2024 From the Japan Patent Office Re. Application No. 2019-536286. (2 Pages).

Office Action Dated Nov. 11, 2024 From the Israel Patent Office Re. Application No. 280102. (3 Pages).

Office Action Dated Nov. 26, 2024 From the Israel Patent Office Re. Application No. 280103. (5 Pages).

Requisition by the Examiner Dated Sep. 26, 2024 From the Innovation, Science and Economic Development Canada, Canadian Intellectual Property Office Re. Application No. 3,146,248. (6 pages).

Requisition by the Examiner Dated Oct. 8, 2025 From the Innovation, Science and Economic Development Canada, Canadian Intellectual Property Office Re. Application No. 3,104,780. (3 Pages).

Written Opinion Dated Jan. 8, 2024 From the Intellectual Property Office of Singapore, IPOS Re. Application No. 11202013167U. (8 Pages).

English summary dated Jul. 3, 2023 of Request for Examination Dated Jun. 7, 2023 From the Federal Government Institution, Federal Institute of Industrial Property of the Federal Service of Intellectual Property, Patents and Trademarks of the Russian Federation, FIPS Re. Application No. 2021101091.

Notice of Reason(s) for Rejection Dated Jun. 27, 2023 From the Japan Patent Office Re. Application No. 2021-500820. (3 pages).

Restriction Official Action Dated Jun. 29, 2023 from the US Patent and Trademark Office Re. U.S. Appl. No. 17/258,220. (13 pages).

Communication Pursuant to Article 94(3) EPC Dated Jun. 1, 2017 From the European Patent Office Re. Application No. 13827047.5. (4 Pages).

Communication Pursuant to Article 94(3) EPC Dated Oct. 1, 2021 From the European Patent Office Re. Application No. 18736642.2. (7 Pages).

Communication Pursuant to Article 94(3) EPC Dated Feb. 6, 2018 From the European Patent Office Re. Application No. 13827047.5. (5 Pages).

(56) References Cited

OTHER PUBLICATIONS

Communication Pursuant to Article 94(3) EPC Dated May 9, 2022 From the European Patent Office Re. Application No. 18736642.2. (8 Pages).
Communication Pursuant to Article 94(3) EPC Dated Sep. 26, 2016 From the European Patent Office Rc. Application No. 13827047.5. (3 Pages).
English Summary Dated May 11, 2023 of Notification of Office Action Dated Apr. 27, 2023 From the State Intellectual Property Office of the People's Republic of China Re. Application No. 201880016069.X (3 pages).
English Summary Dated Jun. 16, 2023 of Notification of Office Action Dated Jun. 1, 2023 From the State Intellectual Property Office of the People's Republic of China Re. Application No. 201980052864.9. (3 pages).
English Summary Dated Jun. 19, 2023 of Notification of Office Action and Search Report Dated Jun. 2, 2023 From the State Intellectual Property Office of the People's Republic of China Re. Application No. 201980052845.6. (3 pages).
English Translation Dated May 9, 2022 of Notice of Reasons for Rejection Dated Apr. 26, 2022 From the Japan Patent Office Re. Application No. 2019-536308. (4 Pages).
Examination Report Dated Jul. 11, 2017 From the Australian Government, IP Australia Re. Application No. 2013371826.(4 Pages).
Examination Report Dated Feb. 25, 2022 From the Intellectual Property Office of Singapore, IPOS Re. Application No. 11201905679S. (6 pages).
Examination Report Dated Mar. 28, 2018 From the Australian Government, IP Australia Re. Application No. 2013371826.(2 Pages).
Examination Report Under Sections 12 & 13 of the Patents Act, 1970 and the Patents Rules, 2003 Dated Jul. 18, 2022 From the Government of India, Intellectual Property India, Patents Designs, Trade Marks, Geographical Indications The Patent Office Re. Application No. 202127002771. (6 Pages).
Final Official Action Dated May 12, 2021 From the US Patent and Trademark Office Re. U.S. Appl. No. 16/027,382. (15 Pages).
Final Official Action Dated Dec. 14, 2022 from the US Patent and Trademark Office Re. U.S. Appl. No. 17/258,170. (55 pages).
Grounds of Reason of Rejection Dated Apr. 5, 2023 From the Korean Intellectual Property Office Re. Application No. 10-2019-7022855. (4 Pages).
Grounds of Reason of Rejection Dated Mar. 7, 2023 From the Korean Intellectual Property Office Re. Application No. 10-2019-7022848 (6 Pages).
International Preliminary Report on Patentability Dated Jul. 16, 2015 From the International Bureau of WIPO Re. Application No. PCT/IL2013/051098. (14 Pages).
International Preliminary Report on Patentability Dated Jul. 18, 2019 From the International Bureau of WIPO Re. Application No. PCT/IL2018/050014. (7 Pages).
International Preliminary Report on Patentability Dated Jul. 18, 2019 From the International Bureau of WIPO Re. Application No. PCT/IL2018/050015. (7 Pages).
International Preliminary Report on Patentability Dated Jul. 18, 2019 From the International Bureau of WIPO Re. Application No. PCT/IL2018/050016. (7 Pages).
International Preliminary Report on Patentability Dated Jul. 18, 2019 From the International Bureau of WIPO Re. Application No. PCT/IL2018/050017. (7 Pages).
International Preliminary Report on Patentability Dated Jan. 20, 2022 From the International Bureau of WIPO Re. Application No. PCT/IL2020/050762. (8 Pages).
International Preliminary Report on Patentability Dated Jan. 21, 2021 From the International Bureau of WIPO Rc. Application No. PCT/IL2019/050782. (9 Pages).
International Preliminary Report on Patentability Dated Jan. 21, 2021 From the International Bureau of WIPO Re. Application No. PCT/IL2019/050783. (8 Pages).
International Search Report and the Written Opinion Dated Oct. 6, 2020 From the International Searching Authority Re. Application No. PCT/IL2020/050762. (13 Pages).
International Search Report and the Written Opinion Dated May 9, 2022 From the International Searching Authority Re. Application No. PCT/IL2022/050055. (19 Pages).
International Search Report and the Written Opinion Dated Mar. 13, 2018 From the International Searching Authority Re. Application No. PCT/IL2018/050015. (11 Pages).
International Search Report and the Written Opinion Dated Mar. 13, 2018 From the International Searching Authority Re. Application No. PCT/IL2018/050016. (11 Pages).
International Search Report and the Written Opinion Dated May 15, 2014 From the International Searching Authority Re. Application No. PCT/IL2013/051098. (19 Pages).
International Search Report and the Written Opinion Dated Feb. 16, 2023 From the International Searching Authority Re. Application No. PCT/IL2022/051378 (11 Pages).
International Search Report and the Written Opinion Dated Sep. 16, 2019 From the International Searching Authority Re. Application No. PCT/IL2019/050783. (15 Pages).
International Search Report and the Written Opinion Dated Sep. 18, 2019 From the International Searching Authority Re. Application No. PCT/IL2019/050782. (16 Pages).
International Search Report and the Written Opinion Dated Feb. 25, 2018 From the International Searching Authority Re. Application No. PCT/IL2018/050017. (11 Pages).
International Search Report and the Written Opinion Dated Feb. 27, 2018 From the International Searching Authority Re. Application No. PCT/IL2018/050014. (11 Pages).
Interview Summary Dated Aug. 5, 2021 from the US Patent and Trademark Office Re. U.S. Appl. No. 16/027,382. (2 pages).
Interview Summary Dated Feb. 17, 2023 from the US Patent and Trademark Office Re. U.S. Appl. No. 16/027,382. (2 pages).
Invitation to Pay Additional Fees, Communication Relating to the Results of the Partial International Search Dated Mar. 10, 2022 From the International Searching Authority Re. Application No. PCT/IL2022/050055. (7 Pages).
Notice of Allowance Dated Apr. 4, 2018 From the US Patent and Trademark Office Re. U.S. Appl. No. 14/655,752. (11 pages).
Notice of Allowance Dated Dec. 9, 2021 from US Patent and Trademark Office Re. U.S. Appl. No. 16/475,683. (12 pages).
Notice of Allowance Dated Feb. 24, 2023 from the US Patent and Trademark Office Re. U.S. Appl. No. 16/475,705. (21 pages).
Notice of Allowance Dated Jun. 25, 2021 from the US Patent and Trademark Office Re. U.S. Appl. No. 16/473,631. (16 pages).
Notice of Allowance Dated Sep. 30, 2022 from US Patent and Trademark Office Re. Application No. 16/475,139. (11 pages).
Notice of Eligibility for Grant Dated Feb. 28, 2022 From the Intellectual Property Office of Singapore, IPOS Re. Application No. 11201905679S. (1 page).
Notice of Reason(s) for Rejection Dated May 23, 2023 From the Japan Patent Office Re. Application No. 2021-500829. (3 pages).
Notice of Reason(s) for Rejection Dated Nov. 25, 2022 From the Japan Patent Office Re. Application No. 2019-536286 and Its Translation Into English. (7 pages).
Notice of Reason(s) for Rejection Dated Sep. 28, 2021 From the Japan Patent Office Re. Application No. 2019-536286 and Its Translation Into English. (11 Pages).
Notice of Reason(s) for Rejection Dated Sep. 28, 2021 From the Japan Patent Office Re. Application No. 2019-536308 and Its Translation Into English. (8 Pages).
Notice of Reasons for Rejection Dated Apr. 26, 2022 From the Japan Patent Office Re. Application No. 2019-536286 and Its Translation Into English. (12 pages).
Notice of Reasons for Rejection Dated Apr. 26, 2022 From the Japan Patent Office Re. Application No. 2019-536308. (3 Pages).
Notice of the Results of the Patent Fee Check Dated May 30, 2022 From the Federal Government Institution, Federal Institute of Industrial Property of the Federal Service of Intellectual Property, Patents and Trademarks of the Russian Federation, FIPS Re. 2021101108. (3 Pages).

(56) References Cited

OTHER PUBLICATIONS

Notification of Office Action and Search Report Dated Jun. 1, 2023 From the State Intellectual Property Office of the People's Republic of China Re. Application No. 201980052864.9. (7 Pages).
Notification of Office Action and Search Report Dated Jun. 2, 2023 From the State Intellectual Property Office of the People's Republic of China Re. Application No. 201980052845.6. (7 Pages).
Notification of Office Action and Search Report Dated Jun. 7, 2023 From the State Intellectual Property Office of the People's Republic of China Re. Application No. 202080063464.0. (8 Pages).
Notification of Office Action and Search Report Dated Oct. 9, 2022 From the State Intellectual Property Office of the People's Republic of China Re Application No. 201880016069.X. (13 Pages).
Notification of Office Action and Search Report Dated Dec. 15, 2017 From the State Intellectual Property Office of the People's Republic of China Re. Application No. 201380074192.4. (7 Pages).
Notification of Office Action and Search Report Dated Sep. 28, 2022 From the State Intellectual Property Office of the People's Republic of China Re. Application No. 201880015833.1. (9 Pages).
Notification of Office Action Dated Jul. 10, 2018 From The State Intellectual Property Office of the People's Republic of China Re. Application No. 201380074192.4. and Its Summary In English. (5 Pages).
Notification of Office Action Dated Apr. 21, 2023 From the State Intellectual Property Office of the People's Republic of China Re. Application No. 201880015833.1 (5 pages).
Notification of Office Action Dated Apr. 27, 2023 From the State Intellectual Property Office of the People's Republic of China Re. Application No. 201880016069.X (7 pages).
Office Action Dated Aug. 14, 2018 From the Israel Patent Office Re. Application No. 239671 and Its Translation Into English. (7 Pages).
Office Action Dated Sep. 28, 2022 From the Israel Patent Office Re. Application No. 267861. (3 Pages).
Office Action Dated Sep. 29, 2022 From the Israel Patent Office Re. Application No. 267862. (3 Pages).
Official Action Dated Jun. 1, 2022 from US Patent and Trademark Office Re. U.S. Appl. No. 17/258,170. (82 pages).
Official Action Dated Mar. 2, 2022 from US Patent and Trademark Office Re. U.S. Appl. No. 16/475,705. (79 pages).
Official Action Dated Aug. 5, 2022 from US Patent and Trademark Office Re. U.S. Appl. No. 16/027,382. (37 pages).
Official Action Dated Oct. 6, 2017 From the US Patent and Trademark Office Re. U.S. Appl. No. 14/655,752. (9 pages).
Official Action Dated Jul. 7, 2021 from the US Patent and Trademark Office Re. U.S. Appl. No. 16/475,683. (46 pages).
Official Action Dated Sep. 7, 2022 from US Patent and Trademark Office Re. U.S. Appl. No. 16/475,705. (34 pages).
Official Action Dated May 8, 2023 from the US Patent and Trademark Office Re. U.S. Appl. No. 17/400,179. (48 pages).
Official Action Dated Jun. 12, 2023 from the US Patent and Trademark Office Re. U.S. Appl. No. 16/027,382. (49 pages).
Official Action Dated Apr. 13, 2023 from the US Patent and Trademark Office Re. U.S. Appl. No. 17/258,170. (27 pages).
Official Action Dated Nov. 13, 2020 from the US Patent and Trademark Office Re. U.S. Appl. No. 16/027,382. (41 pages).
Official Action Dated Dec. 14, 2022 from the US Patent and Trademark Office Re. U.S. Appl. No. 16/475,705. (7 pages).
Official Action Dated Oct. 17, 2022 from US Patent and Trademark Office Re. U.S. Appl. No. 16/027,382. (16 pages).
Official Action Dated Jan. 21, 2022 from US Patent and Trademark Office Re. U.S. Appl. No. 16/027,382. (21 pages).
Official Action Dated Jun. 24, 2022 from US Patent and Trademark Office Re. U.S. Appl. No. 16/475,139. (97 pages).
Official Action Dated Mar. 29, 2021 From the US Patent and Trademark Office Re. U.S. Appl. No. 16/473,631. (34 Pages).
Official Action Dated Sep. 29, 2022 from US Patent and Trademark Office Re. U.S. Appl. No. 17/400,179. (104 pages).
Official Action Dated Mar. 30, 2017 From the US Patent and Trademark Office Re. U.S. Appl. No. 14/655,752. (12 Pages).
Patent Examination Report Dated Apr. 6, 2021 From the Australian Government, IP Australia Re. Application No. 2018205890.(4 Pages).
Patent Examination Report Dated 26 Marcch 2021 From the Australian Government, IP Australia Re. Application No. 2018205888. (4 Pages).
Request for Examination and Search Report Dated Dec. 5, 2022 From the (Rospatent), Federal Government Institution of Industrial Property of the Federal Service of Intellectual Property, Patents and Trademark of the Russian Federation Re. Application No. 2021101108 and Its Summary in English. (16 Pages).
Request for Examination and Search Report Dated Apr. 9, 2021 From the (Rospatent), Federal Government Institution of Industrial Property of the Federal Service of Intellectual Property, Patents and Trademark of the Russian Federation Re. Application No. 2019124676 and Its Translation Into English. (40 Pages).
Request for Examination and Search Report Dated Jan. 12, 2023 From the (Rospatent), Federal Government Institution of Industrial Property of the Federal Service of Intellectual Property, Patents and Trademark of the Russian Federation Re. Application No. 2021101091. (13 Pages).
Request for Examination Dated Jun. 7, 2023 From the Federal Government Institution, Federal Institute of Industrial Property of the Federal Service of Intellectual Property, Patents and Trademarks of the Russian Federation, FIPS Re. Application No. 2021101091. (19 Pages).
Request for Examination Dated Sep. 8, 2021 From the (Rospatent), Federal Government Institution of Industrial Property of the Federal Service of Intellectual Property, Patents and Trademark of the Russian Federation Re. Application No. 2019124678. (12 Pages).
Request for Examination Dated Sep. 8, 2021 From the Federal Government Institution, Federal Institute of Industrial Property of the Federal Service of Intellectual Property, Patents and Trademarks of the Russian Federation, FIPS Re. Application No. 2019124676. (14 Pages).
Request for Examination Dated Apr. 9, 2021 Fom the (Rospatent), Federal Government Institution of Industrial Property of the Federal Service of Intellectual Property, Patents and Trademark of the Russian Federation Re. Application No. 2019124678 and Its Translation Into English. (33 Pages).
Request for Examination Dated May 11, 2022 From the (Rospatent), Federal Government Institution of Industrial Property of the Federal Service of Intellectual Property, Patents and Trademark of the Russian Federation Re. Application No. 2022103192 and Its Translation Into English. (5 Pages).
Request for Examination Dated Apr. 14, 2023 From the Federal Government Institution, Federal Institute of Industrial Property of the Federal Service of Intellectual Property, Patents and Trademarks of the Russian Federation, FIPS Re. Application No. 2021101108. (7 Pages).
Requisition by the Examiner Dated Jun. 20, 2023 From the Innovation, Science and Economic Development Canada, Canadian Intellectual Property Office Re. Application No. 3,146,248. (8 pages).
Restriction Official Action Dated Jan. 5, 2022 from US Patent and Trademark Office Re. U.S. Appl. No. 16/475,705. (8 pages).
Restriction Official Action Dated Jun. 15, 2016 From the US Patent and Trademark Office Re. U.S. Appl. No. 14/655,752. (7 Pages).
Restriction Official Action Dated May 15, 2020 from the US Patent and Trademark Office Re. U.S. Appl. No. 16/027,382. (10 pages).
Restriction Official Action Dated Nov. 2, 2020 From the US Patent and Trademark Office Re. U.S. Appl. No. 16/473,631. (14 Pages).
Restriction Official Action Dated Mar. 26, 2021 from the US Patent and Trademark Office Re. U.S. Appl. No. 16/475,683. (9 pages).
Restriction Official Action Dated Jan. 28, 2022 from US Patent and Trademark Office Re. U.S. Appl. No. 17/258,170. (8 pages).
Restriction Official Action Dated Mar. 28, 2022 from US Patent and Trademark Office Re. U.S. Appl. No. 16/475,139. (10 pages).
Search Report and Written Opinion Dated Mar. 23, 2022 From the Intellectual Property Office of Singapore Re. Application No. 11202013167U. (10 Pages).
Search Report and Written Opinion Dated Mar. 23, 2022 From the Intellectual Property Office of Singapore, IPOS Re. Application No. 11202013170R. (10 Pages).

(56) References Cited

OTHER PUBLICATIONS

Search Report and Written Opinion Dated Feb. 24, 2023 From the Intellectual Property Office of Singapore, IPOS Re. Application No. 11202200041R. (15 Pages).
Search Report and Written Opinion Dated Apr. 25, 2020 From the Intellectual Property Office of Singapore Re. Application No. 11201905679S.
Search Report and Written Opinion Dated Apr. 25, 2020 From the Intellectual Propery Office of Singapore Re. Application No. 11201905681W. (10 Pages).
Summary Dated Nov. 4, 2022 of Notification of Office Action Dated Oct. 9, 2022 From the State Intellectual Property Office of the People's Republic of China Re. Application No. 201880016069.X. (5 Pages).
Summary Dated Oct. 18, 2022 of Notification of Office Action Dated Sep. 28, 2022 From the State Intellectual Property Office of the People's Republic of China Re. Application No. 201880015833.1. (1 Pages).
Supplementary European Search Report and the European Search Opinion Dated Mar. 7, 2022 From the European Patent Office Re. Application No. 19833103.5.(10 Pages).
Supplementary European Search Report and the European Search Opinion Dated Oct. 12, 2020 From the European Patent Office Re. Application No. 18735930.2. (8 Pages).
Supplementary European Search Report and the European Search Opinion Dated Nov. 19, 2020 From the European Patent Office Re. Application No. 18736642.2. (12 Pages).
Supplementary European Search Report and the European Search Opinion Dated Dec. 20, 2021 From the European Patent Office Re. Application No. 21179906.9. (8 Pages).
Supplementary European Search Report and the European Search Opinion Dated Mar. 23, 2022 From the European Patent Office Re. Application No. 19833260.3. (7 Pages).
Translation Dated Oct. 1, 2021 of Request for Examination Dated Sep. 8, 2021 From the (Rospatent), Federal Government Institution of Industrial Property of the Federal Service of Intellectual Property, Patents and Trademark of the Russian Federation Re. Application No. 2019124678. (8 Pages).
Translation Dated Oct. 5, 2021 of Request for Examination Dated Sep. 8, 2021 From the Federal Government Institution, Federal Institute of Industrial Property of the Federal Service of Intellectual Property, Patents and Trademarks of the Russian Federation, FIPS Re. Application No. 2019124676. (11 Pages).
Translation Dated May 12, 2023 of Notification of Office Action Dated Apr. 21, 2023 From the State Intellectual Property Office of the People's Republic of China Re. Application No. 201880015833.1 (6 pages).
Translation Dated Jun. 15, 2023 of Notice of Reason(s) for Rejection Dated May 23, 2023 From the Japan Patent Office Re. Application No. 2021-500829. (3 pages).
Translation Dated May 15, 2023 of Request for Examination Dated Apr. 14, 2023 From the Federal Government Institution, Federal Institute of Industrial Property of the Federal Service of Intellectual Property, Patents and Trademarks of the Russian Federation, FIPS Re. Application No. 2021101108. (4 Pages).
Translation Dated Nov. 17, 2022 of Notification of Office Action Dated Sep. 28, 2022 From the State Intellectual Property Office of the People's Republic of China Re. Application No. 201880015833.1. (9 Pages).
Translation Dated Mar. 22, 2023 of Grounds of Reason of Rejection Dated Mar. 7, 2023 From the Korean Intellectual Property Office Re. Application No. 10-2019-7022848. (5 Pages).
Translation Dated Dec. 23, 2022 of Request for Examination Dated Dec. 5, 2022 From the (Rospatent), Federal Government Institution of Industrial Property of the Federal Service of Intellectual Property, Patents and Trademark of the Russian Federation Re. Application No. 2021101108. (10 pages).
Translation Dated Jul. 25, 2018 of Notification of Office Action Dated Jul. 10, 2018 From The State Intellectual Property Office of the People's Republic of China Re. Application No. 201380074192.4. (5 Pages).
Translation Dated Apr. 27, 2023 of Grounds of Reason of Rejection Dated Apr. 5, 2023 From the Korean Intellectual Property Office Re. Application No. 10-2019-7022855. (3 Pages).
Translation Dated Jan. 30, 2023 of Request for Examination and Search Report Dated Jan. 12, 2023 From the (Rospatent), Federal Government Institution of Industrial Property of the Federal Service of Intellectual Property, Patents and Trademark of the Russian Federation Re. Application No. 2021101091. (9 pages).
Translation of Notification of Office Action and Search Report Dated Dec. 15, 2017 From the State Intellectual Property Office of the People's Republic of China Re. Application No. 201380074192.4. (9 Pages).
Written Opinion Dated Jan. 18, 2022 From the Intellectual Property Office of Singapore, IPOS Re. Application No. 11201905681W. (8 Pages).
Written Opinion Dated Sep. 28, 2021 From the Intellectual Property Office of Singapore Re. Application No. 11201905679S. (9 Pages).
Aaron "Overview of Fungal Skin Infections", Merck Manual, 1-2, accessed Feb. 19, 2019.
Abbs "US-16-473-631-1 Pep vs. US-17-258-170-13 Pep Align", ABSS Application, 1 P., May 18, 2022.
Abbs "WO_2014121093_ABSS_Sequence_Comparison", ABBS Application, 5 P., May 17-18, 2022.
Absolute Antibody "Antibody Sequencing, Engineering & Recombinant Expression", Absolute Antibody, Home Products, Website, 3 P., 2019.
Absolute Antibody "Bispecific and Trispecific Antibodies", Absolute Antibody, Website, Home Products, Website, 3 P., 2019.
Absolute Antibody "Products Archive", Absolute Antibody, Home Products, Website, 2 P., 2019.
Abss "US-17-400-179-2 Pep vs. US-17-258-170-13 Pep Align", ABSS Application, 1 P., May 18, 2018.
Abss WO_2014121093 ABSS Sequence Comparison, Generated by Examiner Using the ABSS Application, 1 P., May 16-17, 2022.
Amann "US_20160200833_ABSS_Sequence_Comparisons", Generated by Examiner Using the ABSS, 1-7 P., May 17, 2022.
Amiot et al. "Biology of HLA-G in Cancer: A Candidate Molecule for Therapeutic Intervention?", Cellular and Molecular Life Sciences, 68(3): 417-431, Published Online Nov. 10, 2010.
Anna et al. "First Immunotherapeutic CAR-T Cells Against the Immune Checkpoint Protein HLA-G", Journal for ImmunoTherapy of Cancer, 9(3): e001998-1-e001998-14, Mar. 2021.
Antoniou et al. "Transgenes Excompassing Dual-Promoter CpG Islands From the Human TBPand HNRPA2B1 Loci Are Resistant to Heterochromatin-Mediated Silencing", Genomics, 82(3): 269-279, Sep. 2003.
Arora et al. "Belatacept: A New Biological Agent for Maintenance Immunosuppression in Kidney Transplantation", Expert Opinion on Biological Therapy, 12(7): 965-979, Published Online May 8, 2012.
Ascierto et al. "Clinical Experiences With Anti-CD137 and Anti-PD1 Therapeutic Antibodies", Seminars in Oncology, XP008175440, 27(5): 508-516, Oct. 1, 2010.
Barclay et al. "The Interaction Between Signal Regulatory Protein Alpha (SIRPα) and CD47: Structure, Function, and Therapeutic Target", Annual Review of Immunology, 32: 25-50, Nov. 6, 2013.
Beha et al. "IL-15-Based Trifunctional Antibody-Fusion Proteins With Costimulatory TNF-Superfamily Ligands in the Single-Chain Format for Cancer Immunotherapy", Molecular Cancer Therapeutics, p. 1-35, Published Ahead of Print Apr. 30, 2019.
Berry et al. "Substitution of Cysteine for Selenocysteine in Type I Iodothyronine Deiodinase Reduces the Catalytic Efficiency of the Protein But Enhances its Translation", Endocrinology, 131(4): 1848-1852, Oct. 1, 1992.
Blaschitz et al. "Reaction Patterns of Monoclonal Antibodies to HLA-G in Human Tissues and on Cell Lines: A Comparative Study", Human Immunology, 61(11): 1074-1085, Nov. 2000.
Bowie et al. "Deciphering the Message in Protein Sequences: Tolerance to Amino Acid Substitutions", Science 247(4948):1306-1310, Mar. 16, 1990.

(56) References Cited

OTHER PUBLICATIONS

Burgess et al. "Possible Dissociation of the Heparin-binding and Mitogenic Activities of Heparin-binding (acidic fibroblast) Growth Factor-1 from its Receptor-binding Activities by Site-directed Mutagenesis of a Single Lysine Residue", Jurnal of Cell Biology (1990) 111 (5): 2129-2138, Nov. 1, 1990.
Carosella et al. "Beyond the Increasing Complexity of the Immunomodulatory HLA-G Molecule", Blood, 111(10): 4862-4870, Published Online Mar. 11, 2008.
Carosella et al. "HLA-G: An Immune Checkpoint Molecule", Advances in Immunology, 127: 33-144, Published Online May 27, 2015.
Carosella et al. "HLA-G: From Biology to Clinical Benefits", Trends in Immunology, 29(3): 125-132, Available Online Feb. 4, 2008.
CDC "Types of Fungal Diseases", Center for Disease Control and Prevention, 1-2, accessed May 21, 2021.
Cendrowicz et al. "DSP107 Combines Inhibition of CD47/SIRP Alpha Axis With Activation of 4-1BB to Trigger Anticancer Immunity", Journal of Experimental & Clinical Cancer Research, 41(1): 97-1-97-16, Mar. 14, 2022.
Chajut et al. "790 DSP502—A Novel Approach for Targeting TIGIT and PD1 Pathways for Cancer Immunotherapy", Journal for Immunotherapy of Cancer, 9(2): A825-A825, Nov. 30, 2021.
Chen et al. "Fusion Protein Linkers: Property, Design and Functionality", Advanced Drug Delivery Reviews, 65(10): 1357-1369, Oct. 15, 2013.
Clements et al. "Crystal Structure of HLA-G: A Nonclassical MHC Class I Molecule Expressed at the Fetal-Maternal Interface", Proc. Natl. Acad. Sci. USA, PNAS, 102(9): 3360-3365, Mar. 1, 2005.
Doron "Bacterial Infections: Overview", International Encyclopedia of Public Healthy, 2008 : 273-282, PMC7149789, Aug. 26, 2008.
Dranitzki-Elhalel et al. CD40 •FasL Inhibits Human T Cells: Evidence for An Auto-Inhibitory Loop-Back Mechanism, International Immunology, XP001668353, 19(4): 355-363, Advance Access Publication Feb. 20, 2007.
Edgar "T cell immunodeficiency", Journal of Clinical Pathology, 61(9): 988-993, Aug. 28, 2008.
Eisele et al. "APO010, A Synthetic Hexameric CD95 Ligand, Induces Human Glioma Cell Death In Vitro and In Vivo", Neuro-Oncology, 13(2): 155-164, Published Online Dec. 22, 2010.
Fellermeier et al. "Advancing Targeted Co-Stimulation With Antibody-Fusion Proteins by Introducing TNF Superfamily Members in a Single-Chain Format", Oncoimmunology, 5(11): e1238540-1-e1238540-11, Sep. 27, 2016.
Feng et al. "CTLA4-Fas Ligand Gene Transfer Mediated by Adenovirus Induce Long-Time Survival of Murine Cardiac Allografts", Transplantation Proceedings, 37(5): 2379-2381, Jun. 2005.
Frankel et al. Characterization of Diphtheria Fusion Proteins Targeted to the Human Interleukin-3 Receptor , Protein Engineering, Design and Selection, 13(8);575-581, Aug. 1, 2000.
Gasser et al. "Antibody Production With Yeasts and Filamentous Fungi: on the Road to Large Scale?", Biotechnology Letters, 29: 201-212, Nov. 22, 2006.
Gozlan et al. "Abstract A076: DSP107—A novel SIRPα-4-1 BBL Dual Signaling Protein (DSP) for Cancer Immunotherapy", Cancer Immunology Research, XP55734527A,7(2): 2P., Feb. 2019.
Gregory "Neuroblastoma", Merck Manual, 1-4, accessed Dec. 3, 2017.
Grewal et al. "CD40 and CD154 in Cell-Mediated Immunity", Annual Review of Immunology, 16:111-135, Publication date: Apr. 1998.
Ha et al. "Immunoglobulin Fc Heterodimer Platform Technology: From Design to Applications in Therapeutic Antibodies and Proteins", Frontiers in Immunology, 7(394): 1-16, Oct. 2016.
Halin et al. "Synergistic Therapeutic Effects of a Tumor Targeting Antibody Fragment, Fused to Interleukin 12 and to Tumor Necrosis Factor α", Cancer Research, 63(12):3202-3210, Jun. 15, 2003.
Herrero-Beaumont et al. "Abatacept Mechanism of Action: Concordance With Its Clinical Profile?", Reumatologia Clinica, 8(2): 78-83, Available Online Feb. 15, 2012.
Hershman "Thyroid cancers", 1-4, Dec. 3, 2017.
Holler et al. "Two Adjacent Trimeric Fas Ligands Are Required for Fas Signaling and Formation of a Death-Inducing Signaling Complex", Molecular and Cellular Biology, XP002258597, 23(4): 1428-1440, Feb. 2003. Abstract.
Huang et al. "CTLA-4-Fas Ligand Functions as a Trans Signal Converter Protein in Bridging Antigen-Presenting Cells and T Cells", International Immunology, XP001147390, 13(4): 529-539, Apr. 1, 2001. p. 537, r-h col. Last Para, Fig. 1.
Hung et al. "TIGIT and PD-1 Dual Checkpoint Blockade Enhances Antitumor Immunity and Survival in GBM", OncoImmunology, 7(8): e1466769-1-e1466769-14, May 24, 2018.
Itoh et al. "Optimization of the Inter-Domain Structure of Galectin-9 for Recombinant Production", Glycobiology, 23(8): 920-925, Mar. 18, 2013.
Jin et al. "Simultaneous Stimulation of Fas-Mediated Apoptosis and Blockade of Costimualtion Prevent Autoimmune Diabetes in Mice Induced by Multiple Low-Dose Streptozotocin", Gene Therapy, 11(12): 982-991, Published Online Mar. 25, 2004.
Jones et al. "Leukocyte Immunoglobulin-like Receptor Subfamily B Member 2 Soluble Isoform [*Homo sapiens*]", Database NCBI [Online], GenBank: ACK56072.1, Database Accession No. ACK56072, 3 pages, Feb. 18, 2010.
Kadagidze et al. Targeted Immunotherapy in Oncology, Allergiology and Immunology, 16(4):352, Nov. 2015, Abstract with English Translation.
Kahr Medical "DSP105 (PD1-41BBL): Targeted Immune Activation Leading to T-Cell Mediated Tumor Destruction", Kahr Medical, Product Description, p. 1-4, Apr. 29, 2018.
Kaiko et al. "Immunological Decision-Making: How Does The Immune System Decide to Mount a Helper T-Cell Response", Immunology, 123(3):326-338, Jan. 18, 2008.
Kang et al. "Inhibitory Leukocyte Immunoglobulin-Like Receptors: Immune Checkpoint Proteins and Tumor Sustaining Factors", Cell Cycle, 15(1): 25-40, Jan. 2, 2016.
Katz "Inhibition of Inflammatory Responses by Leukocyte Ig-Like Receptors", Advances in Immunology, 91: 251-272, Jan. 2006.
Keskin et al. "A New, Structurally Nonredundant, Diverse Data Set of Protein-Protein Interfaces and Its Implications", Protein Science, 13(4): 1043-1055, Apr. 2004.
Kleinsmith et al. "Understanding Cancer and Related Topics—Understanding Cancer", National Cancer Institute, 1-63, 2007, accessed Aug. 21, 2014.
Kontermann et al. "Bispecific Antibodies", Drug Discovery Today, 20(7): 838-847, Jul. 2015.
Kornbluth et al. "Multimeric Soluble 4-1BBL as a T Cell Stimulator for Adoptive Immunotherapy", The Journal of Immunology, 198(1): Suppl., Poster, May 1, 2017.
Kosobokova et al. "Antibody-cytokine Fusion Proteins: Production, Functionality and Application Prospects in Oncology", Contemporary Technologies in Medicine 2013-5(4): 102-111, Jun. 27, 2013.
Kramer "Overview of Viruses", Merck Manual, 1-6, accessed Feb. 19, 2019.
Lazar et al. "Transforming Growth Factor: Mutation of Aspartic Acid 47 and Leucine 48 Results in Different Boiological Activities", Molecular and Cellular Biology, 8(3): 1247-1252, Mar. 1998.
Lazar-Molnar et al. "Crystal Structure of the Complex Between Programmed Death-1 (PD-1) and Its Ligand PD-2", Proc. Natl. Acad. Sci. USA, PNAS, 105(30): 10483-10488, Jul. 29, 2008.
Lin et al. "Human Leukocyte Antigen-G (HLA-G) Expression in Cancers: Roles in Immunc Evasion, Metastasis and Target for Therapy", Molecular Medicine, 21(1): 782-791, Published Online Aug. 24, 2015.
Locksley et al. "The TNF and TNF Receptor Superfamilies: Integrating Mammalian Biology", Cell, 104(4): 487-501, Feb. 23, 2001.
Maeda et al. "Engineering of Functional Chimeric Protein G-VargulaLuciferase", Analytical Biochemistry,249(2): 147-152, Jul. 1, 1997.
Master "Renal Cell Carcinoma", Merck Manual, 1-6, accessed Dec. 3, 2017.

(56) References Cited

OTHER PUBLICATIONS

Maute et al. "Engineering High-Affinity PD-1 Variants for Optimized Immunotherapy and Immuno-PET Imaging", Proc. Natl. Acad. Sci., USA, PNAS, 112 (47): E6506-E6514, Published Online Nov. 10, 2015.
Menier et al. "Characterization of Monoclonal Antibodies Recognizing HLA-G or HLA-E: New Tools to Analyze the Expression of Nonclassical HLA Class I Molecules", Human Immunology, 64(3): 315-326, Mar. 2003.
Merchant et al. "An Efficient Route to Human Bispecific IgG", Nature Biotechnology, 16(7): 677-681, Jul. 1998.
Merck "Bladder Cancer", Merck Manual, p. 1-2, Accessed Aug. 21, 2014.
Merck "Colorectal Cancer", Merck Manual, p. 1-5, Accessed Online Aug. 21, 2014.
Merck "Overview of Fungal Infections", Merck Manual, p. 1-3, Accessed Oct. 21, 2020.
Merck "Overview of Leukemia", Merck Manual, p. 1-2, Accessed Aug. 21, 2014.
Merck "Overview of Lymphoma", Merck Manual, 1 P., Accessed Aug. 21, 2014.
Merck "Prostate Cancer", Merck Manual, p. 1-8, Accessed Aug. 21, 2014.
Muller et al. "Spliceosomal Peptide P140 forImmunotherapy of Systemic Lupus Erythematosus: Results of an Early Phase II Clinical Trial*", Arthritis and Rheumatology, 58(12): 3873-3883, Nov. 26, 2008.
Nalamalpu et al. "Booster for Driving Long Onchip Interconnects—Design Issues, Interconnect Synthesis, and Comparison With Repeaters", IEEE Transactions on Computer-Aided Design of Integrated Circuits and Systems, 21(1): 50-62, Jan. 2002.
Nguyen "Blocking 'Don't Eat Me' Signals CD47 and LILRB2 to Enhance Macrophage-and Granulocyte-Mediated Phagocytosis of Cancer Cells", Thesis, p. 1-31, Jul. 31, 2019.
NIH "Antimicrobial Resistance Threats", National Institute of Allergy and Infectious Diseases, p. 1-3, 2020.
Orbach et al. "CD40 • FasL and CTLA-4 • FasL Fusion Proteins Induce Apoptosis in Malignant Cell Lines by Dual Signaling", The American Journal of Pathology, XP009155963, 177(6): 3159-3168, Dec. 2010. Abstract.
Orbach ct al. "CTLA-4 • FasL Induces Early Apoptosis of Activated T Cells by Interfering With Anti-Apoptotic Signals", The Journal of Immunology, XP002668354, 179(11): 7287-7294, Dec. 1, 2007.
Pakula et al. "Genetic Analysis of Protein Stability and Function", Annual Review of Genetics, 23(1): 289-310, Dec. 1989.
Pearson "Approach to Parasitic Infections", Merck Manual, 1-10, accessed Oct. 22, 2020.
Pereg "Kahr Medical Dual Signaling Proteins (DSP) Platform—The Next Generation of Cancer Immunotherapy", Kahr Medical, Abstract Template for Company Presentations, 1 P., May 11, 2018.
Persson et al. "Transforming Growth Factor (TGF-b)-specific Signaling by Chimeric TGF-b Type II Receptor with Intracellular Domain of Activin Type IIB Receptor", Cell Biologt and Metabolism, 272(34): 1187-21194, Aug. 1997.
Prokofieva et al. "Course of Lectures on General Pharmacology: Teaching Aid, Ulyanovsk", Ulyanovsk State University, 155 pages, pp. 65-77. 2017, with its Translation into English.
Sanmamed et al. "Agonists of Co-Stimulation in Cancer Immunotherapy Directed Against CD137, OX40, GITR, CD27, CD28, and ICOS", Seminars in Oncology, XP055410294, 42(4): 640-655, Aug. 1, 2015.
Schreiber "US_20170095531_ABSS Sequence Comparison Findings 102", Generated by Examiner Using the ABSS Application, 1-5 P., May 17, 2022.
Shanks et al. "Are animal models predictive for humans?", Philosophy, Ethics, and Humanities in Medicine, 4(2):1-20, Jan. 15, 2009.
Shi et al. "Prolongation of Corneal Allograft Survival by CTLA4-FasL in a Murine Model", Graefe's Archive for Clinical and Experimental Ophthalmology, XP019542074, 245(11): 1691-1697, Published Online May 31, 2007.
Shiroishi et al. "Efficient Leukocyte Ig-Like Receptor Signalling and Crystal Structure of Disulfide-Linked HLA-G Dimer", The Journal of Biological Chemistry, 281(15): 10439-10447, Published Online Feb. 2, 2006.
Shiroishi et al. "Human Inhibitory Receptors Ig-Like Transcript 2 (ILT2) and ILT4 Compete With CD8 for MHC Class I Binding and Bind Preferentially to HLA-G", Proc. Natl. Acad. Sci. USA, PNAS, 100(15): 8856-8861, Jul. 22, 2003.
Shiroishi et al. "Structural Basis for Recognition of the Nonclassical MHC Molecule HLA-G by the Leukocyte Ig-Like Receptor B2 (LILRB2 / LIR2 / ILT4 / CD85d)", Proc. Natl. Acad. Sci. USA, PNAS, 103(44): 16412-16417, Oct. 31, 2006.
Shrimali et al. "Concurrent PD-1 Blockade Negates the Effects of OX40 Agonist in Combination Immunotherapy Through Inducing T-Cell Apoptosis", Cancer Immunology Research, 5(9): 755-766, Published Online Aug. 28, 2017.
Slavin et al. "Spontaneous Murine B-Cell Leukaemia", Nature, 272(5654): 624-626, Apr. 13, 1978.
Tansey et al. "The TNF Superfamily in 2009: New Pathways, New Indications, and New Drugs", Drug Discovery Today, 14(23/24): 1082-1088, Dec. 2009.
Tokuriki et al. "Stability Effects of Mutations and Protein Evolvability", Current Opinion in Structural Biology, 19(5):596-604, Oct. 2009.
Tsao Lung Carcinoma (Lung Cancer), Merck Manual, 1-18, accessed Dec. 3, 2017.
Uni Prot "Programmed Cell Death Protein 1", Uni Prot/NCBI Accession Q15116, Sequence Updated Apr. 17, 2017, 9 P., Accessed on Line Feb. 23, 2022.
UniProt "Tumor Necrosis Factor Ligand Superfamily Member 9", UniProt/NCBI Accession P41273, 4 P., Accessed Online Feb. 23, 2022, Sequence Updated Feb. 1, 1995.
Weiskopf et al. "Engineered SIRP-Alpha Variants as Immunotherapeutic Adjuvants to Anti-Cancer Antibodies", Science, 341(6141): 88-91, Jul. 5, 2013.
Willingham et al. "The CD47-Signal Regulatory Protein Alpha (SIRPα) Interaction is a Therapeutic Target for Human Solid Tumors", PNAS, 109(17): 6662-6667, Mar. 26, 2012.
Won et al. "The Structure of the Trimer of Human 4-1BB Ligand is Unique Among Members of the Tumor Necrosis Factor Superfamily", The Journal of Biological Chemistry, 285(12): 9202-9210, Mar. 19, 2010.
Wyzgol et al. "Trimer Stabilization, Oligomerization, and Antibody-Mediated Cell Surface Immobilization Improve the Activity of Soluble Trimers of CD27L, CD40L, 41BBL, and Glucocorticoid-InducedTNF Receptor Ligands", The Journal of Immunology, 183(3): 1851-1861, Published Online Jun. 13, 2009.
Xiao et al. "Soluble PD-1 Facilitates 4-1BBL-Triggered Antitumor Immunity Against Murine H22 Hepatocarcinoma In Vivo", Clinical Cancer Research, XP055144430, 13(6): 1823-1830, Published Online Feb. 26, 2007.
Yan "HLA-G Expression in Cancers: Potential Role in Diagnosis, Prognosis and Therapy", Endocrine, Metabolic & Immune Disorders—Drug Targets, 11(1): 76-89, Mar. 2011.
Yang et al. "High-Level Expression and Deletion Mutagenesis of Human Tryptophan Hydroxylase", Proceedings of the National Academy of Sciences ofthe United States of America, 91(14): 6659-6663, Jul. 5, 1994.
Yu et al. "The Surface Protein TIGIT Suppresses T Cell Activation by Promoting the Generation of Mature Immunoregulatory Dendritic Cells", Nature Immunology, 10: 48-57, 2009.
Zak et al. "Structure of the Complex of Human Programmed Death 1, PD-1, and Its Ligand PD-L1", Structure, 23(12): 2341-2348,Dec. 1, 2015.
Zhang et al. "Intraarticular Gene Delivery of CTLA4-FasL Suppresses Experimental Arthritis", International Immunology, 24(6): 379-388, Advance Access Publicaiton Feb. 21, 2012.

(56) References Cited

OTHER PUBLICATIONS

Zhang et al. "Targeted and Untargeted CD137L Fusion Proteins for the Immunotherapy of Experimental Solid Tumors", Clinical Cancer Research, XP055186494, 13(9): 2758-2767, May 1, 2007.
Notification on the Results of Checking the Patentability of an Invention Dated Aug. 25, 2023 From the Federal Government Institution, Federal Institute of Industrial Property of the Federal Service of Intellectual Property, Patents and Trademarks of the Russian Federation, FIPS Re. Application No. 2021101108 and Its Translation Into English. (7 pages).
Request for Examination and Search Report Dated Sep. 13, 2023 From the Federal Government Institution, Federal Institute of Industrial Property of the Federal Service of Intellectual Property, Patents and Trademarks of the Russian Federation, FIPS Re. Application No. 2022103192. (11 pages).
Requisition by the Examiner Dated Sep. 27, 2023 From the Innovation, Science and Economic Development Canada, Canadian Intellectual Property Office Re. Application No. 3,047,708. (5 Pages).
Badri et al. "Optimization of Radiation Dosing Schedules for Proneural Glioblastoma", Journal of Mathematical Biology, 72(5): 1301-1336, Jun. 21, 2015.
Baylot et al. "TCTP Has a Crucial Role in the Different Stages of Prostate Cancer Malignant 4 Progression 5", Results and Problems in Cell Differentiation, TCTP/tpt1—Remodeling Signaling from Stem Cell to Disease, 255-261, Nov. 18, 2017.
English Summary Dated Dec. 11, 2023 of Notification of Office Action Dated Nov. 23, 2023 From the State Intellectual Property Office of the People's Republic of China Re. Application No. 201980052864.9. (2 Pages).
Summary Dated Dec. 5, 2023 of Notification of Office Action Dated Nov. 25, 2023 From the State Intellectual Property Office of the People's Republic of China Re. Application No. 201980052845.6. (2 Pages).
Translation Dated Dec. 12, 2023 of Notice of Reason(s) for Rejection Dated Nov. 28, 2023 From the Japan Patent Office Re. Application No. 2021-500829. (2 pages).
Advisory Action Before the Filing of an Appeal Brief Dated Jun. 10, 2024 from US Patent and Trademark Office Re. U.S. Appl. No. 17/258,220. (2 pages).
Machine Translation Dated Jun. 10, 2024 of Notice of Reasons for Rejection Dated May 28, 2024 From the Japan Patent Office Re. Application No. 2019-536286. (2 pages).
Notice of Reasons for Rejection Dated May 28, 2024 From the Japan Patent Office Re. Application No. 2019-536286.(3 pages).
Restriction Official Action Dated Jun. 11, 2024 from the US Patent and Trademark Office Re. U.S. Appl. No. 18/101,601. (9 pages).
Examination Report Dated Jul. 10, 2025 From the Australian Government, IP Australia Re. Application No. 2019301316. (2 Pages).
Grounds of Reason of Rejection Dated May 9, 2025 From the Korean Intellectual Property Office Re. Application No. 10-2021-7004308 and its Summary and Machine Translation in English. (23 Pages).
Written Opinion Dated Oct. 9, 2023 From the Intellectual Property Office of Singapore, IPOS Re. Application No. 11201905681W. (7 Pages).
Official Action Dated Mar. 20, 2024 from the US Patent and Trademark Office Re. U.S. Appl. No. 17/258,220. (125 pages).
Notice of Allowance Dated Aug. 22, 2023 From the US Patent and Trademark Office Re. Application No. 17/400,179. (32 Pages).
Notice of Reason(s) for Rejection Dated Jul. 25, 2023 From the Japan Patent Office Re. Application No. 2022-132987 and Its Translation Into English. (7 Pages).
English Summary Dated Nov. 10, 2023 of Request for Examination and Search Report Dated Nov. 2, 2023 From the (Rospatent), Federal Government Institution of Industrial Property of the Federal Service of Intellectual Property, Patents and Trademark of the Russian Federation Re. Application No. 2021101091. (4 Pages).
Official Action Dated Nov. 9, 2023 from the US Patent and Trademark Office Re. U.S. Appl. No. 17/258,170. (62 pages).
Request for Examination and Search Report Dated Nov. 2, 2023 From the (Rospatent), Federal Government Institution of Industrial Property of the Federal Service of Intellectual Property, Patents and Trademark of the Russian Federation Re. Application No. 2021101091. (9 Pages).
Requisition by the Examiner Dated Nov. 7, 2023 From the Innovation, Science and Economic Development Canada, Canadian Intellectual Property Office Re. Application No. 3,104,778. (5 Pages).
Crasto et al. "Linker: A Program to Generate Linker Sequences for Fusion Proteins", Protein Engineering, 13(5): 309-312, May 1, 2000.
Supplementary European Search Report and the European Search Opinion Dated Nov. 26, 2025 From the European Patent Office Re. Application No. 22910378.3. (18 Pages).
Anonymous "Leukocyte Immunoglobulin Like Receptor A2 from Olive Baboon", Retrieved from the Internet, XP093335748, p. 1-2, Jun. 2, 2021.
Dietrich et al. "Human Inhibitory and Activating Ig-like Receptors Which Modulate the Function of Myeloid Cells", Microbes and Infection, XP093335636, 2: 323-329, Mar. 1, 2000.
Notice of Allowance Dated Sep. 18, 2024 From the US Patent and Trademark Office Re. U.S. Appl. No. 17/258,220. (24 Pages).
Written Opinion Dated Jan. 8, 2023 From the Intellectual Property Office of Singapore, IPOS Re. Application No. 11202200041R. (10 Pages).
International Preliminary Report on Patentability Dated Jul. 27, 2023 From the International Bureau of WIPO Re. Application No. PCT/IL2022/050055 (10 Pages).
Official Action Dated Nov. 6, 2023 from the US Patent and Trademark Office Re. U.S. Appl. No. 17/695,898. (159 pages).
Notice of Allowance Dated Jun. 27, 2024 together with Interview Summary Dated Jun. 3, 2024 from the US Patent and Trademark Office Re. U.S. Appl. No. 17/258,170. (20 Pages).
Notice of Reason(s) for Rejection Dated Jun. 18, 2024 From the Japan Patent Office Re. Application No. 2022-501004 and Its Translation Into English. (14 Pages).
Restriction Official Action Dated Jun. 24, 2024 From the US Patent and Trademark Office Re. U.S. Appl. No. 18/537,886. (12 pages).
Examination Report Dated Feb. 17, 2025 From the Instituto Mexicano de la Propiedad Industrial, Secretaria de Economia, Direccion Divisional de Patentes Re. Application No. MX/a/2021/0002653 and Its Translation Into English. (10 Pages).
Notice of Allowance Dated Feb. 18, 2025 together with Interview Summary Dated Jan. 24, 2025 from the US Patent and Trademark Office Re. U.S. Appl. No. 18/537,886. (53 pages).
Requisition by the Examiner Dated Feb. 11, 2025 From the Innovation, Science and Economic Development Canada, Canadian Intellectual Property Office Re. Application No. 3,047,708. (3 Pages).
Translation Dated Jul. 14, 2023 of Notice of Reason(s) for Rejection Dated Jun. 27, 2023 From the Japan Patent Office Re. Application No. 2021-500820. (4 pages).
Notice of Eligibility for Grant and Examination Report Dated Jul. 30, 2025 From the Intellectual Property Office of Singapore, IPOS Re. Application No. 11201905681W. (3 Pages).
Requisition by the Examiner Dated Aug. 3, 2023 From the Innovation, Science and Economic Development Canada, Canadian Intellectual Property Office Re. Application No. 3,104,780. (9 Pages).
Notification of Office Action Dated Dec. 14, 2023 From the State Intellectual Property Office of the People's Republic of China Re. Application No. 202080063464.0 and Its Machine Translation Into English. (13 Pages).
Requisition by the Examiner Dated Dec. 10, 2024 From the Innovation, Science and Economic Development Canada, Canadian Intellectual Property Office Re. Application No. 3,047,707. (5 Pages).

(56) References Cited

OTHER PUBLICATIONS

Machine Translation Dated Nov. 28, 2023 of Notification of Office Action Dated Nov. 23, 2023 From the State Intellectual Property Office of the People's Republic of China Re. Application No. 201980052864.9. (9 Pages).
Machine Translation Dated Nov. 29, 2023 of Notification of Office Action Dated Nov. 25, 2023 From the State Intellectual Property Office of the People's Republic of China Re. Application No. 201980052845.6. (5 Pages).
Notification of Office Action Dated Nov. 23, 2023 From the State Intellectual Property Office of the People's Republic of China Re. Application No. 201980052864.9. (4 Pages).
Notification of Office Action Dated Nov. 25, 2023 From the State Intellectual Property Office of the People's Republic of China Re. Application No. 201980052845.6. (5 Pages).
Written Opinion Dated Feb. 1, 2024 From the Intellectual Property Office of Singapore, IPOS Re. Application No. 11202013170R. (6 Pages).
Examination Report Dated Jun. 23, 2025 From the Australian Government, IP Australia Re. Application No. 2020311636. (4 Pages).
Grounds of Reason of Rejection Dated Jul. 22, 2025 From the Korean Intellectual Property Office Re. Application No. 10-2022-7004624. (4 Pages).
Office Action Dated Oct. 20, 2025 From the Israel Patent Office Re. Application No. 313778. (4 Pages).
English Summary Dated Jul. 4, 2023 of Notification of Office Action Dated Jun. 7, 2023 From the State Intellectual Property Office of the People's Republic of China Re. Application No. 202080063464.0. (4 pages).
Office Action Dated Jul. 6, 2023 From the Israel Patent Office Re. Application No. 267861. (3 Pages).
Translation Dated Oct. 10, 2023 of Request for Examination and Search Report Dated Sep. 13, 2023 From the Federal Government Institution, Federal Institute of Industrial Property of the Federal Service of Intellectual Property, Patents and Trademarks of the Russian Federation, FIPS Re. Application No. 2022103192. (6 pages).
Requisition by the Examiner Dated Nov. 15, 2023 From the Innovation, Science and Economic Development Canada, Canadian Intellectual Property Office Re. Application No. 3,047,707. (9 Pages).
Translation Dated Nov. 22, 2023 of Request for Examination and Search Report Dated Nov. 2, 2023 From the (Rospatent), Federal Government Institution of Industrial Property of the Federal Service of Intellectual Property, Patents and Trademark of the Russian Federation Re. Application No. 2021101091. (7 Pages).
Examination Report Under Sections 12 & 13 of the Patents Act, 1970 and the Patents Rules, 2003 Dated Dec. 1, 2023 From the Government of India, Intellectual Property India, Patents, Designs, Trade Marks, Geographical Indications, The Patent Office Re. Application No. 201927030333. (5 pages).
Notice of Reason(s) for Rejection Dated Nov. 28, 2023 From the Japan Patent Office Re. Application No. 2021-500829. (2 pages).
Corrected Notice of Allowability Dated Oct. 4, 2024 From the US Patent and Trademark Office Re. U.S. Appl. No. 17/258,220. (6 Pages).
Grounds of Reason of Rejection Dated Sep. 20, 2024 From the Korean Intellectual Property Office Re. Application No. 10-2021-7004308 and Its Summary in English. (19 Pages).
Official Action Dated Oct. 19, 2023 from the US Patent and Trademark Office Re. U.S. Appl. No. 17/258,220. (167 pages).
Chichili et al. "Linkers in The Structural Biology of Protein-Protein Interactions", Protein Science, 22(2): 153-167, Dec. 6, 2012.
English Summary Dated Dec. 27, 2023 of Notification of Office Action Dated Dec. 14, 2023 From the State Intellectual Property Office of the People's Republic of China Re. Application No. 202080063464.0. (5 Pages).
Official Action Dated Nov. 14, 2025 from the US Patent and Trademark Office Re. U.S. Appl. No. 17/626,185. (220 pages).
Fromm et al. "Agonist Redirected Checkpoint, PD1-FcOX40L, for Cancer Immunotherapy", Journal for ImmunoTherapy of Cancer, 6: 149, p. 1-16. 2018.
Patel et al. "Linkers: A Synergistic Way for The Synthesis of Chimeric Proteins", Protei Expression and Purification, 191. 106012, Mar. 2022. Abstract.
Sturgill et al. "TNFR Agonists: A Review of Current Biologics Targeting OX40, 4-1BB, CD27, and GITR", Tumor Necrosis Receptor Agonists, AJHO, 13(11): 4-15, 2017.
Yang et al. "Engineering of Fc Fragments with Optimized Physicochemical Properties Implying Improvement of Clinical Potentials for Fc-Based Therapeutics", Frontiers in Immunology, 8: 1860, p. 1-14, Jan. 8, 2018.
Restriction Official Action Dated Jan. 22, 2026 From the US Patent and Trademark Office Re. U.S. Appl. No. 18/272,154. (8 pages).
Requisition by the Examiner Dated Mar. 11, 2026 From the Innovation, Science and Economic Development Canada, Canadian Intellectual Property Office Re. Application No. 3,047,708. (3 Pages).
Office Action Dated Jan. 7, 2026 From the Israel Patent Office Re. Application No. 313778. (6 Pages).
Examination Report Under Sections 12 & 13 of the Patents Act, 1970 and the Patents Rules, 2003 Dated Apr. 1, 2026 From the Government of India, Intellectual Property India, Patents, Designs, Trade Marks, Geographical Indications, The Patent Office Re. Application No. 201927030081. (7 pages).
Examination Report Under Sections 12 & 13 of the Patents Act, 1970 and the Patents Rules, 2003 Dated Apr. 30, 2026 From the Government of India, Intellectual Property India, Patents, Designs, Trade Marks, Geographical Indications, The Patent Office Re. Application No. 202127002772. (9 pages).
Notice of Eligibility for Grant and Examination Report Dated Apr. 10, 2026 From the Intellectual Property Office of Singapore, IPOS Re. Application No. 11202013167U. (4 Pages).
Official Action Dated Apr. 30, 2026 from the US Patent and Trademark Office Rc. U.S. Appl. No. 18/272,154. (115 pages).
Relatório de Busca e Parecer [Search Report and Opinion] Dated Mar. 12, 2026 From the Serviço Público Federal, Ministério da Economia, Instituto Nacional da Propriedade Industrial do Brasil Re. Application No. BR 11 2021 000360 6 and Its Translation Into English. (7 Pages).
Search Report and Written Opinion Dated Mar. 15, 2026 From the Intellectual Property Office of Singapore, IPOS Re. Application No. 11202404329U. (11 Pages).
Delidakis et al. "Improving Antibody Therapeutics by Manipulating the Fc Domain: Immunological and Structural Considerations", Annual Review of Biomedical Engineering, 24: 249-274, Apr. 1, 2022.
Sun et al. "Structural Insights Into the Unique pH-Responsive Characteristics of the Anti-TIGIT Therapeutic Antibody Ociperlimab", Article, 32(5): 550-561, May 2, 2024.

* cited by examiner

| | CD27 | 41BB | PDL1 | CD47 |
|---|---|---|---|---|
| HT1080-WT | 0 | 0 | 540 | 139 |
| HT1080-CD27+ | 208 | 0 | 92 | 731 |
| HT1080-41BB+ | 0 | 1404 | 130 | 791 |
| DLD1-WT | 0 | 0 | 93 | 170 |
| DLD1-PDL1+ | 0 | 0 | 10098 | 215 |

| | |
|---|---|
| 50 ug/ml | 6887 |
| 25 ug/ml | 7829 |
| 12.5 ug/ml | 9042 |
| 6.25 ug/ml | 7527 |
| 3.13 ug/ml | 8305 |
| 1.56 ug/ml | 6424 |
| 0.78 ug/ml | 4173 |
| 0.39 ug/ml | 2974 |
| 0.2 ug/ml | 1414 |
| 0.1 ug/ml | 887 |
| 0.05 ug/ml | 480 |
| 0.02 ug/ml | 316 |
| 0.01 ug/ml | 203 |
| Isc-C+protein | 70.8 |
| Isc-C | 76.1 |
| Unstained | 73.4 |

| | |
|---|---|
| 50 ug/ml | 204 |
| 25 ug/ml | 105 |
| 12.5 ug/ml | 82.4 |
| 6.25 ug/ml | 71.3 |
| 3.13 ug/ml | 67.8 |
| 1.56 ug/ml | 64.3 |
| 0.78 ug/ml | 62.2 |
| 0.39 ug/ml | 58.8 |
| 0.2 ug/ml | 63.8 |
| 0.1 ug/ml | 55.6 |
| 0.05 ug/ml | 57.4 |
| 0.02 ug/ml | 56.0 |
| 0.01 ug/ml | 57.4 |
| Isc-C+protein | 43.2 |
| Isc-C | 43.0 |
| Unstained | 40.5 |

SEQUENCE LISTING

```
Sequence total quantity: 18
SEQ ID NO: 1            moltype = AA  length = 356
FEATURE                 Location/Qualifiers
REGION                  1..356
                        note = Amino-acid sequence of the chimera protein (PD1- G
                         -4-1BBL)
source                  1..356
                        mol_type = protein
                        organism = synthetic construct
SEQUENCE: 1
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV GACPWAVSGA RASPGSAASP RLREGPELSP  180
DDPAGLLDLR QGMFAQLVAQ NVLLIDGPLS WYSDPGLAGV SLTGGLSYKE DTKELVVAKA  240
GVYYVFFQLE LRRVVAGEGS GSVSLALHLQ PLRSAAGAAA LALTVDLPPA SSEARNSAFG  300
FQGRLLHLSA GQRLGVHLHT EARARHAWQL TQGATVLGLF RVTPEIPAGL PSPRSE      356

SEQ ID NO: 2            moltype = AA  length = 150
FEATURE                 Location/Qualifiers
source                  1..150
                        mol_type = protein
                        organism = Homo sapiens
SEQUENCE: 2
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV                                   150

SEQ ID NO: 3            moltype = AA  length = 205
FEATURE                 Location/Qualifiers
source                  1..205
                        mol_type = protein
                        organism = Homo sapiens
SEQUENCE: 3
ACPWAVSGAR ASPGSAASPR LREGPELSPD DPAGLLDLRQ GMFAQLVAQN VLLIDGPLSW  60
YSDPGLAGVS LTGGLSYKED TKELVVAKAG VYYVFFQLEL RRVVAGEGSG SVSLALHLQP  120
LRSAAGAAAL ALTVDLPPAS SEARNSAFGF QGRLLHLSAG QRLGVHLHTE ARARHAWQLT  180
QGATVLGLFR VTPEIPAGLP SPRSE                                        205

SEQ ID NO: 4            moltype = AA  length = 355
FEATURE                 Location/Qualifiers
REGION                  1..355
                        note = Amino-acid sequence of the chimera protein (PD1-
                         4-1BBL, no linker)
source                  1..355
                        mol_type = protein
                        organism = synthetic construct
SEQUENCE: 4
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV ACPWAVSGAR ASPGSAASPR LREGPELSPD  180
DPAGLLDLRQ GMFAQLVAQN VLLIDGPLSW YSDPGLAGVS LTGGLSYKED TKELVVAKAG  240
VYYVFFQLEL RRVVAGEGSG SVSLALHLQP LRSAAGAAAL ALTVDLPPAS SEARNSAFGF  300
QGRLLHLSAG QRLGVHLHTE ARARHAWQLT QGATVLGLFR VTPEIPAGLP SPRSE       355

SEQ ID NO: 5            moltype = AA  length = 362
FEATURE                 Location/Qualifiers
REGION                  1..362
                        note = Amino-acid sequence of His-tagged PD1-41BBL
source                  1..362
                        mol_type = protein
                        organism = synthetic construct
SEQUENCE: 5
HHHHHHPGWF LDSPDRPWNP PTFSPALLVV TEGDNATFTC SFSNTSESFV LNWYRMSPSN  60
QTDKLAAFPE DRSQPGQDCR FRVTQLPNGR DFHMSVVRAR RNDSGTYLCG AISLAPKAQI  120
KESLRAELRV TERRAEVPTA HPSPSPRPAG QFQTLVGACP WAVSGARASP GSAASPRLRE  180
GPELSPDDPA GLLDLRQGMF AQLVAQNVLL IDGPLSWYSD PGLAGVSLTG GLSYKEDTKE  240
LVVAKAGVYY VFFQLELRRV VAGEGSGSVS LALHLQPLRS AAGAAALALT VDLPPASSEA  300
```

```
RNSAFGFQGR LLHLSAGQRL GVHLHTEARA RHAWQLTQGA TVLGLFRVTP EIPAGLPSPR  360
SE                                                                362

SEQ ID NO: 6            moltype = AA  length = 554
FEATURE                 Location/Qualifiers
REGION                  1..554
                        note = Amino-acid sequence of SIRP alpha 41BBL
source                  1..554
                        mol_type = protein
                        organism = synthetic construct
SEQUENCE: 6
HHHHHHEEELQ VIQPDKSVLV AAGETATLRC TATSLIPVGP IQWFRGAGPG RELIYNQKEG  60
HFPRVTTVSD LTKRNNMDFS IRIGNITPAD AGTYYCVKFR KGSPDDVEFK SGAGTELSVR  120
AKPSAPVVSG PAARATPQHT VSFTCESHGF SPRDITLKWF KNGNELSDFQ TNVDPVGESV  180
SYSIHSTAKV VLTREDVHSQ VICEVAHVTL QGDPLRGTAN LSETIRVPPT LEVTQQPVRA  240
ENQVNVTCQV RKFYPQRLQL TWLENGNVSR TETASTVTEN KDGTYNWMSW LLVNVSAHRD  300
DVKLTCQVEH DGQPAVSKSH DLKVSAHPKE QGSNTAAENT GSNERNIYGA CPWAVSGARA  360
SPGSAASPRL REGPELSPDD PAGLLDLRQG MFAQLVAQNV LLIDGPLSWY SDPGLAGVSL  420
TGGLSYKEDT KELVVAKAGV YYVFFQLELR RVVAGEGSGS VSLALHLQPL RSAAGAAALA  480
LTVDLPPASS EARNSAFGFQ GRLLHLSAGQ RLGVHLHTEA RARHAWQLTQ GATVLGLFRV  540
TPEIPAGLPS PRSE                                                   554

SEQ ID NO: 7            moltype = AA  length = 312
FEATURE                 Location/Qualifiers
REGION                  1..312
                        note = Amino-acid sequence of PD1-CD70
source                  1..312
                        mol_type = protein
                        organism = synthetic construct
SEQUENCE: 7
HHHHHHPGWF LDSPDRPWNP PTFSPALLVV TEGDNATFTC SFSNTSESFV LNWYRMSPSN  60
QTDKLAAFPE DRSQPGQDCR FRVTQLPNGR DFHMSVVRAR RNDSGTYLCG AISLAPKAQI  120
KESLRAELRV TERRAEVPTA HPSPSPRPAG QFQTLVGQRF AQAQQQLPLE SLGWDVAELQ  180
LNHTGPQQDP RLYWQGGPAL GRSFLHGPEL DKGQLRIHRD GIYMVHIQVT LAICSSTTAS  240
RHHPTTLAVG ICSPASRSIS LLRLSFHQGC TIASQRLTPL ARGDTLCTNL TGTLLPSRNT  300
DETFFGVQWV RP                                                     312

SEQ ID NO: 8            moltype = DNA  length = 1086
FEATURE                 Location/Qualifiers
misc_feature            1..1086
                        note = Nucleic-acid sequence of PD1-41BBL (with his tag)
source                  1..1086
                        mol_type = other DNA
                        organism = synthetic construct
SEQUENCE: 8
caccatcatc accaccatcc tggctggttt ctggacagcc ccgacagacc ttggaaccct  60
cctacattca gccccgctct gctggtggtt accgagggcg ataatgccac cttcacctgt  120
agcttcagca acaccagcga gagcttcgtg ctgaactggt acagaatgag ccccagcaac  180
cagaccgaca agctggccgc ctttcctgag gatagatctc agcccggcca ggactgccgg  240
ttcagagtta cacagctgcc caacggccgg gacttccaca tgtctgtcgt ccgggccaga  300
agaaacgaca gcggcacata tctgtgcggc gccatttctc tggcccctaa ggctcagatc  360
aaagagagcc tgagagccga gctgagagtg acagaaagac gggccgaagt gcccacagct  420
caccccttcac cttctccaag acctgccggc cagtttcaga cactcgtggg agcttgtcct  480
tgggccgttt ctggcgctag agcctctcct ggatctgccg cttctcccag actgagagag  540
ggacctgagc tgagccctga tgatcctgct ggactgctgg atctgagaca gggcatgttt  600
gcccagctgg tggcccagaa tgtgctgctg attgatggcc ctctgtcctg gtacagcgat  660
cctggacttg ctggcgttag cctgactggc ggcctgagct acaaagagga caccaaagaa  720
ctggtggtgg ccaaggccgg cgtgtactac gtgttctttc agctggaact gcggagagtg  780
gtggccggcg aaggatctgg atctgtgtct ctggctctgc atctgcagcc tctgagatct  840
gctgctggtg ctgctgctct ggccctgaca gttgatctgc ctcctgcctc tagcgaggcc  900
agaaactccg cctttggctt ccaaggcaga ctgctgcacc tgagcgctgg acagagactg  960
ggagtccatc tgcacacaga agccagagct agacacgcct ggcagctgac acaaggcgct  1020
acagtgctgg gcctgttcag agtgacccct gagattccag ccggcctgcc atctcctaga  1080
tctgag                                                            1086

SEQ ID NO: 9            moltype = DNA  length = 1068
FEATURE                 Location/Qualifiers
misc_feature            1..1068
                        note = Nucleic-acid sequence of PD1-41BBL
source                  1..1068
                        mol_type = other DNA
                        organism = synthetic construct
SEQUENCE: 9
cctggctggt ttctggacag ccccgacaga ccttggaacc ctcctacatt cagccccgct  60
ctgctggtgg ttaccgaggg cgataatgcc accttcacct gtagcttcag caacaccagc  120
gagagcttcg tgctgaactg gtacagaatg agccccagca accagaccga caagctggcc  180
gcctttcctg aggatagatc tcagcccggc caggactgcc ggttcagagt tacacagctg  240
cccaacggcc gggacttcca catgtctgtc gtccgggcca gaagaaacga cagcggcaca  300
tatctgtgcg gcgccatttc tctggcccct aaggctcaga tcaaagagag cctgagagcc  360
```

```
gagctgagag tgacagaaag acgggccgaa gtgcccacag ctcacccttc accttctcca  420
agacctgccg gccagtttca gacactcgtg ggagcttgtc cttgggccgt ttctggcgct  480
agagcctctc ctggatctgc cgcttctccc agactgagag agggacctga gctgagccct  540
gatgatcctg ctggactgct ggatctgaga cagggcatgt ttgcccagct ggtggcccag  600
aatgtgctgc tgattgatgg ccctctgtcc tggtacagcg atcctggact tgctggcgtt  660
agcctgactg gcggcctgag ctacaaagag gacaccaaag aactggtggt ggccaaggcc  720
ggcgtgtact acgtgttctt tcagctggaa ctgcggagag tggtggccgg cgaaggatct  780
ggatctgtgt ctctggctct gcatctgcag cctctgagat ctgctgctgg tgctgctgct  840
ctggccctga cagttgatct gcctcctgcc tctagcgagg ccagaaactc cgcctttggc  900
ttccaaggca gactgctgca cctgagcgct ggacagagac tgggagtcca tctgcacaca  960
gaagccagag ctagacacgc ctggcagctg acacaaggcg ctacagtgct gggcctgttc  1020
agagtgaccc ctgagattcc agccggcctg ccatctccta gatctgag              1068

SEQ ID NO: 10          moltype = AA  length = 288
FEATURE                Location/Qualifiers
REGION                 1..288
                       note = Amino-acid sequence of full length PD1
source                 1..288
                       mol_type = protein
                       organism = synthetic construct
SEQUENCE: 10
MQIPQAPWPV VWAVLQLGWR PGWFLDSPDR PWNPPTFSPA LLVVTEGDNA TFTCSFSNTS  60
ESFVLNWYRM SPSNQTDKLA AFPEDRSQPG QDCRFRVTQL PNGRDFHMSV VRARRNDSGT  120
YLCGAISLAP KAQIKESLRA ELRVTERRAE VPTAHPSPSP RPAGQFQTLV VGVVGGLLGS  180
LVLLVWVLAV ICSRAARGTI GARRTGQPLK EDPSAVPVFS VDYGELDFQW REKTPEPPVP  240
CVPEQTEYAT IVFPSGMGTS SPARRGSADG PRSAQPLRPE DGHCSWPL              288

SEQ ID NO: 11          moltype = DNA  length = 867
FEATURE                Location/Qualifiers
misc_feature           1..867
                       note = Nucleic-acid sequence of full length PD1
source                 1..867
                       mol_type = other DNA
                       organism = synthetic construct
SEQUENCE: 11
atgcagatcc cacaggcgcc ctggccagtc gtctgggcgg tgctacaact gggctggcgg  60
ccaggatggt tcttagactc cccagacagg ccctggaacc cccccacctt ctccccagcc  120
ctgctcgtgg tgaccgaagg ggacaacgcc accttcacct gcagcttctc caacacatcg  180
gagagcttcg tgctaaactg gtaccgcatg agccccagca accagacgga caagctggcc  240
gccttccccg aggaccgcag ccagcccggc caggactgcc gcttccgtgt cacacaactg  300
cccaacgggc gtgacttcca catgagcgtg gtcagggccc ggcgcaatga cagcggcacc  360
tacctctgtg gggccatctc cctggccccc aaggcgcaga tcaaagagag cctgcgggca  420
gagctcaggg tgacagagag aagggcagaa gtgcccacag cccaccccag cccctcaccc  480
aggccagccg gccagttcca aaccctggtg gttggtgtcg tgggcggcct gctgggcagc  540
ctggtgctgc tagtctgggt cctggccgtc atctgctccc gggccgcacg agggacaata  600
ggagccaggc gcaccggcca gcccctgaag gaggacccct cagccgtgcc tgtgttctct  660
gtggactatg gggagctgga tttccagtgg cgagagaaga ccccggagcc ccccgtgccc  720
tgtgtccctg agcagacgga gtatgccacc attgtctttc ctagcggaat gggcacctca  780
tcccccgccc gcaggggctc agctgacggc cctcggagtg cccagccact gaggcctgag  840
gatggacact gctcttggcc cctctga                                     867

SEQ ID NO: 12          moltype = DNA  length = 450
FEATURE                Location/Qualifiers
misc_feature           1..450
                       note = Nucleic-acid sequence encoding the extracellular
                        domain of the human PD1 protein
source                 1..450
                       mol_type = other DNA
                       organism = synthetic construct
SEQUENCE: 12
ccaggatggt tcttagactc cccagacagg ccctggaacc cccccacctt ctccccagcc  60
ctgctcgtgg tgaccgaagg ggacaacgcc accttcacct gcagcttctc caacacatcg  120
gagagcttcg tgctaaactg gtaccgcatg agccccagca accagacgga caagctggcc  180
gccttccccg aggaccgcag ccagcccggc caggactgcc gcttccgtgt cacacaactg  240
cccaacgggc gtgacttcca catgagcgtg gtcagggccc ggcgcaatga cagcggcacc  300
tacctctgtg gggccatctc cctggccccc aaggcgcaga tcaaagagag cctgcgggca  360
gagctcaggg tgacagagag aagggcagaa gtgcccacag cccaccccag cccctcaccc  420
aggccagccg gccagttcca aaccctggtg                                  450

SEQ ID NO: 13          moltype = AA  length = 254
FEATURE                Location/Qualifiers
REGION                 1..254
                       note = Amino-acid sequence of full length 41BBL
source                 1..254
                       mol_type = protein
                       organism = synthetic construct
SEQUENCE: 13
MEYASDASLD PEAPWPPAPR ARACRVLPWA LVAGLLLLLL LAAACAVFLA CPWAVSGARA  60
SPGSAASPRL REGPELSPDD PAGLLDLRQG MFAQLVAQNV LLIDGPLSWY SDPGLAGVSL  120
```

```
TGGLSYKEDT KELVVAKAGV YYVFFQLELR RVVAGEGSGS VSLALHLQPL RSAAGAAALA  180
LTVDLPPASS EARNSAFGFQ GRLLHLSAGQ RLGVHLHTEA RARHAWQLTQ GATVLGLFRV  240
TPEIPAGLPS PRSE                                                   254

SEQ ID NO: 14          moltype = DNA  length = 765
FEATURE                Location/Qualifiers
misc_feature           1..765
                       note = Nucleic-acid sequence of full length 41BBL
source                 1..765
                       mol_type = other DNA
                       organism = synthetic construct
SEQUENCE: 14
atggaatacg cctctgacgc ttcactggac cccgaagccc cgtggcctcc cgcgccccgc  60
gctcgcgcct gccgcgtact gccttgggcc ctggtcgcgg ggctgctgct gctgctgctg  120
ctcgctgccg cctgcgccgt cttcctcgcc tgcccctggg ccgtgtccgg ggctcgcgcc  180
tcgcccggct ccgcggccag cccgagactc cgcgagggtc ccgagctttc gcccgacgat  240
cccgccggcc tcttggacct gcggcagggc atgtttgcgc agctggtggc ccaaaatgtt  300
ctgctgatcg atgggcccct gagctggtac agtgacccag gcctggcagg cgtgtccctg  360
acgggggggcc tgagctacaa agaggacacg aaggagctgg tggtggccaa ggctggagtc  420
tactatgtct tctttcaact agagctgcgg cgcgtggtgg ccggcgaggg ctcaggctcc  480
gtttcacttg cgctgcacct gcagccactg cgctctgctg ctggggccgc cgccctggct  540
ttgaccgtgg acctgccacc cgcctcctcc gaggctcgga actcggcctt cggtttccag  600
ggccgcttgc tgcacctgag tgccggccag cgcctgggcg tccatcttca cactgaggcc  660
agggcacgcc atgcctggca gcttacccag ggcgccacag tcttgggact cttccgggtg  720
acccccgaaa tcccagccgg actcccttca ccgaggtcgg aataa                 765

SEQ ID NO: 15          moltype = DNA  length = 615
FEATURE                Location/Qualifiers
misc_feature           1..615
                       note = Nucleic-acid sequence encoding the extracellular
                        domain of the human 41BBL
source                 1..615
                       mol_type = other DNA
                       organism = synthetic construct
SEQUENCE: 15
gcctgcccct gggccgtgtc cggggctcgc gcctcgcccg gctccgcggc cagcccgaga  60
ctccgcgagg gtcccgagct ttcgcccgac gatcccgccg gcctcttgga cctgcggcag  120
ggcatgtttg cgcagctggt ggcccaaaat gttctgctga tcgatgggcc cctgagctgg  180
tacagtgacc caggcctggc aggcgtgtcc ctgacggggg gcctgagcta caaagaggac  240
acgaaggagc tggtggtggc caaggctgga gtctactatg tcttctttca actagagctg  300
cggcgcgtgg tggccggcga gggctcaggc tccgtttcac ttgcgctgca cctgcagcca  360
ctgcgctctg ctgctggggc cgccgccctg gctttgaccg tggacctgcc acccgcctcc  420
tccgaggctc ggaactcggc cttcggtttc cagggccgct tgctgcacct gagtgccggc  480
cagcgcctgg gcgtccatct tcacactgag gccagggcac gccatgcctg gcagcttacc  540
cagggcgcca cagtcttggg actcttccgg gtgacccccg aaatcccagc cggactccct  600
tcaccgaggt cggaa                                                  615

SEQ ID NO: 16          moltype = AA  length = 167
FEATURE                Location/Qualifiers
REGION                 1..167
                       note = PD1 amino acid sequence
source                 1..167
                       mol_type = protein
                       organism = synthetic construct
SEQUENCE: 16
MQIPQAPWPV VWAVLQLGWR PGWFLDSPDR PWNPPTFSPA LLVVTEGDNA TFTCSFSNTS  60
ESFVLNWYRM SPSNQTDKLA AFPEDRSQPG QDCRFRVTQL PNGRDFHMSV VRARRNDSGT  120
YLCGAISLAP KAQIKESLRA ELRVTERRAE VPTAHPSPSP RPAGQFQ               167

SEQ ID NO: 17          moltype = AA  length = 122
FEATURE                Location/Qualifiers
REGION                 1..122
                       note = PD1 amino acid sequence
source                 1..122
                       mol_type = protein
                       organism = synthetic construct
SEQUENCE: 17
DSPDRPWNPP TFSPALLVVT EGDNATFTCS FSNTSESFVL NWYRMSPSNQ TDKLAAFPED  60
RSQPGQDCRF RVTQLPNGRD FHMSVVRARR NDSGTYLCGA ISLAPKAQIK ESLRAELRVT  120
ER                                                                122

SEQ ID NO: 18          moltype = DNA  length = 1170
FEATURE                Location/Qualifiers
misc_feature           1..1170
                       note = The cloning sequence of PD1-41BBL in the vector
source                 1..1170
                       mol_type = other DNA
                       organism = synthetic construct
SEQUENCE: 18
```

-continued

```
gaattcccgc cgccaccatg ggctggtcct gcatcattct gtttctggtg gccacagcca   60
ccggcgtgca ctctcaccat catcaccacc atcctggctg gtttctggac agccccgaca  120
gaccttggaa ccctcctaca ttcagccccg ctctgctggt ggttaccgag ggcgataatg  180
ccaccttcac ctgtagcttc agcaacacca gcgagagctt cgtgctgaac tggtacagaa  240
tgagccccag caaccagacc gacaagctgg ccgcctttcc tgaggataga tctcagcccg  300
gccaggactg ccggttcaga gttacacagc tgcccaacgg ccgggacttc cacatgtctg  360
tcgtccgggc cagaagaaac gacagcggca catatctgtg cggcgccatt tctctggccc  420
ctaaggctca gatcaaagag agcctgagag ccgagctgag agtgacagaa agacgggccg  480
aagtgcccac agctcaccct tcaccttctc caagacctgc cggccagttt cagacactcg  540
tgggagcttg tccttgggcc gtttctggcg ctagagcctc tcctggatct gccgcttctc  600
ccagactgag agagggacct gagctgagcc ctgatgatcc tgctggactg ctggatctga  660
gacagggcat gtttgcccag ctggtggccc agaatgtgct gctgattgat ggccctctgt  720
cctggtacag cgatcctgga cttgctggcg ttagcctgac tggcggcctg agctacaaag  780
aggacaccaa agaactggtg gtggccaagg ccggcgtgta ctacgtgttc tttcagctgg  840
aactgcggag agtggtggcc ggcgaaggat ctggatctgt gtctctggct ctgcatctgc  900
agcctctgag atctgctgct ggtgctgctg ctctggccct gacagttgat ctgcctcctg  960
cctctagcga ggccagaaac tccgcctttg gcttccaagg cagactgctg cacctgagcg 1020
ctggacagag actgggagtc catctgcaca cagaagccag agctagacac gcctggcagc 1080
tgacacaagg cgctacagtg ctgggcctgt tcagagtgac ccctgagatt ccagccggcc 1140
tgccatctcc tagatctgag tgataagctt                                  1170
```

PD1-41BBL FUSION PROTEIN AND METHODS OF USE THEREOF

RELATED APPLICATIONS

This application is a continuation of U.S. patent application Ser. No. 16/475,705 filed on Jul. 3, 2019, which is a National Phase of PCT Patent Application No. PCT/IL2018/050015 having International Filing Date of Jan. 4, 2018, which claims the benefit of priority under 35 USC § 119(e) of U.S. Provisional Patent Application No. 62/442,471 filed on Jan. 5, 2017. The contents of the above applications are all incorporated by reference as if fully set forth herein in their entirety.

SEQUENCE LISTING STATEMENT

The XML file, entitled 96681AmendedSequenceListing.xml, created on Sep. 12, 2023 comprising 31,542 bytes, submitted concurrently with the filing of this application is incorporated herein by reference. The sequence listing submitted herewith is identical to the sequence listing forming part of the international application.

BACKGROUND OF THE INVENTION

Dual Signaling Proteins (DSP), also known as Signal-Converting-Proteins (SCP), which are currently known in the as bi-functional fusion proteins that link an extracellular portion of a type I membrane protein (extracellular amino-terminus), to an extracellular portion of a type II membrane protein (extracellular carboxyl-terminus), forming a fusion protein with two active sides (see for example U.S. Pat. Nos. 7,569,663 and 8,039,437, both of which are hereby incorporated by reference as if fully set forth herein).

PD1 is a surface co-inhibitory receptor of the immunoglobulin super family. PD1 is expressed on T cells, B cells, monocytes, natural killer cells, dendritic cells and many tumor-infiltrating lymphocytes (TILs). PD1 has two ligands: PDL1 (also named B7H1; CD274) and PDL2 (B7DC; CD273), that are both co-inhibitory. PDL1 is expressed on resting T cells, B cells, dendritic cells, macrophage, vascular endothelial cells and pancreatic islet cells. PDL1 is also known to be expressed in various types of cancers, especially in NSCLC, melanoma, renal cell carcinoma, gastric cancer, hepatocellular as well as cutaneous and various leukemia cancers, multiple myeloma and others. PDL2 expression is seen on macrophages and dendritic cells alone and is far less prevalent than PDL1 across tumor types. The expression of PDL1 is induced by multiple proinflammatory molecules, including types I and II IFN-7, TNF-α, LPS, GM-CSF and VEGF, as well as the cytokines IL-10 and IL-4, with IFN-7 being the most potent inducer. The tumor micro-environment upregulates PDL1 expression, thereby, promoting immune suppression. In response to immune attack, cancer cells overexpress PDL1, which binds to PD1 receptor on T cells, inhibiting the activation of T-cells, thus suppressing T-cell attack and inducing tumor immune escape. PD1/PDL1 pathway regulates immune suppression by several mechanisms:

Induce apoptosis of activated T cells
Restrain cytotoxic T lymphocytes (CTL-CD8) activity
Inhibit the proliferation of T cells
Facilitate T cell anergy and exhaustion
Enhance the function of regulatory T cells
Restrain impaired T cell activation and IL-2 production.

41BBL is the activating ligand of the 41BB receptor (CD137), a member of the TNF receptor superfamily and a potent activation-induced T cell costimulatory molecule. 41BBL naturally forms a homo-trimer but signaling via 41BB requires significant oligomerization of 41BBL. 41BBL is present on a variety of antigen presenting cells (APCs), including dendritic cells (DCs), B cells, and macrophages. The 41BB receptor is not detected (<3%) on resting T cells or T cell lines, however, 41BB is stably upregulated when T cells are activated. 41BB activation upregulates survival genes, enhances cell division, induces cytokine production and prevents activation induced cell death in T-cells.

Additional background art includes:

International Patent Application Publication No. WO2017059168;
International Patent Application Publication No. WO2001/049318;
International Patent Application Publication No. WO2016/139668;
International Patent Application Publication No. WO2014/106839;
International Patent Application Publication No. WO2012/042480;
US Patent Application Publication No. 20150183881;
US Patent Application Publication No. US20070110746;
US Patent Application Publication No. US20070036783; and
U.S. Pat. No. 9,562,087.

SUMMARY OF THE INVENTION

According to an aspect of some embodiments of the present invention there is provided a PD1-41BBL fusion protein comprising a single amino acid linker between the PD1 and the 41BBL.

According to an aspect of some embodiments of the present invention there is provided a PD1-41BBL fusion protein, wherein the PD1 amino acid is 123-166 amino acids in length.

According to an aspect of some embodiments of the present invention there is provided a PD1-41BBL fusion protein, wherein the PD1 amino acid sequence comprises SEQ ID NO: 2.

According to an aspect of some embodiments of the present invention there is provided a PD1-41BBL fusion protein in a form of at least a homo-trimer.

According to some embodiments of the invention, the at least homo-trimer is at least 100 kD in molecular weight as determined by SDS-PAGE.

According to some embodiments of the invention, the PD1-41BBL fusion protein comprises a linker between the PD1 and the 41BBL.

According to some embodiments of the invention, the linker has a length of one to six amino acids.

According to some embodiments of the invention, the linker is a single amino acid linker.

According to some embodiments of the invention, the linker is not an Fc domain of an antibody or a fragment thereof.

According to some embodiments of the invention, the linker is glycine.

According to some embodiments of the invention, the PD1 amino acid sequence is 123-166 amino acids in length.

According to some embodiments of the invention, the PD1 amino acid sequence comprises SEQ ID NO: 2.

According to some embodiments of the invention, the PD1 amino acid sequence consists of SEQ ID NO: 2.

According to some embodiments of the invention, the PD1-41BBL fusion protein being soluble.

According to some embodiments of the invention, the PD1 comprises an extracellular domain of the PD1 or a functional fragment thereof.

According to some embodiments of the invention, the 41BBL comprises an extracellular domain of the 41BBL or a functional fragment thereof.

According to some embodiments of the invention, the fusion protein is capable of at least one of:

(i) binding PD-L1 and 41BB;

(ii) activating the 41BB signaling pathway in a cell expressing the 41BB; and/or (iii) co-stimulating immune cells expressing the 41BB.

According to some embodiments of the invention, the PD1-41BBL fusion protein amino acid sequence comprises SEQ ID NO: 1.

According to some embodiments of the invention, the PD1-41BBL fusion protein amino acid sequence consists of SEQ ID NO: 1.

According to some embodiments of the invention, there is provided a polynucleotide encoding the PD1-41BBL fusion protein of the present invention.

According to some embodiments of the invention, there is provided a nucleic acid construct comprising the polynucleotide of the present invention, and a regulatory element for directing expression of the polynucleotide in a host cell.

According to some embodiments of the invention, the polynucleotide comprises SEQ ID NO: 9.

According to some embodiments of the invention, there is provided a host cell comprising the PD1-41BBL fusion protein of the present invention or the polynucleotide or the nucleic acid construct of the present invention.

According to some embodiments of the invention, there is provided a method of producing a PD1-41BBL fusion protein, the method comprising expressing in a host cell the polynucleotide or the nucleic acid construct of the present invention.

According to some embodiments of the invention, the method comprising isolating the fusion protein.

According to some embodiments of the invention, the cell is selected from the group consisting of CHO, PERC.6 and 293.

According to some embodiments of the invention, there is provided a method of treating cancer comprising administering the PD1-41BBL fusion protein of the present invention to a subject in need thereof.

According to some embodiments of the invention, there is provided a method of treating a disease that can benefit from activating immune cells comprising administering to a subject in need thereof the PD1-41BBL fusion protein of the present invention, the polynucleotide or the nucleic acid construct of the present invention or the host cell of any one of the present invention.

According to an aspect of some embodiments of the present invention there is provided an article of manufacture identified for the treatment of a disease that can benefit from activating immune cells comprising a packaging material packaging a therapeutic agent for treating the disease; and a PD1-41BBL fusion protein, a polynucleotide encoding same, a nucleic acid construct encoding same or a host cell expressing same.

According to some embodiments of the invention, the disease comprises a hyper-proliferative disease.

According to some embodiments of the invention, the hyper-proliferative disease comprises sclerosis, fibrosis, Idiopathic pulmonary fibrosis, psoriasis, systemic sclerosis/scleroderma, primary biliary cholangitis, primary sclerosing cholangitis, liver fibrosis, prevention of radiation-induced pulmonary fibrosis, myelofibrosis or retroperitoneal fibrosis.

According to some embodiments of the invention, the hyper-proliferative disease comprises cancer.

According to an aspect of some embodiments of the present invention there is provided a method of treating cancer comprising administering to a subject in need thereof an anti-cancer agent; and a PD1-41BBL fusion protein, a polynucleotide encoding same, a nucleic acid construct encoding same or a host cell expressing same.

According to some embodiments of the invention, the anti-cancer agent comprises an antibody.

According to some embodiments of the invention, the antibody is selected from the group consisting of rituximab, cetuximab, trastuzumab, edrecolomab, almetuzumab, gemtuzumab, ibritumomab, panitumumab, Belimumab, Bevacizumab, Bivatuzumab mertansine, Blinatumomab, Blontuvetmab, Brentuximab vedotin, Catumaxomab, Cixutumumab, Daclizumab, Adalimumab, Bezlotoxumab, Certolizumab pegol, Citatuzumab bogatox, Daratumumab, Dinutuximab, Elotuzumab, Ertumaxomab, Etaracizumab, Gemtuzumab ozogamicin, Girentuximab, Necitumumab, Obinutuzumab, Ofatumumab, Pertuzumab, Ramucirumab, Siltuximab, Tositumomab, Trastuzumab and ipilimumab.

According to some embodiments of the invention, the antibody is selected from the group consisting of rituximab and cetuximab.

According to some embodiments of the invention, the cancer is selected from the group consisting of lymphoma, leukemia, colon cancer, pancreatic cancer, ovarian cancer, lung cancer and squamous cell carcinoma.

According to some embodiments of the invention, cells of the cancer express PD-L1.

According to some embodiments of the invention, the disease comprises a disease associated with immune suppression or medication induced immunosuppression.

According to some embodiments of the invention, the disease comprises HIV, Measles, influenza, LCCM, RSV, Human Rhinoviruses, EBV, CMV or Parvo viruses.

According to some embodiments of the invention, the disease comprises an infection.

According to some embodiments of the invention, diseased cells of the subject express PD-L1.

According to an aspect of some embodiments of the present invention there is provided a method of activating T cells, the method comprising in-vitro activating T cells in the presence of a PD1-41BBL fusion protein and cells expressing PD-L1.

According to an aspect of some embodiments of the present invention there is provided a method of activating immune cells, the method comprising in-vitro activating immune cells in the presence of a PD1-41BBL fusion protein, a polynucleotide encoding same, a nucleic acid construct encoding same or a host cell expressing same.

According to some embodiments of the invention, the activating is in the presence of cells expressing PD-L1 or exogenous PD-L1.

According to some embodiments of the invention, the cells expressing the PD-L1 comprise cancer cells.

According to some embodiments of the invention, the method comprising adoptively transferring the immune cells following the activating to a subject in need thereof.

According to some embodiments of the invention, the subject is afflicted with a disease associated with the cells expressing the PD-L1.

According to some embodiments of the invention, the PD1-41BBL fusion protein comprises the PD1-41BBL fusion protein of the present invention, the polynucleotide or the nucleic acid construct comprises the polynucleotide or the nucleic acid construct of the present invention, and the host cell comprises the host cell of the present invention.

According to some embodiments of the invention, the immune cells comprise T cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3A demonstrates binding to PD-L1—the biosensor was pre-loaded with PD-L1:Fc and then incubated with His-tagged PD1-41BBL (SEQ ID NO: 5) or SIRPα-41BBL (SEQ ID NO: 6, as a negative control), or sPD-L1 (as a competitor). FIG. 3B demonstrates binding to 41BB—the biosensor was pre-loaded with 41BB:Fc and then incubated with His-tagged PD1-41BBL (SEQ ID NO: 5) or PD1-CD70 (SEQ ID NO: 7, as a negative control).

FIG. 9A shows histograms demonstrating expression of 41BB in HT1080-41BB cells and no expression of 41BB in HT1080-WT (HT1080) cells. FIG. 9B shows histograms demonstrating PDL1 expression in DLD1-PDL1 cells and no expression of PDL1 in DLD1-WT (DLD1). FIG. 9C is a graph demonstrating IL-8 secretion by HT1080-41BB cells when treated alone with His-tagged PD1-41BBL protein (SEQ ID NO: 5) or when treated in mixed cultures with DLD1 cells. FIG. 9D is a graph demonstrating IL8 secretion by HT1080-41BB cells when treated alone with His-tagged PD1-41BBL protein (SEQ ID NO: 5) or when treated in mixed cultures with DLD1-PDL1 cells.

FIG. 11A is a graph demonstrating IFN-γ concentration detected in the culture supernatant of human PBMCs incubated for 40 hours with different concentrations of His-tagged PD1-41BBL protein (SEQ ID NO: 5) in the presence of anti-CD3 or anti-CD3 plus IL2, as indicated. FIG. 11B is a graph demonstrating IFN-7 concentration detected in the culture supernatant of human PBMCs co-cultured with PDL1 expressing murine LivMet cells and incubated for 40 hours with different concentrations of His-tagged PD1-41BBL protein (SEQ ID NO: 5), in the presence of anti-CD3 or anti-CD3 plus IL2, as indicated.

FIG. 12A is a schematic illustration of experiment timelines: mice were inoculated S.C. with $1\times10^6$ CT-26 cells on day 0, PBS control or PD1-41BBL were injected on days 3, 7, 10, and 14. FIG. 12B show spider plots demonstrating tumor volume of the different mice in the two treatment groups. FIG. 12C is a graph demonstrating mean±standard error tumor volume in the two treatment groups.

FIG. 13A is a schematic illustration of experiment timelines: mice were inoculated I.P. with $1\times10^6$ P388 cells on day 0, PBS control, αPD1 or PD1-41BBL were injected on days 1, 3, 5, and 7. FIG. 13B is a graph demonstrating mean±standard error spleen weight in the three treatment groups upon sacrifice.

DESCRIPTION OF DETAILED EMBODIMENTS OF THE INVENTION

Figure 2C:
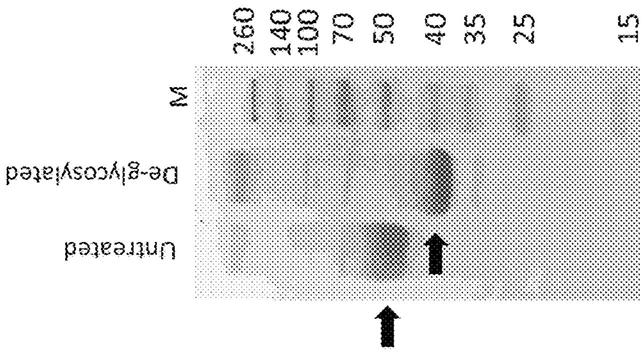
FIG. 2C is a photograph of coomassie blue staining of SDS-PAGE analysis of His-tagged PD1-41BBL (SEQ ID NO: 5) under reducing conditions treated or un-treated with de-glycosylase. His-tagged PD1-41BBL bands are marked with small black arrows.

The present invention, in some embodiments thereof, relates to a PD1-41BBL fusion protein and methods of use thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Dual Signaling Proteins (DSP), also known as Signal-Converting-Proteins (SCP), which are currently known in the art as bi-functional fusion proteins that link an extracellular portion of a type I membrane protein (extracellular amino-terminus), to an extracellular portion of a type II membrane protein (extracellular carboxyl-terminus), forming a fusion protein with two active sides.

Surprisingly, it was found that a specific fusion protein may be advantageously administered to subjects suffering from cancerous diseases, depending upon the presence of tumors that have tumor-infiltrating lymphocytes (TILs) on the tumor cells or in the tumor micro-environment as well as tumors with relatively high expression of PDL1 in the tumor micro-environment.

As is illustrated hereinunder and in the examples section, which follows, the present inventors have produced a his-tagged PD1-41BBL fusion protein (SEQ ID NO: 5) and show that the fusion protein (SEQ ID NO: 5) contains both domains and produced in the form of at least trimers (Experiments 1A-B, FIGS. 1 and 2A-2C). Following, the present inventors demonstrate that the produced his-tagged PD1-41BBL fusion protein (SEQ ID NO: 5) retains functional binding activity for its cognate receptors PD-L1 and 41BB (Experiments 1C-D, FIGS. 3A-3B, 4A-4B, 5A-5B, 6A-6B) and can trigger 41BB co-stimulation and activation of cells expressing 41BB (e.g. T cells, PBMCs) wherein presence of PD-L1 augments this activity (Experiments 2-3, 3A-B, FIGS. 7-8, 9A-9D, 10, 11A-11B). The inventors further demonstrate that the his-tagged PD1-41BBL fusion protein (SEQ ID NO: 5) is effective for the treatment of tumors as shown in in-vivo syngeneic colon carcinoma and syngeneic leukemia mouse tumor models (Experiments 4, 4A-B, FIGS. 12A-12C and 13A-13B).

Consequently, the present teachings suggest PD1-41BBL fusion proteins, polynucleotides encoding same and host cells expressing same; and uses of same in e.g. activating immune cells (via co-stimulation) in general and treating diseases that can benefit from activating immune cells (e.g. cancer) in particular.

Thus according to a first aspect of the present invention, there is provided a PD1-41BBL fusion protein or any variants or fragments thereof optionally with a linker therebetween or a PD1-41BBL fusion protein, which is at least about 70%, homologous to the sequence as set forth in SEQ ID No. 4 optionally with a linker therebetween.

According to another aspect of the present invention, there is provided a PD1-41BBL fusion protein comprising a single amino acid linker between said PD1 and said 41BBL.

According to another aspect of the present invention, there is provided a PD1-41BBL fusion protein, wherein said PD1 amino acid is 123-166 amino acids in length.

According to another aspect of the present invention, there is provided a PD1-41BBL fusion protein, wherein said PD1 amino acid sequence comprises SEQ ID NO: 2.

According to another aspect of the present invention, there is provided a PD1-41BBL fusion protein in a form of at least a homo-trimer.

According to specific embodiments, at least 10%, at least 20%, at least 30%, at least 40%, at least 50%, at least 60%, at least 70%, at least 80%, at least 90%, at least 95% of the PD1-41BBL fusion protein is in a form of at least a homo-trimer, each possibility represents a separate embodiment of the present invention.

According to specific embodiments, the at least homo-trimer comprises a homo-trimer.

According to specific embodiments, the at least homo-trimer comprises a homo-tetramer.

According to specific embodiments, the at least homo-trimer comprises a homo-pentamer.

According to specific embodiments, the at least homo-trimer comprises a homo-hexamer.

Methods of determining trimerization are well known in the art and include, but are not limited to SDS-PAGE, NATIVE-PAGE, SEC-HPLC 2D gels, gel filtration, SEC MALLS, Analytical ultracentrifugation (AUC) Mass spectrometry (MS), capillary gel electrophoresis (CGE).

According to specific embodiments the at least homo-trimer is at least 100 kD, at least 120 kD, at least 140 kD, at least 160 kD, at least 180 kD in molecular weight as determined by SDS-PAGE.

According to specific embodiments the at least homo-trimer is at least 100 kD in molecular weight as determined by SDS-PAGE.

According to specific embodiments the at least homo-trimer is at least 200 kD in molecular weight as determined by SDS-PAGE.

As used herein the term "PD1 (Programmed Death 1, also known as CD279)" refers to the polypeptide of the PDCD1 gene (Gene ID 5133) or a functional homolog e.g., functional fragment thereof. According to specific embodiments, the term "PD1" refers to a functional homolog of PD1 polypeptide. According to specific embodiments, PD1 is human PD1. According to a specific embodiment, the PD1 protein refers to the human protein, such as provided in the following GenBank Number NP_005009.

Two ligands for PD-1 have been identified, PD-L1 and PD-L2 (also known as B7-DC). According to a specific embodiment, the PD-L1 protein refers to the human protein, such as provided in the following GenBank Number NP_001254635 and NP_054862. According to a specific embodiment, the PD-L2 protein refers to the human protein, such as provided in the following GenBank Number NP_079515.

As used herein, a "functional PD1" is capable of binding its cognate ligands PD-L1 and/or PDL-2.

According to specific embodiments, a functional PD1 is capable of binding PD-L1.

As use herein, the phrase "functional homolog" or "functional fragment" when related to PD1 refers to a portion of the polypeptide which maintains the activity of the full length PD1 e.g., PD-L1 binding.

Assays for testing binding are well known in the art and include, but not limited to flow cytometry, BiaCore, bio-layer interferometry Blitz® assay, HPLC.

According to specific embodiments, the PD1 binds PD-L1 with a Kd of 1 nM-100 μM, 10-nM-10 μM, 100 nM-100 μM, 200 nM-10 μM, as determined by SPR analysis, each possibility represents a separate embodiment of the present invention.

According to specific embodiments, the PD1 binds PD-L1 with a Kd of about 270 nM as determined by SPR analysis.

According to specific embodiments, the PD1 comprises an extracellular domain of said PD1 or a functional fragment thereof.

According to specific embodiments, PD1 amino acid sequence comprises SEQ ID NO: 10.

According to specific embodiments, PD1 amino acid sequence consists of SEQ ID NO: 10.

According to specific embodiments, PD1 nucleic acid sequence comprises SEQ ID NO: 11.

According to specific embodiments, PD1 nucleic acid sequence consists of SEQ ID NO: 11.

According to specific embodiments, PD1 amino acid sequence comprises SEQ ID NO: 2.

According to specific embodiments, PD1 amino acid sequence consists of SEQ ID NO: 2.

According to specific embodiments, PD1 nucleic acid sequence comprises SEQ ID NO: 12.

According to specific embodiments, PD1 nucleic acid sequence consists of SEQ ID NO: 12.

According to specific embodiments, PD1 amino acid sequence comprises SEQ ID NO: 16 or SEQ ID NO: 17.

According to specific embodiments, PD1 amino acid sequence consists of SEQ ID NO: 16 or SEQ ID NO: 17.

The term "PD1" also encompasses functional homologues (naturally occurring or synthetically/recombinantly produced), which exhibit the desired activity (i.e., binding PD-L1 and/or PD-L2). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 2, 10, 16, or 17; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

Sequence identity or homology can be determined using any protein or nucleic acid sequence alignment algorithm such as Blast, ClustalW, and MUSCLE.

The homolog may also refer to an ortholog, a deletion, insertion, or substitution variant, including an amino acid substitution, as further described hereinbelow.

According to specific embodiments, the PD1 polypeptide may comprise conservative amino acid substitutions.

According to specific embodiments, one or more amino acid changes are located at an amino acid position selected from: V39, L40, N41, Y43, R44, M45, S48, N49, Q50, T51, D52, K53, A56, Q63, G65, Q66, V72, H82, M83, R90, Y96, L97, A100, S102, L103, A104, P105, K106, and A107 relative to the PD1 amino acid sequence set forth in SEQ ID NO: 17; or the corresponding amino acid position relative to another PD1 polypeptide.

According to specific embodiments, one or more amino acid changes are selected from the group consisting of: (1) V39H or V39R; (2) L40V or L40I; (3) N41I or N41V; (4) Y43F or Y43H; (5) R44Y or R44L; (6) M45Q, M45E, M45L, or M45D; (7) S48D, S48L, S48N, S48G, or S48V; (8) N49C, N49G, N49Y, or N49S; (9) Q50K, Q50E, or Q50H; (10) T51V, T51L, or T51A; (11) D52F, D52R, D52Y, or D52V; (12) K53T or K53L; (13) A56S or A56L; (14) Q63T, Q63I, Q63E, Q63L, or Q63P; (15) G65N, G65R, G65I, G65L, G65F, or G65V; (16) Q66P; (17) V72I; (18) H82Q; (19) M83L or M83F; (20) R90K; (21) Y96F; (22) L97Y, L97V, or L97I; (23) A100I or A100V; (24) S102T or S102A; (25) L103I, L103Y, or L103F; (26) A104S, A104H, or A104D; (27) P105A; (28) K106G, K106E, K106I, K106V, K106R, or K106T; and (29) A107P, A107I, or A107V relative to the PD1 amino acid sequence set forth in SEQ ID NO: 17; or a change that results in the same amino acid at the corresponding amino acid position relative to another PD1 polypeptide.

Additional description on conservative amino acid and non-conservative amino acid substitutions is further provided hereinbelow.

According to specific embodiments, PD1 amino acid sequence comprises 100-200 amino acids, 120-180 amino acids, 120-160, 130-170 amino acids, 130-160, 130-150, 140-160 amino acids, 145-155 amino acids, each possibility represents a separate embodiment of the present invention.

According to specific embodiments, PD1 amino acid sequence is 123-166 amino acids in length.

According to specific embodiments, PD1 amino acid sequence is 145-155 amino acids in length.

According to specific embodiments, PD1 amino acid sequence is 150 amino acids in length.

As used herein the term "41BBL (also known as CD137L and TNFSF9)" refers to the polypeptide of the TNFSF9 gene (Gene ID 8744) or a functional homolog e.g., functional fragment thereof. According to specific embodiments, the term "41BBL" refers to a functional homolog of 41BBL polypeptide. According to specific embodiments, 41BBL is human 41BBL. According to a specific embodiment, the 41BBL protein refers to the human protein, such as provided in the following GenBank Number NP_003802.

According to specific embodiments, the 41BBL comprises an extracellular domain of said 41BBL or a functional fragment thereof.

According to specific embodiments, 41BBL amino acid sequence comprises SEQ ID NO: 13.

According to specific embodiments, 41BBL amino acid sequence consists of SEQ ID NO: 13.

According to specific embodiments, 41BBL nucleic acid sequence comprises SEQ ID NO: 14.

According to specific embodiments, 41BBL nucleic acid sequence consists of SEQ ID NO: 14.

According to specific embodiments, 41BBL amino acid sequence comprises SEQ ID NO: 3.

According to specific embodiments, 41BBL amino acid sequence consists of SEQ ID NO: 3.

According to specific embodiments, 41BBL nucleic acid sequence comprises SEQ ID NO: 15.

According to specific embodiments, 41BBL nucleic acid sequence consists of SEQ ID NO: 15.

The term "41BBL" also encompasses functional homologues (naturally occurring or synthetically/recombinantly produced), which exhibit the desired activity (as defined hereinbelow). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 3, 13; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

According to specific embodiments, the 41BBL polypeptide may comprise conservative amino acid substitutions, as further described hereinbelow.

According to specific embodiments, 41BBL amino acid sequence comprises 100-300 amino acids, 150-250 amino acids, 100-250 amino acids, 150-220 amino acids, 180-220 amino acids, 190-210 amino acids, each possibility represents a separate embodiment of the present invention.

According to specific embodiments, 41BBL amino acid sequence is 190-210 amino acids in length.

According to specific embodiments, 41BBL amino acid sequence is 204 amino acids in length.

As used herein, a "functional 41BBL" is capable of least one of:

(i) binding its cognate receptor 41BB (also known as CD137), (ii) activating 41BB signaling pathway in an immune cell expressing 41BB; and/or (iii) activating immune cells expressing said 41BB.

According to specific embodiments, functional 41BBL is capable of (i), (ii), (iii), (i)+(ii), (i)+(iii), (ii)+(iii).

According to specific embodiments, functional 41BBL is capable of (i)+(ii)+(iii).

As use herein, the phrase "functional homolog" or "functional fragment" when related to 41BBL, refers to a portion of the polypeptide which maintains the activity of the full length 41BBL e.g., binding 41BB, activating 41BB signaling pathway, activating immune cells expressing 41BB.

According to a specific embodiment, the 41BB protein refers to the human protein, such as provided in the following GenBank Number NP_001552.

Assays for testing binding are well known in the art and are further described hereinabove.

According to specific embodiments, the SIRPα binds CD47 with a Kd of 0.1-100 μM, 0.1-10 μM, 1-10 μM, 0.1-5 μM, or 1-2 μM as determined by SPR, each possibility represented a separate embodiment of the present invention.

According to specific embodiments, the 41BBL binds 41BB with a Kd of about 55.2 nM as determined by SPR.

As used herein the terms "activating" or "activation" refer to the process of stimulating an immune cell (e.g. T cell, B cell, NK cell, dendritic cell) that results in cellular proliferation, maturation, cytokine production, phagocytosis and/or induction of regulatory or effector functions.

According to specific embodiments, activating comprises co-stimulating.

As used herein the term "co-stimulating" or "co-stimulation" refers to transmitting a secondary antigen independent stimulatory signal (e.g. 41BB signal) resulting in activation of the immune cell.

According to specific embodiments, activating comprises suppressing an inhibitory signal (e.g. PD1 signal) resulting in activation of the immune cell.

Methods of determining signaling of a stimulatory or inhibitory signal are well known in the art and also disclosed in the Examples section which follows, and include, but are not limited to, binding assay using e.g. BiaCore, HPLC or flow cytometry, enzymatic activity assays such as kinase activity assays, and expression of molecules involved in the signaling cascade using e.g. PCR, Western blot, immunoprecipitation and immunohistochemistry. Additionally or alternatively, determining transmission of a signal (co-stimulatory or inhibitory) can be effected by evaluating immune cell activation or function. Methods of evaluating immune cell activation or function are well known in the art and include, but are not limited to, proliferation assays such as CFSE staining, MTS, Alamar blue, BRDU and thymidine incorporation, cytotoxicity assays such as CFSE staining, chromium release, Calcin AM, cytokine secretion assays such as intracellular cytokine staining ELISPOT and ELISA, expression of activation markers such as CD25, CD69, CD137, CD107a, PD1, and CD62L using flow cytometry.

According to specific embodiments, determining the signaling activity or activation is effected in-vitro or ex-vivo e.g. in a mixed lymphocyte reaction (MLR), as further described hereinbelow.

For the same culture conditions the signaling activity or the immune cell activation or function are generally expressed in comparison to the signaling, activation or function in a cell of the same species but not contacted with the PD1-41BBL fusion protein, a polynucleotide encoding same or a host cell encoding same; or contacted with a vehicle control, also referred to as control. The terms "DSP" and "fusion protein", "chimeric protein" or "chimera" are used herein interchangeably, and refer to an amino acid sequence having two or more parts which are not found together in a single amino acid sequence in nature.

In one embodiment, the present invention is directed to a fusion protein comprising a PD1-41BBL, (hereinafter, PD1-41BBL fusion protein) or any variants or fragments thereof optionally with a linker therebetween.

PD1-41BBL is a Dual Signaling Protein (DSP) chimera protein fusing the extracellular domains of two different human membrane proteins. The N terminal domain is the extracellular domain of the human PD1 (gene: PDCD1), which is a type 1 membrane protein, and the C terminal domain of the chimera is the extracellular domain of the human 41BBL (gene: TNFSF9), which is a type 2 membrane protein.

According to specific embodiments, the PD1-41BBL fusion protein is soluble (i.e., not immobilized to a synthetic or a naturally occurring surface).

According to specific embodiments, the PD1-41BBL fusion protein is immobilized to a synthetic or a naturally occurring surface.

According to specific embodiments, the PD1-41BBL does not comprise a linker between the PD1 and the 41BBL.

In some embodiments, the PD1-41BBL comprises a linker which may be at any length.

Hence, according to specific embodiments the PD1-41BBL fusion protein comprises a linker between said PD1 and said 41BBL.

Any linker known in the art can be used with specific embodiments of the invention.

According to specific embodiments, the linker may be derived from naturally-occurring multi-domain proteins or is an empirical linker as described, for example, in Chichili et al., (2013), Protein Sci. 22(2): 153-167, Chen et al, (2013), Adv Drug Deliv Rev. 65(10): 1357-1369, the entire contents of which are hereby incorporated by reference. In some embodiments, the linker may be designed using linker designing databases and computer programs such as those described in Chen et al., (2013), Adv Drug Deliv Rev. 65(10): 1357-1369 and Crasto et al., (2000), Protein Eng. 13(5):309-312, the entire contents of which are hereby incorporated by reference.

According to specific embodiments, the linker is a synthetic linker such as PEG.

According to specific embodiments, the linker is an Fc domain or the hinge region of an antibody (e.g., of IgG, IgA, IgD or IgE) or a fragment thereof.

According to other specific embodiments, the linker is not an Fc domain or a hinge region of an antibody or a fragment thereof.

According to specific embodiments, the linker may be functional. For example, without limitation, the linker may function to improve the folding and/or stability, improve the expression, improve the pharmacokinetics, and/or improve the bioactivity of the PD1-41BBL fusion protein.

In another example, the linker may function to target the PD1-41BBL fusion protein to a particular cell type or location.

According to specific embodiments, the linker is a polypeptide.

In some embodiments, the PD1-41BBL fusion protein comprises a linker at a length of one to six amino acids.

According to specific embodiments, the linker is substantially comprised of glycine and/or serine residues (e.g. about 30%, or about 40%, or about 50%, or about 60%, or about 70%, or about 80%, or about 90%, or about 95%, or about 97% or 100% glycines and serines).

According to specific embodiments, the linker is a single amino acid linker.

In some embodiments of the invention, the one amino acid which links PD1 and 41BBL is glycine, also referred to herein as PD1-G-41BBL fusion protein.

According to specific embodiments, the PD1-41BBL fusion protein amino acid sequence comprises SEQ ID NO: 1.

According to specific embodiments, the PD1-41BBL fusion protein amino acid sequence consists of SEQ ID NO: 1.

In some embodiments the term "PD1-G-41BBL fusion protein" refers to a protein identified by SEQ ID NO. 1:

Amino-acid sequence of the chimera protein (PD1-G-41BBL):

PGWFLDSPDRPWNPPTFSPALLVVTEGDNATFTCSFSNTSESFVLNWYR

MSPSNQTDKLAAFPEDRSQPGQDCRFRVTQLPNGRDFHMSVVRARRNDS

GTYLCGAISLAPKAQIKESLRAELRVTERRAEVPTAHPSPSPRPAGQFQ

-continued

TLV*G*ACPWAVSGARASPGSAASPRLREGPELSPDDPAGLLDLRQGMFAQ

LVAQNVLLIDGPLSWYSDPGLAGVSLTGGLSYKEDTKELVVAKAGVYYV

FFQLELRRVVAGEGSGSVSLALHLQPLRSAAGAAALALTVDLPPASSEA

RNSAFGFQGRLLHLSAGQRLGVHLHTEARARHAWQLTQGATVLGLFRVT

PEIPAGLPSPRSE

The extracellular domain of the human PD1 protein is underlined i.e.

(SEQ ID NO. 2)

PGWFLDSPDRPWNPPTFSPALLVVTEGDNATFTCSFSNTSESFVLNWYR

MSPSNQTDKLAAFPEDRSQPGQDCRFRVTQLPNGRDFHMSVVRARRNDS

GTYLCGAISLAPKAQIKESLRAELRVTERRAEVPTAHPSPSPRPAGQFQ

TLV

The extracellular domain of the human 41BBL is bold i.e.

(SEQ ID NO. 3)

ACPWAVSGARASPGSAASPRLREGPELSPDDPAGLLDLRQGMFAQLVAQ

NVLLIDGPLSWYSDPGLAGVSLTGGLSYKEDTKELVVAKAGVYYVFFQL

ELRRVVAGEGSGSVSLALHLQPLRSAAGAAALALTVDLPPASSEARNSA

FGFQGRLLHLSAGQRLGVHLHTEARARHAWQLTQGATVLGLFRVTPEIP

AGLPSPRS

According to specific embodiments, the amino acid sequence of PD1-G-41BBL is at least about 70%, 75%, 80%, 85%, 90%, 95%, 96%, 97%, 98% or 99% homologous to the amino acid sequence as set forth in SEQ ID No. 1 or to the polynucleotide sequence encoding same.

In additional embodiments, the PD1-G-41BBL fusion protein may be a functional fragment, variant and/or derivative of the amino acid sequence shown in SEQ ID NO. 1. A number of such variants are known in the art, see as for example in Young Won, et al, 2010; Rabu, et al, 2005; Maute, et al, 2015; and Parry, et al, 2005, hereby incorporated by reference as if fully set forth herein.

In some embodiments, there is provided a PD1-41BBL fusion protein which is at least about 70%, 75%, 80%, 85%, 90%, 95%, 96%, 97%, 98% or 99% homologous to the sequence as set forth in SEQ ID No. 4 optionally with a linker between PD1 peptide or the ECD thereof and 41BBL peptide or the ECD thereof, wherein SEQ ID No. 4 is:

PGWFLDSPDRPWNPPTESPALLVVTEGDNATFTCSESNTSESFVLNWYR

MSPSNQTDKLAAFPEDRSQPGQDCRFRVTQLPNGRDFHMSVVRARRNDS

GTYLCGAISLAPKAQIKESLRAELRVTERRAEVPTAHPSPSPRPAGQFQ

TLVACPWAVSGARASPGSAASPRLREGPELSPDDPAGLLDLRQGMFAQL

VAQNVLLIDGPLSWYSDPGLAGVSLTGGLSYKEDTKELVVAKAGVYYVF

FQLELRRVVAGEGSGSVSLALHLQPLRSAAGAAALALTVDLPPASSEAR

NSAFGFQGRLLHLSAGQRLGVHLHTEARARHAWQLTQGATVLGLFRVTP

EIPAGLPSPRSE

In some embodiments, there is provided a PD1-4-1BBL as set forth in SEQ ID No. 4 optionally with a linker between PD1 peptide or the ECD thereof and 41BBL peptide or the ECD thereof, wherein SEQ ID No. 4 is:

```
PGWFLDSPDRPWNPPTESPALLVVTEGDNATFTCSESNTSESFVLNWYR
MSPSNQTDKLAAFPEDRSQPGQDCRFRVTQLPNGRDFHMSVVRARRNDS
GTYLCGAISLAPKAQIKESLRAELRVTERRAEVPTAHPSPSPRPAGQFQ
TLVACPWAVSGARASPGSAASPRLREGPELSPDDPAGLLDLRQGMFAQL
VAQNVLLIDGPLSWYSDPGLAGVSLTGGLSYKEDTKELVVAKAGVYYVF
FQLELRRVVAGEGSGSVSLALHLQPLRSAAGAAALALTVDLPPASSEAR
NSAFGFQGRLLHLSAGQRLGVHLHTEARARHAWQLTQGATVLGLFRVTP
EIPAGLPSPRSE
```

According to specific embodiments, the PD1-41BBL fusion protein is capable of least one of:

(i) binding PD-L1 AND 41BB, (ii) activating 41BB signaling pathway in an immune cell (e.g. T cell) expressing 41BB; and/or (iii) activating immune cells (e.g. T cells) expressing said 41BB.

According to specific embodiments, the PD1-41BBL fusion protein is capable of (i), (ii), (iii), (i)+(ii), (i)+(iii), (ii)+(iii).

According to specific embodiments, the PD1-41BBL fusion protein is capable of (i)+(ii)+(iii).

Methods of determining binding, activating 41BB signaling pathway and activating immune cells are well known in the art and are further described hereinabove and in the Examples section which follows.

As the compositions of some embodiments of present invention (e.g. the fusion protein, a polynucleotide or nucleic acid encoding same or a host cell expressing same) are capable of activating immune cells, they can be used in method of activating immune cells, in-vitro, ex-vivo and/or in-vivo.

Thus, according to an aspect of the present invention, there is provided a method of activating immune cells, the method comprising in-vitro or ex-vivo activating immune cells in the presence of a PD1-41BBL fusion protein, a polynucleotide encoding same, a nucleic acid construct encoding same or a host cell expressing same.

According to another aspect of the present invention, there is provided a method of activating T cells, the method comprising in-vitro or ex-vivo activating T cells in the presence of a PD1-41BBL fusion protein and cells expressing PD-L1.

According to specific embodiments, the immune cells express 41BB.

According to specific embodiments, the immune cells comprise peripheral mononuclear blood cells (PBMCs).

As used herein the term "peripheral mononuclear blood cells (PBMCs)" refers to a blood cell having a single nucleus and includes lymphocytes, monocytes and dendritic cells (DCs).

According to specific embodiments, the PBMCs are selected from the group consisting of dendritic cells (DCs), T cells, B cells, NK cells and NKT cells.

According to specific embodiments, the PBMCs comprise T cells, B cells, NK cells and NKT cells.

Methods of obtaining PBMCs are well known in the art, such as drawing whole blood from a subject and collection in a container containing an anti-coagulant (e.g. heparin or citrate); and apheresis. Following, according to specific embodiments, at least one type of PBMCs is purified from the peripheral blood. There are several methods and reagents known to those skilled in the art for purifying PBMCs from whole blood such as leukapheresis, sedimentation, density gradient centrifugation (e.g. ficoll), centrifugal elutriation, fractionation, chemical lysis of e.g. red blood cells (e.g. by ACK), selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g. killing) with specific antibodies or by affinity based purification based on negative selection (using e.g. magnetic cell separation techniques, FACS sorter and/or capture ELISA labeling). Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiments, the immune cells comprise tumor infiltrating lymphocytes.

As used herein the term "tumor infiltrating lymphocytes (TILs) refers to mononuclear white blood cells that have lest the bloodstream and migrated into a tumor.

According to specific embodiments, the TILs are selected from the group consisting of T cells, B cells, NK cells and monocytes.

Methods of obtaining TILs are well known in the art, such as obtaining tumor samples from a subject by e.g. biopsy or necropsy and preparing a single cell suspension thereof. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Following, the at least one type of TILs can be purified from the cell suspension. There are several methods and reagents known to those skilled in the art for purifying the desired type of TILs, such as selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g. killing) with specific antibodies or by affinity based purification based on negative selection (using e.g. magnetic cell separation techniques, FACS sorter and/or capture ELISA labeling). Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiments, the immune cells comprise phagocytic cells.

As used herein, the term "phagocytic cells" refer to a cell that is capable of phagocytosis and include both professional and non-professional phagocytic cells. Methods of analyzing phagocytosis are well known in the art and include for examples killing assays, flow cytometry and/or microscopic evaluation (live cell imaging, fluorescence microscopy, confocal microscopy, electron microscopy). According to specific embodiments, the phagocytic cells are selected from the group consisting of monocytes, dendritic cells (DCs) and granulocytes.

According to specific embodiments, the immune cells comprise monocytes.

According to specific embodiments, the term "monocytes" refers to both circulating monocytes and to macrophages (also referred to as mononuclear phagocytes) present in a tissue.

According to specific embodiments, the monocytes comprise macrophages. Typically, cell surface phenotype of macrophages include CD14, CD40, CD11b, CD64, F4/80 (mice)/EMR1 (human), lysozyme M, MAC-1/MAC-3 and CD68.

According to specific embodiments, the monocytes comprise circulating monocytes. Typically, cell surface phenotypes of circulating monocytes include CD14 and CD16 (e.g. CD14++CD16−, CD14+CD16++, CD14++CD16+).

According to specific embodiments, the immune cells comprise DCs

As used herein the term "dendritic cells (DCs)" refers to any member of a diverse population of morphologically similar cell types found in lymphoid or non-lymphoid tissues. DCs are a class of professional antigen presenting cells, and have a high capacity for sensitizing HLA-restricted T cells. DCs include, for example, plasmacytoid dendritic cells, myeloid dendritic cells (including immature and mature dendritic cells), Langerhans cells, interdigitating cells, follicular dendritic cells. Dendritic cells may be recognized by function, or by phenotype, particularly by cell surface phenotype. These cells are characterized by their distinctive morphology having veil-like projections on the cell surface, intermediate to high levels of surface HLA-class II expression and ability to present antigen to T cells, particularly to naive T cells (See Steinman R, et al., Ann. Rev. Immunol. 1991; 9:271-196). Typically, cell surface phenotype of DCs include CD1a+, CD4+, CD86+, or HLA-DR. The term DCs encompasses both immature and mature DCs.

According to specific embodiments, the immune cells comprise granulocytes.

As used herein, the term "granulocytes" refer to polymorphonuclear leukocytes characterized by the presence of granules in their cytoplasm.

According to specific embodiments, the granulocytes comprise neutrophils.

According to specific embodiments, the granulocytes comprise mast-cells.

According to specific embodiments the immune cells comprise T cells.

As used herein, the term "T cells" refers to a differentiated lymphocyte with a CD3+, T cell receptor (TCR)+ having either CD4+ or CD8+ phenotype. The T cell may be either an effector or a regulatory T cell.

As used herein, the term "effector T cells" refers to a T cell that activates or directs other immune cells e.g. by producing cytokines or has a cytotoxic activity e.g., CD4+, Th1/Th2, CD8+ cytotoxic T lymphocyte.

As used herein, the term "regulatory T cell" or "Treg" refers to a T cell that negatively regulates the activation of other T cells, including effector T cells, as well as innate immune system cells.

Treg cells are characterized by sustained suppression of effector T cell responses. According to a specific embodiment, the Treg is a CD4+CD25+Foxp3+ T cell.

According to specific embodiments, the T cells are CD4+ T cells.

According to other specific embodiments, the T cells are CD8+ T cells.

According to specific embodiments, the T cells are memory T cells. Non-limiting examples of memory T cells include effector memory CD4+ T cells with a CD3+/CD4+/CD45RA−/CCR7− phenotype, central memory CD4+ T cells with a CD3+/CD4+/CD45RA−/CCR7+ phenotype, effector memory CD8+ T cells with a CD3+/CD8+ CD45RA−/CCR7− phenotype and central memory CD8+ T cells with a CD3+/CD8+CD45RA−/CCR7+ phenotype.

According to specific embodiments, the T cells comprise engineered T cells transduced with a nucleic acid sequence encoding an expression product of interest.

According to specific embodiments, the expression product of interest is a T cell receptor (TCR) or a chimeric antigen receptor (CAR).

As used herein the phrase "transduced with a nucleic acid sequence encoding a TCR" or "transducing with a nucleic acid sequence encoding a TCR" refers to cloning of variable α- and β-chains from T cells with specificity against a desired antigen presented in the context of MHC. Methods of transducing with a TCR are known in the art and are disclosed e.g. in Nicholson et al. Adv Hematol. 2012; 2012:404081; Wang and Riviere Cancer Gene Ther. 2015 March; 22(2):85-94); and Lamers et al, Cancer Gene Therapy (2002) 9, 613-623.

As used herein, the phrase "transduced with a nucleic acid sequence encoding a CAR" or "transducing with a nucleic acid sequence encoding a CAR" refers to cloning of a nucleic acid sequence encoding a chimeric antigen receptor (CAR), wherein the CAR comprises an antigen recognition moiety and a T-cell activation moiety. A chimeric antigen receptor (CAR) is an artificially constructed hybrid protein or polypeptide containing an antigen binding domain of an antibody (e.g., a single chain variable fragment (scFv)) linked to T-cell signaling or T-cell activation domains. Method of transducing with a CAR are known in the art and are disclosed e.g. in Davila et al. Oncoimmunology. 2012 Dec. 1; 1(9):1577-1583; Wang and Riviere Cancer Gene Ther. 2015 March; 22(2):85-94); Maus et al. Blood. 2014 Apr. 24; 123(17):2625-35; Porter DL The New England journal of medicine. 2011, 365(8):725-733; Jackson H J, Nat Rev Clin Oncol. 2016; 13(6):370-383; and Globerson-Levin et al. Mol Ther. 2014; 22(5):1029-1038.

According to specific embodiments, the immune cells comprise B cells.

As used herein the term "B cells" refers to a lymphocyte with a B cell receptor (BCR)+, CD19+ and or B220+ phenotype. B cells are characterized by their ability to bind a specific antigen and elicit a humoral response.

According to specific embodiments, the immune cells comprise NK cells.

As used herein the term "NK cells" refers to differentiated lymphocytes with a CD16+CD56+ and/or CD57+ TCR− phenotype. NK are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

According to specific embodiments, the immune cells comprise NKT cells.

As used herein the term "NKT cells" refers to a specialized population of T cells that express a semi-invariant ap T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD1d. NKT cells can have either protective or deleterious effects due to their abilities to produce cytokines that promote either inflammation or immune tolerance.

According to specific embodiments, the immune cells are obtained from a healthy subject.

According to specific embodiments, the immune cells are obtained from a subject suffering from a pathology.

According to specific embodiments, the activating is in the presence of cells expressing PD-L1 or exogenous PD-L1.

According to specific embodiments, the activating is in the presence of exogenous PD-L1, According to specific embodiments, the exogenous PD-L1 is soluble.

According to other specific embodiments, the exogenous PD-L1 is immobilized to a solid support.

According to specific embodiments, the activating is in the presence of cells expressing PD-L1.

According to specific embodiments, the cells expressing the PD-L1 comprise pathologic (diseased) cells.

According to specific embodiments, the cells expressing the PD-L1 comprise cancer cells.

According to specific embodiments, the activating is in the presence of a stimulatory agent capable of at least transmitting a primary activating signal [e.g. ligation of the T-Cell Receptor (TCR) with the Major Histocompatibility Complex (MHC)/peptide complex on the Antigen Presenting Cell (APC)] resulting in cellular proliferation, maturation, cytokine production, phagocytosis and/or induction of regulatory or effector functions of the immune cell. According to specific embodiments, the stimulator agent can also transmit a secondary co-stimulatory signal.

Methods of determining the amount of the stimulatory agent and the ratio between the stimulatory agent and the immune cells are well within the capabilities of the skilled in the art and thus are not specified herein.

The stimulatory agent can activate the immune cells in an antigen-dependent or -independent (i.e. polyclonal) manner.

According to specific embodiments, stimulatory agent comprises an antigen non-specific stimulator.

Non-specific stimulator are known to the skilled in the art. Thus, as a non-limiting example, when the immune cells comprise T cells, antigen non-specific stimulator can be an agent capable of binding to a T cell surface structure and induce the polyclonal stimulation of the T cell, such as but not limited to anti-CD3 antibody in combination with a co-stimulatory protein such as anti-CD28 antibody. Other non-limiting examples include anti-CD2, anti-CD137, anti-CD134, Notch-ligands, e.g. Delta-like 1/4, Jagged1/2 either alone or in various combinations with anti-CD3. Other agents that can induce polyclonal stimulation of T cells include, but not limited to mitogens, PHA, PMA-ionomycin, CEB and CytoStim (Miltenyi Biotech). According to specific embodiments, the antigen non-specific stimulator comprises anti-CD3 and anti-CD28 antibodies. According to specific embodiments, the T cell stimulator comprises anti-CD3 and anti-CD28 coated beads, such as the CD3CD28 MACSiBeads obtained from Miltenyi Biotec.

According to specific embodiments, the stimulatory agent comprises an antigen-specific stimulator.

Non-limiting examples of antigen specific T cell stimulators include an antigen-loaded antigen presenting cell [APC, e.g. dendritic cell] and peptide loaded recombinant MHC. Thus, for example, a T cells stimulator can be a dendritic cell preloaded with a desired antigen (e.g. a tumor antigen) or transfected with mRNA coding for the desired antigen.

According to specific embodiments, the antigen is a cancer antigen.

As used herein, the term "cancer antigen" refers to an antigen is overexpressed or solely expressed by a cancerous cell as compared to a non-cancerous cell. A cancer antigen may be a known cancer antigen or a new specific antigen that develops in a cancer cell (i.e. neoantigens).

Non-limiting examples for known cancer antigens include MAGE-AI, MAGE-A2, MAGE-A3, MAGE-A4, MAGE-AS, MAGE-A6, MAGE-A7, MAGE-AS, MAGE-A9, MAGE-AIO, MAGE-All, MAGE-A12, GAGE-I, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), MAGE-Cl/CT7, MAGE-C2, NY-ESO-1, LAGE-1, SSX-1, SSX-2(HOM-MEL-40), SSX-3, SSX-4, SSX-5, SCP-1 and XAGE, melanocyte differentiation antigens, p53, ras, CEA, MUCI, PMSA, PSA, tyrosinase, Melan-A, MART-I, gplOO, gp75, alphaactinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-All, hsp70-2, KIAA0205, Mart2, Mum-2, and 3, neo-PAP, myosin class I, OS-9, pml-RAR alpha fusion protein, PTPRK, K-ras, N-ras, Triosephosphate isomerase, GnTV, Herv-K-mel, NA-88, SP17, and TRP2-Int2, (MART-I), E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, plSOerbB-3, c-met, nm-23H1, PSA, TAG-72-4, CA 19-9, CA 72-4, CAM 17.1, NuMa, K-ras, alpha.-fetoprotein, 13HCG, BCA225, BTAA, CA 125, CA 15-3 (CA 27.29\BCAA), CA 195, CA 242, CA-50, CAM43, CD68\KP1, C0-029, FGF-5, 0250, Ga733 (EpCAM), HTgp-175, M344, MA-50, MG7-Ag, MOV18, NB\170K, NYCO-I, RCASI, SDCCAG16, TA-90 (Mac-2 binding protein\cyclophilin C-associated protein), TAAL6, TAG72, TLP, TPS, tyrosinase related proteins, TRP-1, or TRP-2.

Other tumor antigens that may be expressed are well-known in the art (see for example WO00/20581; Cancer Vaccines and Immunotherapy (2000) Eds Stern, Beverley and Carroll, Cambridge University Press, Cambridge). The sequences of these tumor antigens are readily available from public databases but are also found in WO 1992/020356 A1, WO 1994/005304 A1, WO 1994/023031 A1, WO 1995/020974 A1, WO 1995/023874 A1 & WO 1996/026214 A1.

Alternatively, or additionally, a tumor antigen may be identified using cancer cells obtained from the subject by e.g. biopsy.

Thus, according to specific embodiments, the stimulatory agent comprises a cancer cell.

According to specific embodiments, the activating is in the presence of an anti-cancer agent.

According to specific embodiments, the immune cells are purified following the activation.

Thus, the present invention also contemplated isolated immune cells obtainable according to the methods of the present invention.

According to specific embodiments, the immune cells used and/or obtained according to the present invention can be freshly isolated, stored e.g., cryopreserved (i.e. frozen) at e.g. liquid nitrogen temperature at any stage for long periods of time (e.g., months, years) for future use; and cell lines.

Methods of cryopreservation are commonly known by one of ordinary skill in the art and are disclosed e.g. in International Patent Application Publication Nos.

WO2007054160 and WO 2001039594 and US Patent Application Publication No. US20120149108.

According to specific embodiments, the cells obtained according to the present invention can be stored in a cell bank or a depository or storage facility.

Consequently, the present teachings further suggest the use of the isolated immune cells and the methods of the present invention as, but not limited to, a source for adoptive immune cells therapies for diseases that can benefit from activating immune cells e.g. a hyper-proliferative disease; a disease associated with immune suppression and infections.

Thus, according to specific embodiments, method of the present invention comprise adoptively transferring the immune cells following said activating to a subject in need thereof.

According to specific embodiments, there is provided the immune cells obtainable according to the methods of the present invention are for use in adoptive cell therapy.

The cells used according to specific embodiments of the present invention may be autologous or non-autologous; they can be syngeneic or non-syngeneic: allogeneic or xenogeneic to the subject; each possibility represents a separate embodiment of the present invention.

The present teachings also contemplates the use of the compositions of the present invention (e.g. the fusion protein, a polynucleotide or nucleic acid construct encoding same or a host cell expressing same) in methods of treating a disease that can benefit from activating immune cells.

Thus, according to another aspect of the present invention, there is provided a method of treating a disease that can benefit from activating immune cells comprising administering to a subject in need thereof the PD1-41BBL fusion protein, a polynucleotide or nucleic acid construct encoding same or a host cell encoding same.

According to another aspect of the present invention, there is provided the PD1-41BBL fusion protein, a polynucleotide or nucleic acid construct encoding same or a host cell encoding same for use in the treatment of a disease that can benefit from activating immune cells.

The term "treating" or "treatment" refers to inhibiting, preventing or arresting the development of a pathology (disease, disorder or medical condition) and/or causing the reduction, remission, or regression of a pathology or a symptom of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, e.g., human beings at any age and of any gender. According to specific embodiments, the term "subject" refers to a subject who suffers from the pathology (disease, disorder or medical condition). According to specific embodiments, this term encompasses individuals who are at risk to develop the pathology.

According to specific embodiments, the subject is afflicted with a disease associated with cells expressing PD-L1.

According to specific embodiments, diseases cells of the subject express PD-L1.

As used herein the phrase "a disease that can benefit from activating immune cells" refers to diseases in which the subject's immune response activity may be sufficient to at least ameliorate symptoms of the disease or delay onset of symptoms, however for any reason the activity of the subject's immune response in doing so is less than optimal.

Non-limiting examples of diseases that can benefit from activating immune cells include hyper-proliferative diseases, diseases associated with immune suppression, immunosuppression caused by medication (e.g. mTOR inhibitors, calcineurin inhibitor, steroids) and infections.

According to specific embodiments, the disease comprises a hyper-proliferative disease.

According to specific embodiments, the hyper-proliferative disease comprises sclerosis, fibrosis, Idiopathic pulmonary fibrosis, psoriasis, systemic sclerosis/scleroderma, primary biliary cholangitis, primary sclerosing cholangitis, liver fibrosis, prevention of radiation-induced pulmonary fibrosis, myelofibrosis or retroperitoneal fibrosis.

According to other specific embodiments, the hyper-proliferative disease comprises cancer.

Thus, according to another aspect of the present invention, there is provided a method of treating cancer comprising administering the PD1-41BBL fusion protein to a subject in need thereof.

As used herein, the term cancer encompasses both malignant and pre-malignant cancers.

With regard to pre-malignant or benign forms of cancer, optionally the compositions and methods thereof may be applied for halting the progression of the pre-malignant cancer to a malignant form.

Cancers which can be treated by the methods of some embodiments of the invention can be any solid or non-solid cancer and/or cancer metastasis.

According to specific embodiments, the cancer comprises malignant cancer.

Cancers which can be treated by the methods of some embodiments of the invention can be any solid or non-solid cancer and/or cancer metastasis. Examples of cancer include but are not limited to, carcinoma, lymphoma, blastoma, sarcoma, and leukemia. More particular examples of such cancers include squamous cell cancer, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; Burkitt lymphoma, Diffused large B cell lymphoma (DLBCL), high grade lymphoblastic NHL; high-grade small non-cleaved cell NHL; bulky disease NHL; mantle cell lymphoma; AIDS-related lymphoma; and Waldenstrom's Macroglobulinemia); T cell lymphoma, Hodgkin lymphoma, chronic lymphocytic leukemia (CLL); acute lymphoblastic leukemia (ALL); Acute myeloid leukemia (AML), Acute promyelocytic leukemia (APL), Hairy cell leukemia; chronic myeloblastic leukemia (CML); and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amenable for treatment of the invention include metastatic cancers.

According to specific embodiments, the cancer comprises pre-malignant cancer.

Pre-malignant cancers (or pre-cancers) are well characterized and known in the art (refer, for example, to Berman J J. and Henson D E., 2003. Classifying the precancers: a metadata approach. BMC Med Inform Decis Mak. 3:8). Classes of pre-malignant cancers amenable to treatment via the method of the invention include acquired small or microscopic pre-malignant cancers, acquired large lesions with nuclear atypia, precursor lesions occurring with inherited hyperplastic syndromes that progress to cancer, and acquired diffuse hyperplasias and diffuse metaplasias. Examples of small or microscopic pre-malignant cancers include HGSIL (High grade squamous intraepithelial lesion of uterine cervix), AlN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

In some embodiments of the invention, the diseases to be treated by a fusion protein comprising PD1 or the ECD thereof and 41BBL or ECD thereof, such as for example, PD1-G-41BBL are: Acute Myeloid Leukemia, Anal Cancer, Basal Cell Carcinoma, B-Cell Non-Hodgkin Lymphoma, Bile Duct Cancer, Bladder Cancer, Breast Cancer, Cervical Cancer, Chronic Lymphocytic Leukemia (CLL), Chronic Myelocytic Leukemia (CML), Colorectal Cancer, Cutaneous T-Cell Lymphoma, Diffuse Large B-Cell Lymphoma, Endometrial Cancer, Esophageal Cancer, Fallopian Tube Cancer, Follicular Lymphoma, Gastric Cancer, Gastroesophageal (GE) Junction Carcinomas, Germ Cell Tumors, Germinomatous (Seminomatous), Germ Cell Tumors, Glioblastoma Multiforme (GBM), Gliosarcoma, Head And Neck Cancer, Hepatocellular Carcinoma, Hodgkin Lymphoma, Hypopharyngeal Cancer, Laryngeal Cancer, Leiomyosarcoma, Mantle Cell Lymphoma, Melanoma, Merkel Cell Carcinoma, Multiple Myeloma, Neuroendocrine Tumors, Non-Hodgkin Lymphoma, Non-Small Cell Lung Cancer, Oral Cavity (Mouth) Cancer, Oropharyngeal Cancer, Osteosarcoma, Ovarian Cancer, Pancreatic Cancer, Peripheral Nerve Sheath Tumor (Neurofibrosarcoma), Peripheral T-Cell Lymphomas (PTCL), Peritoneal Cancer, Prostate Cancer, Renal Cell Carcinoma, Salivary Gland Cancer, Skin Cancer, Small-Cell Lung Cancer, Soft Tissue Sarcoma, Squamous Cell Carcinoma, Synovial Sarcoma, Testicular Cancer, Thymic Carcinoma, Thyroid Cancer, Ureter Cancer, Urethral Cancer, Uterine Cancer, Vaginal Cancer, Vulvar Cancer.

According to some embodiments of the invention the diseases to be treated by a fusion protein comprising PD1 or the ECD thereof and 41BBL or ECD thereof, such as for example, PD1-G-41BBL are: Acute myeloid leukemia, Bladder Cancer, Breast Cancer, chronic lymphocytic leukemia, Chronic myelogenous leukemia, Colorectal cancer, Diffuse large B-cell lymphoma, Epithelial Ovarian Cancer, Epithelial Tumor, Fallopian Tube Cancer, Follicular Lymphoma, Glioblastoma multiform, Hepatocellular carcinoma, Head and Neck Cancer, Leukemia, Lymphoma, Mantle Cell Lymphoma, Melanoma, Mesothelioma, Multiple Myeloma, Nasopharyngeal Cancer, Non Hodgkin lymphoma, Non-small-cell lung carcinoma, Ovarian Cancer, Prostate Cancer, Renal cell carcinoma.

According to specific embodiments, the cancer is selected from the group consisting of lymphoma, leukemia, colon cancer, pancreatic cancer, ovarian cancer, lung cancer and squamous cell carcinoma.

According to specific embodiments, the cancer is selected from the group consisting of lymphoma, carcinoma and leukemia.

According to specific embodiments, the cancer is colon carcinoma.

According to specific embodiments, the cancer is ovarian carcinoma.

According to specific embodiments, the cancer is lung carcinoma.

According to specific embodiments, the cancer is head and neck carcinoma.

According to specific embodiments, the cancer is leukemia.

According to specific embodiments, the leukemia is selected from the group consisting of acute nonlymphocytic leukemia, chronic lymphocytic leukemia, acute granulocytic leukemia, chronic granulocytic leukemia, acute promyelocytic leukemia, adult T-cellleukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, ( )ross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

According to specific embodiments, the leukemia is promyelocytic leukemia, acute myeloid leukemia or chronic myelogenous leukemia.

According to specific embodiments, the cancer is lymphoma.

According to specific embodiments, the lymphoma is B cell lymphoma

According to specific embodiments, the lymphoma is T cell lymphoma.

According to other specific embodiments, the lymphoma is Hodgkins lymphoma.

According to specific embodiments, the lymphoma is non-Hodgkins lymphoma.

According to specific embodiments, the non-Hodgkin's Lymphoma is a selected from the group consisting of aggressive NHL, transformed NHL, indolent NHL, relapsed NHL, refractory NHL, low grade non-Hodgkin's Lymphoma, follicular lymphoma, large cell lymphoma, B-cell lymphoma, T-cell lymphoma, Mantle cell lymphoma, Burkitt's lymphoma, NK cell lymphoma, diffuse large B-cell lymphoma, acute lymphoblastic lymphoma, and cutaneous T cell cancer, including mycosos fungoides/Sezry syndrome.

According to specific embodiments, the cancer is multiple myeloma.

According to at least some embodiments, the multiple myeloma is selected from the group consisting of multiple myeloma cancers which produce light chains of kappa-type and/or light chains of lambda-type; aggressive multiple myeloma, including primary plasma cell leukemia (PCL); benign plasma cell disorders such as MGUS (monoclonal gammopathy of undetermined significance), Waldenstrom's macroglobulinemia (WM, also known as lymphoplasmacytic lymphoma) which may proceed to multiple myeloma; smoldering multiple myeloma (SMM), indolent multiple myeloma, premalignant forms of multiple myeloma which may also proceed to multiple myeloma; primary amyloidosis.

A suggested Mode of action of PD1-41BBL

In one embodiment, the chimera PD1-41BBL can be used for treating of cancer via the following possible mode-of-action:

- Due to the relatively high expression of PDL1 on the surface of tumor cells and in the tumor micro-environment, the PD1 moiety of the PD1-41BBL chimera will target the molecule to tumor and metastasis sites, and will bind the chimera to PDL1 within the tumor micro-environment.
- Targeting the chimera to the tumor cells or/and tumor micro-environment will facilitate an increase in PD1-41BBL concentration in the tumor micro-environment and subsequent oligomerization of the 41BBL moiety of the chimera at the tumor site. Since oligomerization of 41BBL is a necessary step for 41BB signaling, this 41BBL binding and oligomerization will deliver a 41BB co-stimulatory signal that will promote activation of T-cells, B cells, NK cells, especially Tumor-Infiltrating Lymphocytes (TILs), and other immune cells at the tumor site, to kill cancer cells.
- In addition to the 41BBL-41BB co-stimulatory signal, the binding of the chimera's PD1 moiety to PDL1 in the tumor site will compete with the endogenous PD1 expressed on T cells, thus, removing the inhibition on T cells and further contributing to the activation of TILs in the tumor micro-environment.

The above activities of PD1-41BBL are anticipated to lead to a synergistic effect on the activation of TILs within the tumor micro-environment, which is expected to be more specific and more robust effect as compared to the effect of each peptide or ECD thereof separately, as well as when using the two different peptides or ECD thereof in combination.

Thus, according to specific embodiments, the cancer is defined by the presence of tumors that have tumor-infiltrating lymphocytes (TILs) in the tumor micro-environment and/or tumors with expression of PDL1 in the tumor micro-environment.

Thus, according to specific embodiments, the cancer is defined by the presence of tumors that have tumor-infiltrating lymphocytes (TILs) in the tumor micro-environment and/or tumors with a relatively high expression of PDL1 in the tumor micro-environment.

According to specific embodiments, cells of the cancer express PD-L1.

According to specific embodiments, the disease comprises a disease associated with immune suppression or immunosuppression caused by medication (e.g. mTOR inhibitors, calcineurin inhibitor, steroids).

According to specific embodiments, the disease comprises HIV, Measles, influenza, LCCM, RSV, Human Rhinoviruses, EBV, CMV or Parvo viruses.

According to specific embodiments, the disease comprises an infection.

As used herein, the term "infection" or "infectious disease" refers to a disease induced by a pathogen. Specific examples of pathogens include, viral pathogens, bacterial pathogens e.g., intracellular mycobacterial pathogens (such as, for example, *Mycobacterium tuberculosis*), intracellular bacterial pathogens (such as, for example, *Listeria monocytogenes*), or intracellular protozoan pathogens (such as, for example, *Leishmania* and *Trypanosoma*).

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection, rabies, etc.

According to specific embodiments, the compositions of the present invention (e.g. PD1-41BBL fusion protein, polynucleotide or nucleic acid construct encoding same and/or host-cell expressing same) can be administered to a subject in combination with other established or experimental therapeutic regimen to treat a disease that can benefit from activating immune cells (e.g. cancer) including, but not limited to analgesics, chemotherapeutic agents, radiotherapeutic agents, cytotoxic therapies (conditioning), hormonal therapy, antibodies and other treatment regimens (e.g., surgery) which are well known in the art.

According to specific embodiments, the compositions of the present invention (e.g. PD1-41BBL fusion protein, polynucleotide or nucleic acid construct encoding same and/or host-cell expressing same) can be administered to a subject in combination with adoptive cell transplantation such as, but not limited to transplantation of bone marrow cells, hematopoietic stem cells, PBMCs, cord blood stem cells and/or induced pluripotent stem cells.

According to specific embodiments, the therapeutic agent administered in combination with the composition of the invention comprises an anti-cancer agent.

Thus, according to another aspect of the present invention, there is provided a method of treating cancer comprising administering to a subject in need thereof an anti-cancer agent; and a PD1-41BBL fusion protein, a polynucleotide encoding same, a nucleic acid construct encoding same or a host cell expressing same.

Anti-cancer agent that can be use with specific embodiments of the invention include, but are not limited to the anti-cancer drugs Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

According to specific embodiments, the anti-cancer agent comprises an antibody.

According to specific embodiments, the antibody is selected from the group consisting of rituximab, cetuximab, trastuzumab, edrecolomab, alemtuzumab, gemtuzumab, ibritumomab, panitumumab Belimumab, Bevacizumab, Bivatuzumab mertansine, Blinatumomab, Blontuvetmab, Brentuximab vedotin, Catumaxomab, Cixutumumab, Daclizumab, Adalimumab, Bezlotoxumab, Certolizumab pegol, Citatuzumab bogatox, Daratumumab, Dinutuximab, Elotuzumab, Ertumaxomab, Etaracizumab, Gemtuzumab ozogamicin, Girentuximab, Necitumumab, Obinutuzumab, Ofatumumab, Pertuzumab, Ramucirumab, Siltuximab, Tositumomab, Trastuzumab and ipilimumab.

According to specific embodiments, the antibody is selected from the group consisting of rituximab and cetuximab.

According to specific embodiments, the therapeutic agent administered in combination with the composition of the invention comprises an anti-infection agent (e.g. antibiotics and anti-viral agents) According to specific embodiments, the therapeutic agent administered in combination with the composition of the invention comprises an immune suppressor agent (e.g. GCSF and other bone marrow stimulators, steroids).

According to specific embodiments the combination therapy has an additive effect.

According to specific embodiments, the combination therapy has a synergistic effect.

According to another aspect of the present invention there is provided an article of manufacture identified for the treatment of a disease that can benefit from activating immune cells comprising a packaging material packaging a therapeutic agent for treating said disease; and a PD1-41BBL fusion protein, a polynucleotide encoding same, a nucleic acid construct encoding same or a host cell expressing same.

According to specific embodiments, the therapeutic agent for treating said disease; and a PD1-41BBL fusion protein, a polynucleotide encoding same, a nucleic acid construct encoding same or a host cell expressing same are packages in separate containers.

According to specific embodiments, the therapeutic agent for treating said disease; and a PD1-41BBL fusion protein, a polynucleotide or a nucleic acid encoding same, a nucleic acid construct encoding same or a host cell expressing same are packages in a co-formulation.

As used herein, in one embodiment, the term "amino acid derivative" or "derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NH-G(Sc)-C(0)-Q or —OC(0)G($S_c$)-Q, wherein Q is —SR, —NRR or alkoxyl, R is hydrogen or alkyl, $S_c$ is a side chain of a naturally occurring or non-naturally occurring amino acid and G is $C_1$-C2 alkyl. In certain embodiments, G is Ci alkyl and Sc is selected from the group consisting of hydrogen, alkyl, heteroalkyl, arylalkyl and heteroarylalkyl.

As used herein, in one embodiment, the term "peptide", "polypeptide" or "protein, which are interchangeably used herein, may be derived from a natural biological source, synthesized, or produced by recombinant technology. It may be generated in any manner known in the art of peptide or protein synthesis, including by chemical synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965. One or more of the amino acids may be modified, for example, by the addition of a chemical entity such as a carbohydrate group, a phosphate group, a farnesyl group, an isofamesyt group, a fatty acid group, an acyl group (e.g., acetyl group), a linker for conjugation, functionalization, or other known protecting/blocking groups. Modifications to the peptide or protein can be introduced by gene synthesis, site-directed (e.g., PCR based) or random mutagenesis (e.g., EMS) by exonuclease deletion, by chemical modification, or by fusion of polynucleotide sequences encoding a heterologous domain or binding protein, for example.

As used herein, in one embodiment, the term "peptide," may be fragments, derivatives, analogs, or variants of the foregoing peptides, and any combination thereof. Fragments of peptides, as that term or phrase is used herein, include proteolytic fragments, as well as deletion fragments. Variants of peptides include fragments and peptides with altered amino acid sequences due to amino acid substitutions, deletions, or insertions.

Variants may occur naturally or be non-naturally occurring. Examples include fusion proteins, peptides having one or more residues chemically derivatized by reaction of a functional side group, and peptides that contain one or more naturally occurring amino acid derivatives of the twenty standard amino acids. These modifications may also include the incorporation of D-amino acids, or other non-encoded amino-acids. In one embodiment, none of the modifications should substantially interfere with the desired biological activity of the peptide, fragment thereof. In another embodiment, modifications may alter a characteristic of the peptide, fragment thereof, for instance stability or half-life, without interfering with the desired biological activity of the peptide, fragment thereof. In one embodiment, as used herein the terms "peptide" and "protein" may be used interchangeably having all the same meanings and qualities.

In one embodiment, to facilitate recovery, the expressed coding sequence can be engineered to encode the peptide of the present invention and fused cleavable moiety. In one embodiment, a fusion protein can be designed so that the peptide can be readily isolated by affinity chromatography; e.g., by immobilization on a column specific for the cleavable moiety. In one embodiment, a cleavage site is engineered between the peptide and the cleavable moiety and the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, each of the peptides that forms the fusion protein (also termed here "the peptide") of the present invention can also be synthesized using in vitro expression systems. In one embodiment, in vitro synthesis methods are well known in the art and the components of the system are commercially available.

In one embodiment, production of a peptide of this invention is using recombinant DNA technology. A "recombinant" peptide, or protein refers to a peptide, or protein produced by recombinant DNA techniques; i.e., produced from cells transformed by an exogenous DNA construct encoding the desired peptide or protein.

Thus, according to another aspect of the present invention, there is provided an isolated polynucleotide comprising a nucleic acid sequence encoding any of the above described fusion proteins.

According to specific embodiments, the polynucleotide comprises SEQ ID NO: 9.

According to specific embodiments, the polynucleotide consists of SEQ ID NO: 9.

According to specific embodiments, the polynucleotide is least about 70%, 75%, 80%, 85%, 90%, 95%, 96%, 97%, 98% or 99% homologous to the nucleic sequence as set forth in SEQ ID No. 9.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

To express exogenous PD1-41BBL in mammalian cells, a polynucleotide sequence encoding PD1-41BBL is preferably ligated into a nucleic acid construct suitable for mammalian cell expression. Such a nucleic acid construct includes a promoter sequence for directing transcription of the polynucleotide sequence in the cell in a constitutive or inducible manner.

Hence, according to specific embodiments, there is provided nucleic acid construct comprising the polynucleotide and a regulatory element for directing expression of said polynucleotide in a host cell.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters.

Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of PD1-41BBL mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding a PD1-41BBL can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of PD1-41BBL since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

As mentioned, other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the PD1-41BBL protein of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the PD1-41BBL protein and the heterologous protein, the PD1-41BBL protein can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

The present invention also contemplates cells comprising the composition described herein.

Thus, according to specific embodiments, there is provided a host cell comprising the PD1-41BBL fusion protein, the polynucleotide encoding same or the nucleic acid construct encoding same.

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of *E. coli* expression vectors [Studier et al. (1990) Methods in Enzymol. 185:60-89).

Examples of eukaryotic cells which may be used along with the teachings of the invention include but are not limited to, mammalian cells, fungal cells, yeast cells, insect cells, algal cells or plant cells.

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art can also be used by some embodiments of the invention.

According to specific embodiments the cell is a mammalian cell.

According to specific embodiment, the cell is a human cell.

According to a specific embodiment, the cell is a cell line.

According to another specific embodiment, the cell is a primary cell.

The cell may be derived from a suitable tissue including but not limited to blood, muscle, nerve, brain, heart, lung, liver, pancreas, spleen, thymus, esophagus, stomach, intestine, kidney, testis, ovary, hair, skin, bone, breast, uterus, bladder, spinal cord, or various kinds of body fluids.

The cells may be derived from any developmental stage including embryo, fetal and adult stages, as well as developmental origin i.e., ectodermal, mesodermal, and endodermal origin.

Non limiting examples of mammalian cells include monkey kidney CV1 line transformed by SV40 (COS, e.g. COS-7, ATCC CRL 1651); human embryonic kidney line (HEK293 or HEK293 cells subcloned for growth in suspension culture, Graham et al., J. Gen Virol., 36:59 1977); baby hamster kidney cells (BHK, ATCC CCL 10); mouse sertoli cells (TM4, Mather, Biol. Reprod., 23:243-251 1980); monkey kidney cells (CV1 ATCC CCL 70); African green monkey kidney cells (VERO-76, ATCC CRL-1587); human cervical carcinoma cells (HeLa, ATCC CCL 2); NIH3T3, Jurkat, canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 1982); MRC 5 cells; FS4 cells; and a human hepatoma line (Hep G2), PER.C6, K562, and Chinese hamster ovary cells (CHO).

According to some embodiments of the invention, the mammalian cell is selected from the group consisting of a Chinese Hamster Ovary (CHO), HEK293, PER.C6, HT1080, NS0, Sp2/0, BHK, Namalwa, COS, HeLa and Vero cell.

According to some embodiments of the invention, the host cell comprises a Chinese Hamster Ovary (CHO), PER.C6 or a 293 (e.g. Expi293F) cell.

According to another aspect of the present invention, there is provided a method of producing a PD1-41BBL fusion protein, the method comprising expressing in a host cell the polynucleotide or the nucleic acid construct described herein.

According to specific embodiments, the methods comprising isolating the fusion protein.

According to specific embodiments, recovery of the recombinant polypeptide is effected following an appropriate time in culture. The phrase "recovering the recombinant polypeptide" refers to collecting the whole fermentation medium containing the polypeptide and need not imply additional steps of separation or purification. Notwithstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, mix mode chromatography, metal affinity chromatography, Lectins affinity chromatography chromatofocusing and differential solubilization.

In some embodiments, the recombinant peptides, fragments thereof or peptides are synthesized and purified; their therapeutic efficacy can be assayed either in vivo or in vitro. In one embodiment, the activities of the recombinant fragments or peptides of the present invention can be ascertained using various assays including cell viability, survival of transgenic mice, and expression of megakaryocytic and lymphoid RNA markers.

In one embodiment, a peptide of this invention comprises at least 3 amino acids. In another embodiment, a peptide comprises at least 5 amino acids. In another embodiment, a peptide comprises at least 10 amino acids. In another embodiment, a peptide comprises at least 20 amino acids. In another embodiment, a peptide comprises at least 25 amino acids. In other embodiments, a peptide comprises at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids. In one embodiment, a peptide of this invention consists essentially of at least 5 amino acids. In another embodiment, a peptide consists essentially of at least 10 amino acids. In other embodiments, a peptide consists essentially of at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids. In one embodiment, a peptide of this invention consists of at least 5 amino acids. In another embodiment, a peptide consists of at least 10 amino acids. In other embodiments, a peptide consists of at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids or 500 or 600 or 700 amino acids.

As used herein, in one embodiment, the terms "peptide" and "fragment" may be used interchangeably having all the same meanings and qualities. As used herein in, in one embodiment the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to, N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein under.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In one embodiment, the peptide of this invention further comprises a detectable tag. As used herein, in one embodiment the term "detectable tag" refers to any moiety that can be detected by a skilled practitioner using art known techniques. Detectable tags for use in the screening methods of the present invention may be peptide sequences. Optionally the detectable tag may be removable by chemical agents or by enzymatic means, such as proteolysis. For example the term "detectable tag" includes chitin binding protein (CBP)-tag, maltose binding protein (MBP)-tag, glutathione-S-transferase (GST)-tag, poly(His)-tag, FLAG tag, Epitope tags, such as, V5-tag, c-myc-tag, and HA-tag, and fluorescence tags such as green fluorescent protein (GFP), red fluorescent protein (RFP), yellow fluorescent protein (YFP), blue fluorescent protein (BFP), and cyan fluorescent protein (CFP); as well as derivatives of these tags, or any tag known in the art. The term "detectable tag" also includes the term "detectable marker".

In one embodiment, a peptide of this invention is an isolated peptide. Such an isolated peptide may include a peptide-tag.

The peptides of some embodiments of the invention are preferably utilized in a linear form, although it will be appreciated that in cases where cyclicization does not severely interfere with peptide characteristics, cyclic forms of the peptide can also be utilized.

As used herein, in one embodiment the term "amino acid" refers to naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration.

Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, R-phenylalaninyl, R-tryptophanyl, R-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

Since the present peptides are preferably utilized in therapeutics or diagnostics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

As used herein, in one embodiment the phrase "Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant", including where the alteration results in the substitution of an amino acid with a chemically similar amino acid. Conservative substitution tables providing functionally similar amino acids are well known in the art. Guidance concerning which amino acid changes are likely to be phenotypically silent can also be found in Bowie et al., 1990, Science 247: 1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

Protein Chemical Modifications

In the present invention any part of a protein of the invention may optionally be chemically modified, i.e. changed by addition of functional groups. For example the side amino acid residues appearing in the native sequence may optionally be modified, although as described below alternatively other parts of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

By "PEGylated protein" is meant a protein, or a fragment thereof having biological activity, having a polyethylene glycol (PEG) moiety covalently bound to an amino acid residue of the protein.

By "polyethylene glycol" or "PEG" is meant a polyalkylene glycol compound or a derivative thereof, with or without coupling agents or derivatization with coupling or activating moieties (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polyalkylene glycol compounds include, but are not limited to, charged or neutral polymers of the following types: dextran, colominic acids or other carbohydrate based polymers, polymers of amino acids, and biotin derivatives.

Altered Glycosylation Protein Modification

Proteins of the invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to proteins of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on proteins of the invention may be accomplished chemically, enzymatically or by introducing changes at the DNA level. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

Pharmaceutical Compositions

The compositions (e.g. PD1-41BBL fusion protein, polynucleotide encoding same, nucleic acid construct encoding same and/or cells) of some embodiments of the invention can be administered to an organism per se, or in a pharmaceutical composition where it is mixed with suitable carriers or excipients.

The present invention, in some embodiments, features a pharmaceutical composition comprising a therapeutically effective amount of a therapeutic agent according to the present invention. According to the present invention the therapeutic agent could be a polypeptide as described herein. The pharmaceutical composition according to the present invention is further used for the treatment of cancer or an immune related disorder as described herein. The therapeutic agents of the present invention can be provided to the subject alone, or as part of a pharmaceutical composition where they are mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the composition (e.g. PD1-41BBL fusion protein, polynucleotide, nucleic acid construct and/or cells described herein) accountable for the biological effect.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., a polypeptide, a polynucleotide, a nucleic acid construct and/or cell as described herein, may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the present invention also may include a pharmaceutically acceptable anti-oxidants. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. A pharmaceutical composition according to at least some embodiments of the present invention also may include additives such as detergents and solubilizing agents (e.g., TWEEN 20 (polysorbate-20), TWEEN 80 (polysorbate-80)) and preservatives (e.g., Thimersol, benzyl alcohol) and bulking substances (e.g., lactose, mannitol).

Examples of suitable aqueous and nonaqueous carriers that may be employed in the pharmaceutical compositions according to at least some embodiments of the present invention include water, buffered saline of various buffer content (e.g., Tris-HCl, acetate, phosphate), pH and ionic strength, ethanol, polyols (such as glycerol, propylene glycol, polyethylene glycol, and the like), and suitable mixtures thereof, vegetable oils, such as olive oil, and injectable organic esters, such as ethyl oleate.

Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the present invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Techniques for formulation and administration of drugs may be found in "Remington's Pharmaceutical Sciences," Mack Publishing Co., Easton, PA, latest edition, which is incorporated herein by reference.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

A composition of the present invention can be administered via one or more routes of administration using one or more of a variety of methods known in the art. As will be appreciated by the skilled artisan, the route and/or mode of administration will vary depending upon the desired results. Preferred routes of administration for therapeutic agents according to at least some embodiments of the present invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intraperitoneal, intravenous (IV) and intradermal), transdermal (either passively or using iontophoresis or electroporation), transmucosal (e.g., sublingual administration, nasal, vaginal, rectal, or sublingual), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion or using bioerodible inserts, and can be formulated in dosage forms appropriate for each route of administration. In a specific embodiment, a protein, a therapeutic agent or a pharmaceutical composition according to at least some embodiments of the present invention can be administered intraperitoneally or intravenously.

Compositions of the present invention can be delivered to the lungs while inhaling and traverse across the lung epithelial lining to the blood stream when delivered either as an aerosol or spray dried particles having an aerodynamic diameter of less than about 5 microns. A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. For the polypeptide compositions disclosed herein, the polynucleotides and nucleic acids constructs encoding the same and the cells described herein, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For polypeptide compositions, generally dosage levels of 0.0001 to 100 mg/kg of body weight daily are administered to mammals and more usually 0.001 to 20 mg/kg. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration 5 times per week, 4 times per week, 3 times per week, 2 times per week, once per week, once every two weeks, once every three weeks, once every four weeks, once a month, once every 3 months or once every three to 6 months. Generally, for intravenous injection or infusion, dosage may be lower. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Optionally the polypeptide formulation may be administered in an amount between 0.0001 to 100 mg/kg weight of the patient/day, preferably between 0.001 to 20.0 mg/kg/day, according to any suitable timing regimen. A therapeutic composition according to at least some embodiments according to at least some embodiments of the present invention can be administered, for example, three times a day, twice a day, once a day, three times weekly, twice weekly or once weekly, once every two weeks or 3, 4, 5, 6, 7 or 8 weeks. Moreover, the composition can be administered over a short or long period of time (e.g., 1 week, 1 month, 1 year, 5 years).

Alternatively, therapeutic agent such as the compositions disclosed herein can be administered as a sustained release formulation, in which case less frequent administration is required. Dosage and frequency vary depending on the half-life of the therapeutic agent in the patient. In general, human antibodies show the longest half-life, followed by humanized antibodies, chimeric antibodies, and nonhuman antibodies. The half-life for fusion proteins may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A “therapeutically effective dosage” of a polypeptide as disclosed herein preferably results in a decrease in severity of disease symptoms, an increase in frequency and duration of disease symptom-free periods, an increase in lifespan, disease remission, or a prevention or reduction of impairment or disability due to the disease affliction.

One of ordinary skill in the art would be able to determine a therapeutically effective amount, especially in light of the detailed disclosure provided herein, based on such factors as the subject’s size, the severity of the subject’s symptoms, and the particular composition or route of administration selected.

In certain embodiments, the polypeptide, polynucleotide, nucleic acid construct or cells compositions are administered locally, for example by injection directly into a site to be treated. Typically, the injection causes an increased localized concentration of the polypeptide, polynucleotide, nucleic acid construct or cells compositions which is greater than that which can be achieved by systemic administration. The polypeptide compositions can be combined with a matrix as described above to assist in creating an increased localized concentration of the polypeptide compositions by reducing the passive diffusion of the polypeptides out of the site to be treated.

Pharmaceutical compositions of the present invention may be administered with medical devices known in the art. For example, in an optional embodiment, a pharmaceutical composition according to at least some embodiments of the present invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in an optional embodiment, a therapeutic composition according to at least some embodiments of the present invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat.

No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, to ensure that the therapeutic compounds according to at least some embodiments of the present invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J Physiol. 1233:134); $p^{120}$ (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Formulations for Parenteral Administration

In a further embodiment, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, polynucleotide, nucleic acid construct or cells described herein, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., water soluble antioxidants such as ascorbic acid, sodium metabisulfite, cysteine hydrochloride, sodium bisulfate, sodium metabisulfite, sodium sulfite; oil-soluble anti-oxidants, such as ascorbyl palmitate, butylated hydroxyanisole (BHA), butylated hydroxytoluene (BHT), lecithin, propyl gallate, alpha-tocopherol; and metal chelating agents, such as citric acid, ethylenediamine tetraacetic acid (EDTA), sorbitol, tartaric acid, phosphoric acid), and preservatives (e.g., Thimersol, benzyl alcohol) and bulking substances (e.g., lactose, mannitol). Examples of non-aqueous solvents or vehicles are ethanol, propylene glycol, polyethylene glycol, vegetable oils, such as olive oil and corn oil, gelatin, and injectable organic esters such as ethyl oleate. The formulations may be freeze dried (lyophilized) or vacuum dried and redissolved/resuspended immediately before use. The formulation may be sterilized by, for example, filtration through a bacteria retaining filter, by incorporating sterilizing agents into the compositions, by irradiating the compositions, or by heating the compositions.

Formulations for Topical Administration

Various compositions (e.g., polypeptides) disclosed herein can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations will require the inclusion of penetration enhancers.

Controlled Delivery Polymeric Matrices

Various compositions (e.g., polypeptides) disclosed herein may also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of polypeptides or nucleic acids encoding the polypeptides, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22

(1987); Mathiowitz, et al., Reactive Polymers, 6:275-283 (1987); and Mathiowitz, et al., J. Appl Polymer ScL, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10% The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

EXAMPLES

Proof of Concept (POC) Experiments

Manufacturing of a His-Tagged PD1-41BBL

For initial POC analysis, a histidine-tagged protein is produced. A cDNA sequence, coding for a 6-His-tagged PD1-41BBL, is sub-cloned into a mammalian expression vector. Transfection-grade plasmid preparation is used for plasmid transfection into Expi293 cells or other cell-lines. The supernatant of the Expi293 expressing cells (100 ml scale) is assessed for PD1-41BBL production by reduced and non-reduced SDS-PAGE and Western blot (WB) with an anti-His antibody. His-tagged PD1-41BBL is then purified from a positive supernatant by one-step affinity based purification (Nickel beads). The production of the tagged chimera protein is verified by SDS-PAGE and Western blot analysis using specific antibodies against each domain of the molecule (i.e. the extracellular domain each of PD1 and 41BBL)

Experiment 1A—Production of a His-tag PD1-41BBL Fusion Protein

Production of His-tag PD1-41BBL fusion protein (SEQ ID NO: 5) was effected in Expi293F cells transfected by a pcDNA3.4 expression vector cloned with coding sequence for the full fusion protein. The sequence was cloned into the vector using EcoRI and HindIII restriction enzymes, with addition of Kozak sequence, artificial signal peptide and 6 His-tag in the N terminus and a stop codon in the C terminus (SEQ ID NO: 18).

The protein was collected from supernatant of cell culture, and purified by one-step purification by HisTrap™ FF Crude column.

Experiment 1B—the Produced His-Tagged PD1-41BBL Fusion Protein Contains Both Domains Materials—His-tagged PD1-41BBL protein (SEQ ID NO: 5) produced as described in Experiment 1A hereinabove, protein marker: Spectra BR (Thermo Fisher Scientific, cat #26634), Anti PD1 (Cell Signaling, cat #86163), Anti 41BBL (BioVision, 5369-100), Mouse-anti-His mAb (GenScript, Cat. No. A00186), Secondary Goat Anti-Rabbit IgG (H+L)-HRP Conjugate (1:3333) (R&D, cat #170-6515), Recombinant human PD1 0.5 mg/ml (1086-PD-050) R&D, Recombinant human 41BBL (TNFSF9) 0.1 mg/ml (8460 LF) Cell Signaling Stripping buffer (Thermoscientific, cat #21059), Protein De-glycosylation Mix: (NEB p6044).

Methods—Proteins (250 ng per lane) were incubated at denaturing, or non denaturing conditions (in sample buffer containing β-mercaptoethanol and boiled for 5 minutes at 95° C., or, in sample buffer without β-mercaptoethanol without heating, respectively) and separated on 12% SDS-PAGE gel, followed by Western blotting. De-glycosylation treatment was effected by PNGase F enzyme according to the Protein De-glycosylation Mix manufacturer instructions.

Results

Figure 2B:
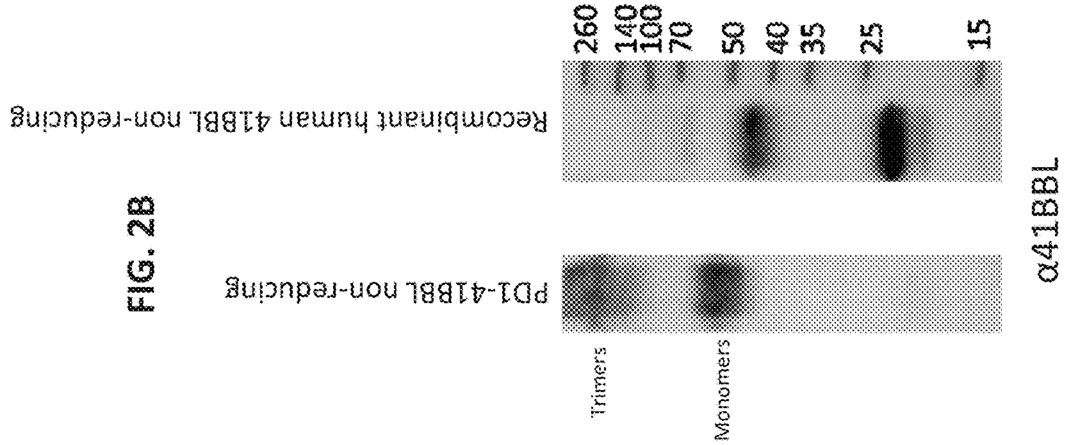
FIGS. 2A-2B are photographs of western blot analysis of His-tagged PD1-41BBL (SEQ ID NO: 5) under reducing or non-reducing conditions. Following affinity purification, proteins (250 ng/well) were separated on SDS-PAGE gel under denaturing (FIG. 2A) or non-denaturing (FIG. 2B) conditions, followed by immunoblotting with an anti-41BBL antibody.
Figure 2A:
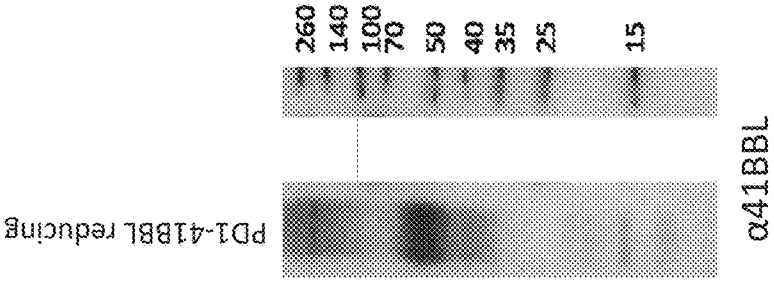
Figure 1:
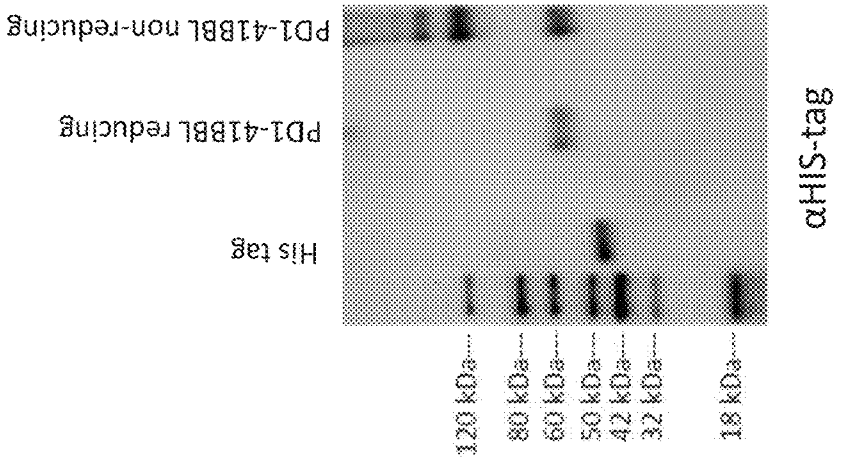
FIG. 1 is a photograph of western blot analysis of His-tagged PD1-41BBL (SEQ ID NO: 5) under reducing or non-reducing conditions. Following affinity purification, proteins (250 ng/well) were separated on SDS-PAGE gel under denaturing or non-denaturing conditions, as indicated, followed by immunoblotting with an anti-His-tag antibody.

Western blot analysis of His-tagged PD1-41BBL (SEQ ID NO: 5) separated on a SDS-PAGE gel under denaturing conditions followed by immunoblotting with an anti His-tag antibody or an anti-41BBL antibody demonstrated that both the N-terminal side of the molecule and the C-terminal side of the molecule are present (FIGS. 1 and 2A-2B). Although the predicted molecular weight of the protein according to its amino acid sequence is 39 kDa, the protein migrated under denaturing conditions as approximately 50-60 kDa in molecular weight. This shift was found to be related to the glycosylation of the protein, as determined by treating the protein with PNGase F enzyme that removes almost all N-linked oligosaccharides from glycoproteins. Following the treatment, a major band of about 39 kDa was observed (FIG. 2C).

When separated on a SDS-PAGE under non-denaturing conditions the His-tagged PD1-41BBL (SEQ ID NO: 5) was detected at the same molecular weight as under denaturing conditions (FIGS. 1, and 2B). Additional bands of higher molecular weight were also detected, which were stronger under the non-denaturing conditions compared to the denaturing conditions. This might suggest the formation of multimers, probably trimers, according to the molecular size and the fact that 41BBL protein naturally tends to form trimers (Eun-Young et al, 2010, THE JOURNAL OF BIOLOGICAL CHEMISTRY VOL. 285, NO. 12, pp. 9202-9210).

Experiment 1C—Binding Analysis of the PD1 and 41BBL Moieties of the Chimera to PDL1 and 41BB The binding of the PD1 domain of the molecule to PDL1 and the binding of the 41BBL domain of the molecule to 41BB was determined by the bio-layer interferometry Blitz® assay.

Materials—PD-L1:FC (Sino Biological, cat #12283-H02H), 41BB:FC (Sino Biological, cat #10041-H03H), His-tagged PD1-41BBL (SEQ ID NO: 5) produced as described in Experiment 1A hereinabove, SIRPα-41BBL (SEQ ID NO: 6, as a negative control), Soluble PD-L1 (as a competitor, Sino Biological cat #12283-H02H), PD1-CD70 (SEQ ID NO: 7, as a negative control), 41BB PE flow antibody (eBioscience, cat #12-1379-42), PDL1 APC flow antibody (Biolegend, cat #329708).

Figure 3A:
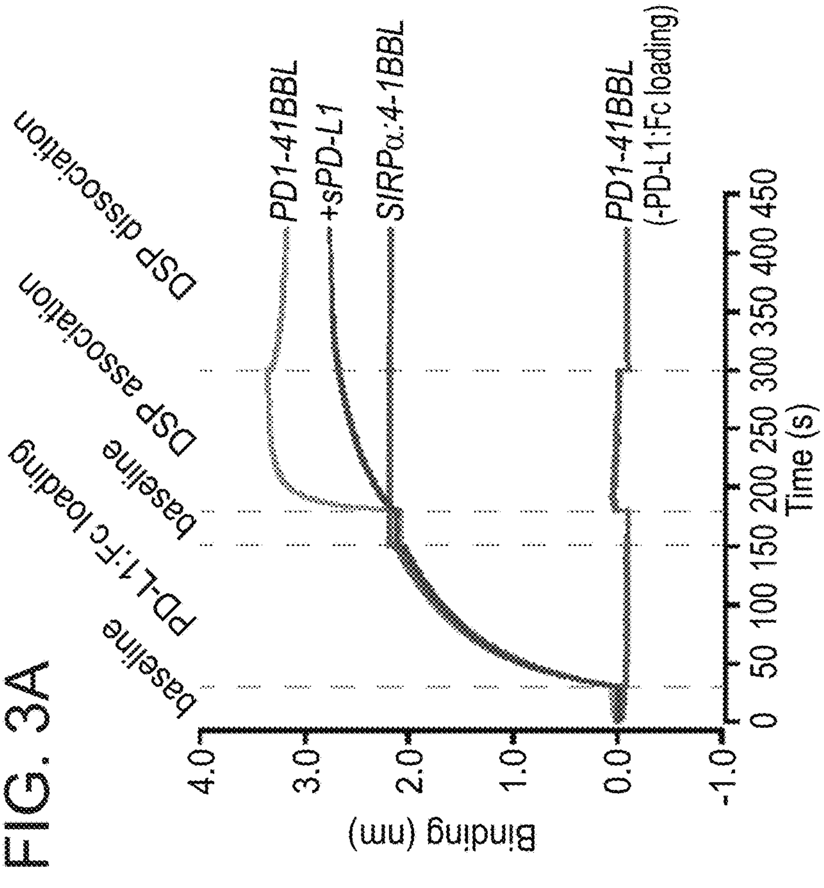
FIGS. 3A-3B are graphs demonstrating interaction of His-tagged PD1-41BBL (SEQ ID NO: 5) with its counterpart ligands, as determined by bio-layer interferometry Blitz® assay.

Methods and results—The biosensor was pre-loaded with PD-L1:Fc, which led to a stable association plateau (FIG. 3A). Upon subsequent incubation with His-tagged PD1-41BBL (SEQ ID NO: 5) a rapid association of the His-tagged PD1-41BBL to PD-L1:Fc was detected (FIG. 3A, upper line). Similar incubation with a control protein SIRPα-41BBL (composed of a SIRPα domain fused to 41BBL, SEQ ID NO: 6), did results in binding to PD-L1:Fc (FIG. 3A, middle lower line). Furthermore, when the biosensor was not pre-loaded with PD-L1:Fc, the His-tagged PD1-41BBL did not associate (FIG. 3A, lower line). Upon reaching a stable association plateau, the biosensor was washed with medium to determine the off-rate of the His-tagged PD1-41BBL from PD-L1:Fc. The dissociation of His-tagged PD1-41BBL from the PD-L1:Fc-loaded biosensor was slow, suggesting stable interaction of PD1 with PD-L1. Furthermore, soluble PD-L1 (sPD-L1) was loaded as a competitive binding inhibitor. Indeed, binding of His-tagged PD1-41BBL to PD-L1:Fc occurred at a lower yet detectable rate during the association phase, suggesting competitive binding to sPD-L1 (FIG. 3A, middle upper line)

Figure 3B:
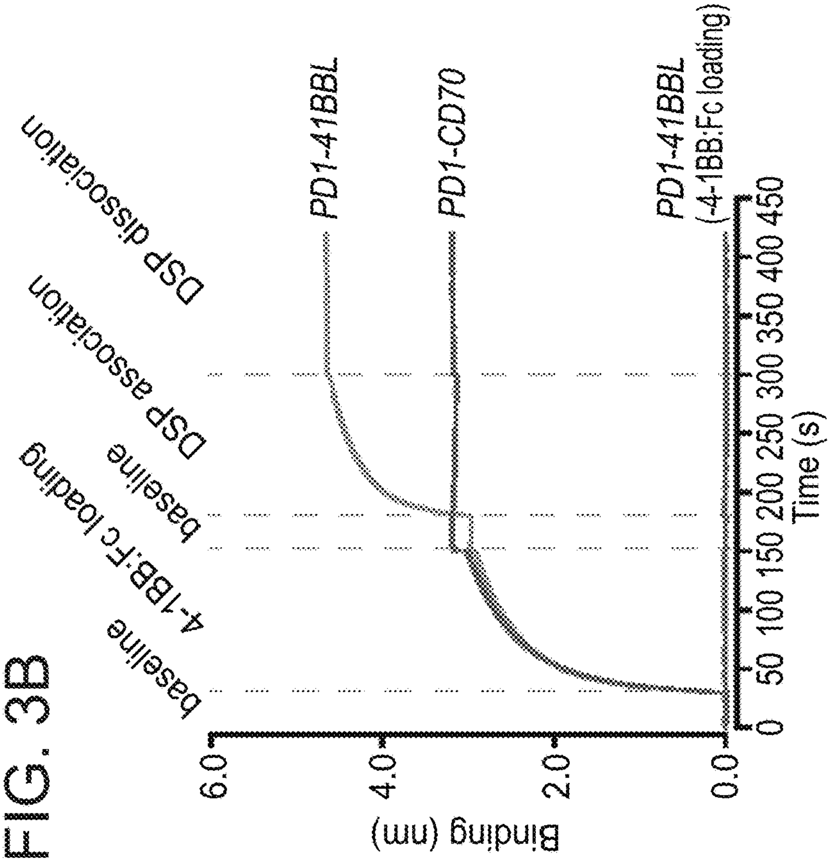

Upon similar loading of the biosensor with 41BB:Fc, binding of the 41BBL unit of His-tagged PD1-41BBL (SEQ ID NO: 5) was evaluated (FIG. 3B). As with the PD1 domain, the 41BBL domain of the PD1-41BBL rapidly bound to its target receptor (FIG. 3B, upper line); with the off-rate for the 41BBL/41BB interaction being also very slow, as evident from the limited dissociation occurring during the last dissociation phase. Control treatment with a PD1-CD70 (SEQ ID NO: 7), lacking the 41BBL domain, did not result in any detectable binding to 41BBL:Fc (FIG. 3B, middle line). Further, in the absence of pre-loading with 41BB:Fc, the His-tagged PD1-41BBL did not detectably bind the biosensor (FIG. 3B, lower line).

Taken together, both domains of the His-tagged PD1-41BBL (SEQ ID NO: 5) retain functional binding activity for their cognate receptors.

Experiment 1D—Binding Analysis of the PD1 and 41BBL Moieties of the Chimera to PDL1 and 41BB on Surface of Cells The binding of the PD1 domain of the molecule to human PDL1 is evaluated by using HT1080 cells or CHO-K1 cell or another cell line overexpressing PDL1. Cells are stained with different concentrations of His-tagged PD1-41BBL, and then by a secondary anti 4-1BBL antibody. Binding is analyzed by flow cytometry using fluorescence-activated cell sorting (FACS). The use of different concentrations of the chimera allows to determine affinity of the molecule to the PDL1. In this binding test, a recombinant PD1 is also used as competitor to the His-tagged-PD1-41BBL in order to verify the specificity of the binding. Antibodies that block the interaction between PD1 and PDL1 can be used as well for the same purpose. For this assay, DLD1 carcinoma cells that are treated with IFN gamma to express PDL1 can be used as well.

The binding of the 4-1BBL moiety of the chimera to human 4-1BB is tested by using HT1080 cells or another cell line that are overexpressing 4-1BB. Cells are stained with different concentrations of His-tagged-PD1-41BBL and then by a secondary anti PD1 antibody, and binding affinity is analyzed by FACS. In this binding test, a recombinant 41BBL is used as a competitor to the PD1-41BBL in order to verify the specificity of the binding. Antibodies that block the interaction between 41BB and 41BBL can be used for the same purpose as well.

Materials—His-tagged PD1-41BBL protein (SEQ ID NO: 5) produced as described in Experiment 1A hereinabove; HT1080-WT, HT1080-CD27, HT1080-41BB, DLD1-WT and DLD1-PDL1 cell lines (Lang et al 2015, Hendriks et al 2016), Fixable Viability Dye (BD Biosciences, cat #562247), Human Fc blocker True stain FCX (Bioledgend, cat #422302), and the following antibodies:

| | Target | Fluor | Cat# | Manufacturer |
|---|---|---|---|---|
| Antibodies used for expression study | anti CD27 | APC | 356410 | Biolegend |
| | IgG1 | | 400122 | |
| | anti 41BB (CD137) | | 309810 | |
| | IgG1 | | 400122 | |
| | anti PDL1 (CD274) | | BLG-329708 | |
| | Iso-C (IgG2b) | | BLG-400322 | |
| | anti CD47 | Alexa 647 | MCA2514A647 | BioRad |
| | IgG2b | | MCA691A647 | |
| Antibodies used for binding assays | anti 41BBL | PE | 311504 | Biolegend |
| | IgG1, K | | 400112 | |
| | anti CD70 | PE | 355104 | |
| | IgG1, K | | 400114 | |
| | anti PD1 | PE | 12-9969-42 | eBioscience |
| | IgG1, K | | 12-4714-42 | |

Methods—For expression assays, cells (0.5M cells/sample) were immuno-stained with the indicated antibodies, followed by Flow cytometry analysis. For binding assays, cells were pre-incubated with human Fc blocker prior to incubation with His-tagged PD1-41BBL (SEQ ID NO: 5) for 30 minutes on ice, followed by immuno-staining with antibodies against the free arm of the molecule, fixation and analysis by flow cytometry.

Figure 4A:
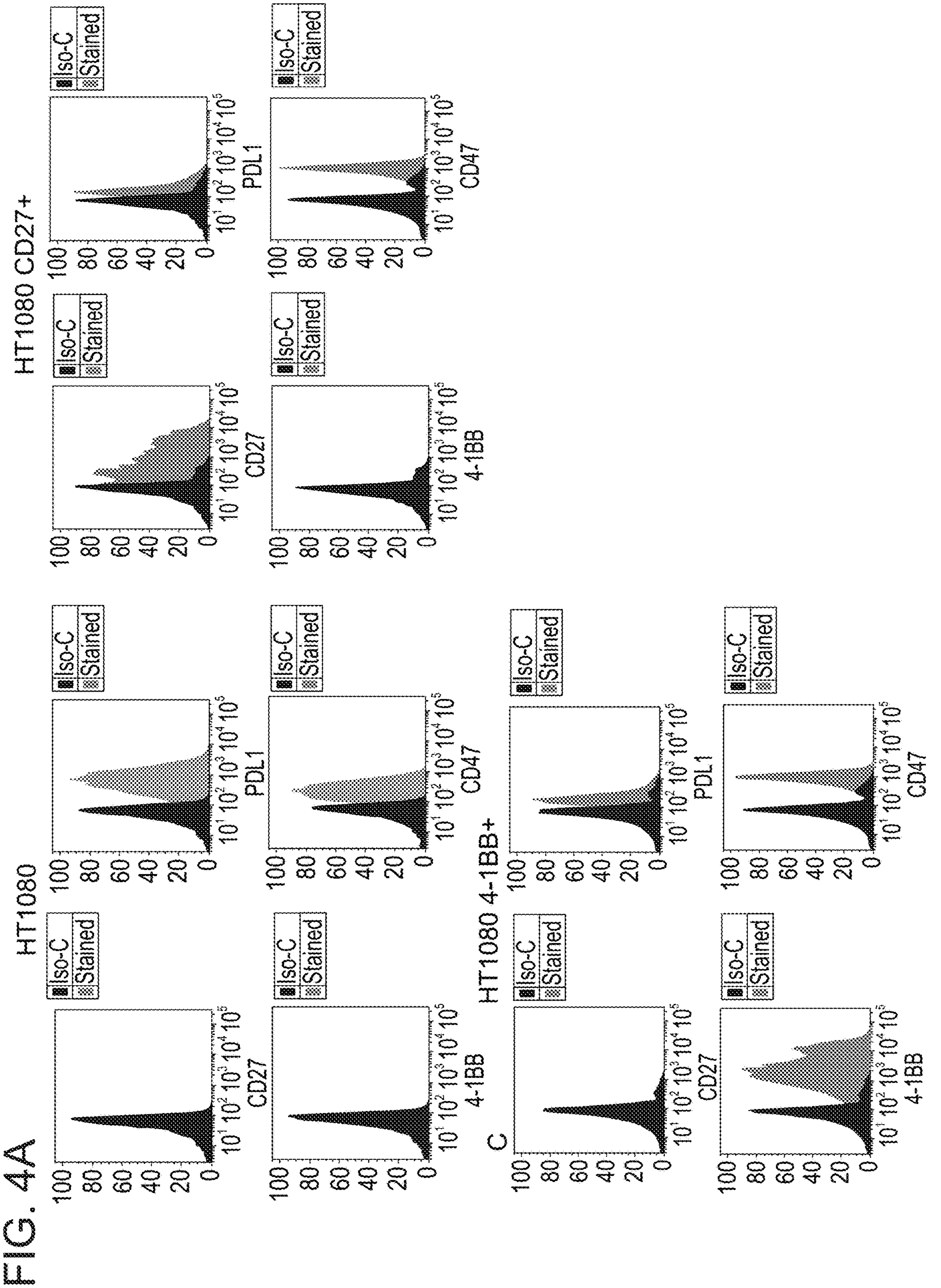
FIGS. 4A-4B are histograms (FIG. 4A) and a table summarizing Geometric mean fluorescence intensity (GMFI) (FIG. 4B) demonstrating expression of the indicated receptors on HT1080-WT (HT1080), HT1080-CD27, HT1080-41BB, DLD1-WT and DLD1-PDL1 cell lines. The surface expression levels of CD27, PDL1, 41BB and CD47 was determined by immuno-staining of each cell line with the corresponding antibodies, followed by flow cytometric analysis.
Figures 4A, 4B:
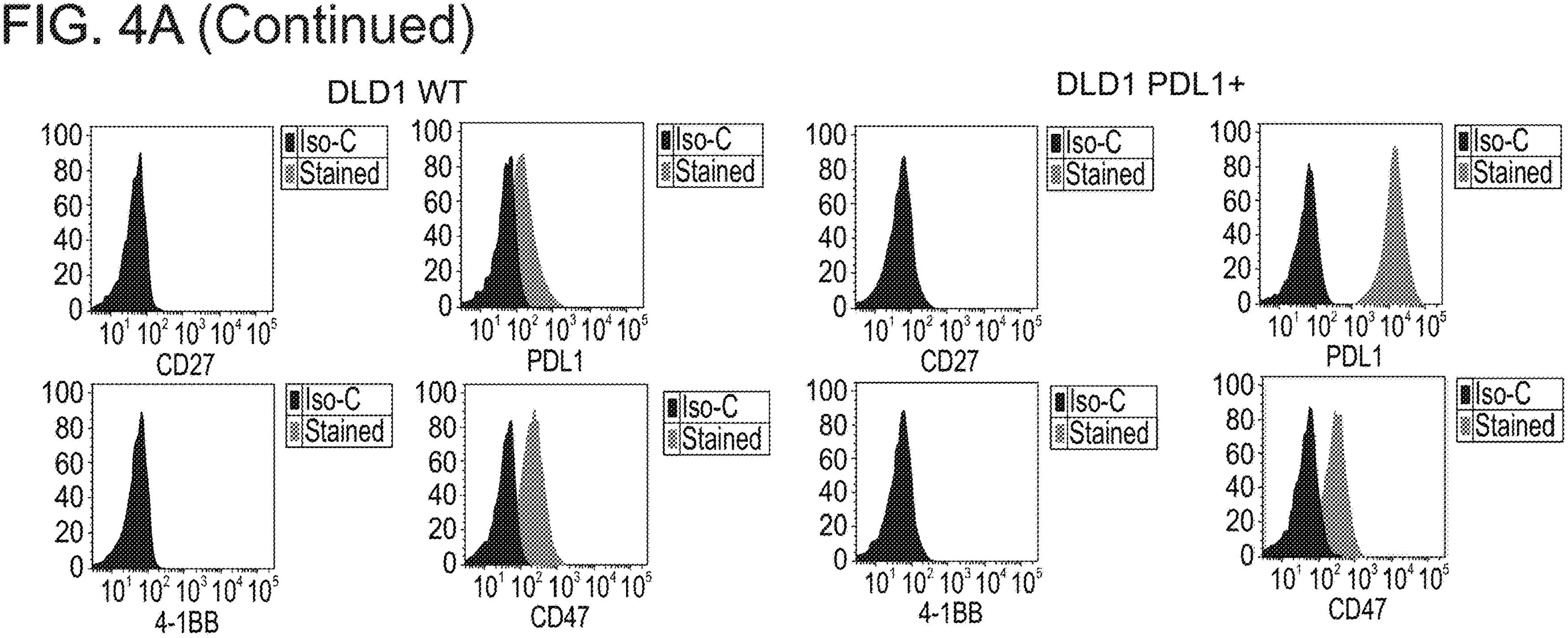

Results—As shown in FIG. 4A-4B, HT1080-CD27 and HT1080-41BB cells indeed express the relevant receptors, CD27 and 41BB, respectively, while HT1080-WT, DLD1-WT and DLD1-PDL1 cells do not express both receptors. CD47 and PDL1 are endogenously expressed on the surface of all the tested cell lines at different levels (FIGS. 4A-4B).

Figure 5A:
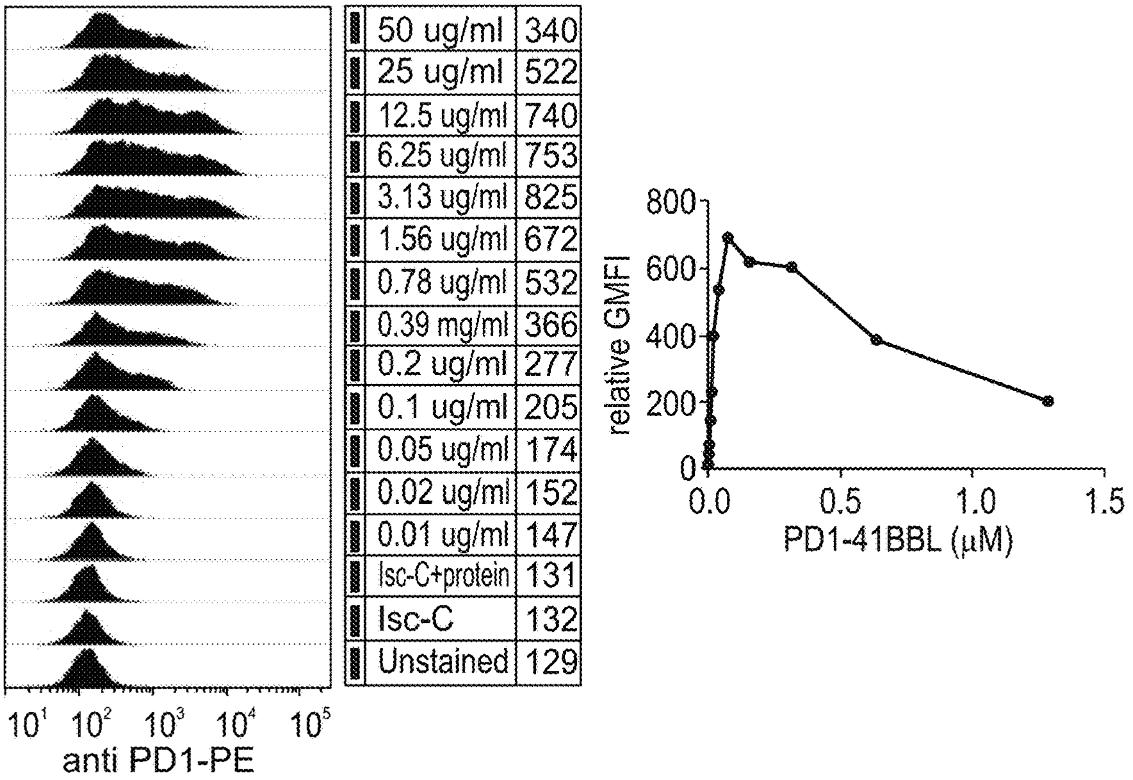
FIGS. 5A-5B demonstrate binding of His-tagged PD1-41BBL protein (SEQ ID NO: 5) to HT1080-41BB cells (FIG. 5A) but not to the negative control HT1080-CD27 cells (FIG. 5B). The cells were incubated with different concentrations of His-tagged PD1-41BBL protein (SEQ ID NO: 5) for 30 minutes on ice, followed by immunostaining with anti-PD-1 antibody and flow cytometry analysis. GMFI values were used to create a binding curve graph with a GraphPad Prism software.
Figure 5B:
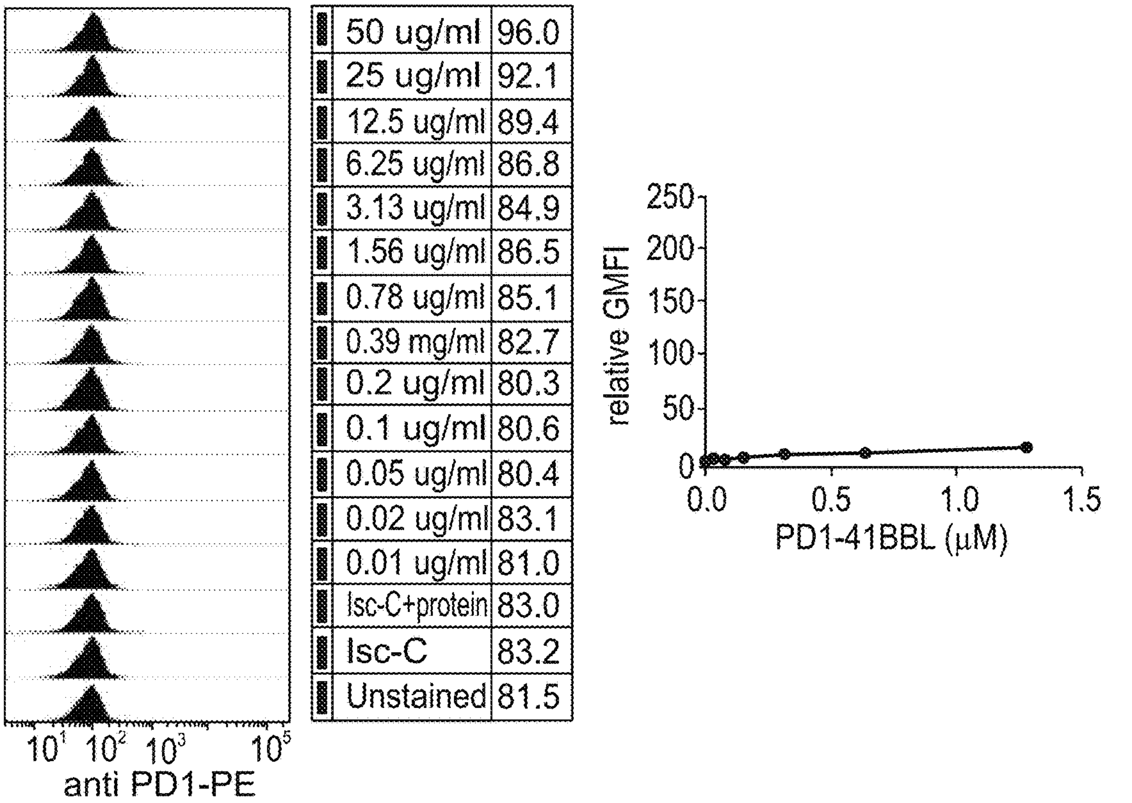
Figure 6A:
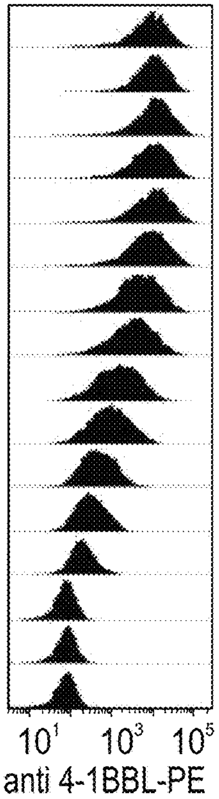
FIGS. 6A-6B demonstrate binding of His-tagged PD1-41BBL protein (SEQ ID NO: 5) to DLD1-PDL1 cells (FIG. 6A) but not to the negative control DLD1-WT cells. The cells were incubated with different concentrations of His-tagged PD1-41BBL protein (SEQ ID NO: 5) for 30 minutes on ice, followed by immunostaining with anti-41BBL antibody and flow cytometry analysis. GMFI values were used to create a binding curve graph with a GraphPad Prism software.
Figure 6A:
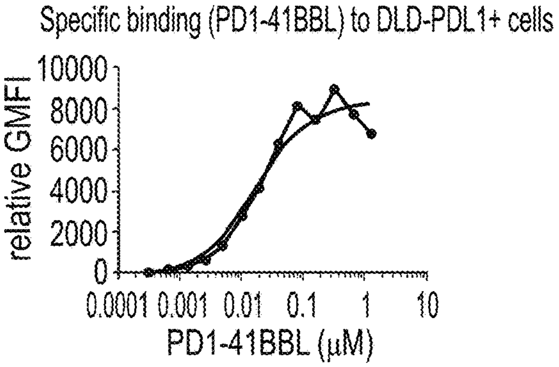
Figure 6B:
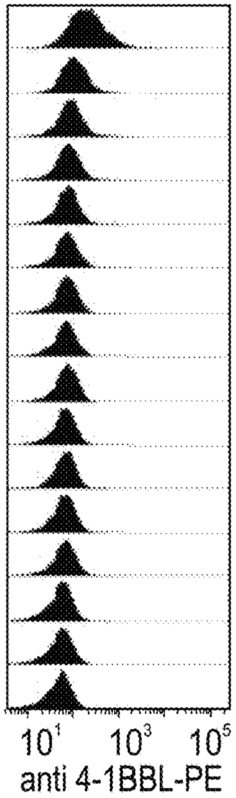
Figure 6B:
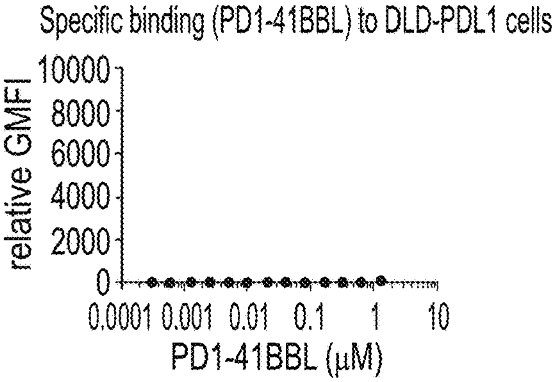
Figure 7:
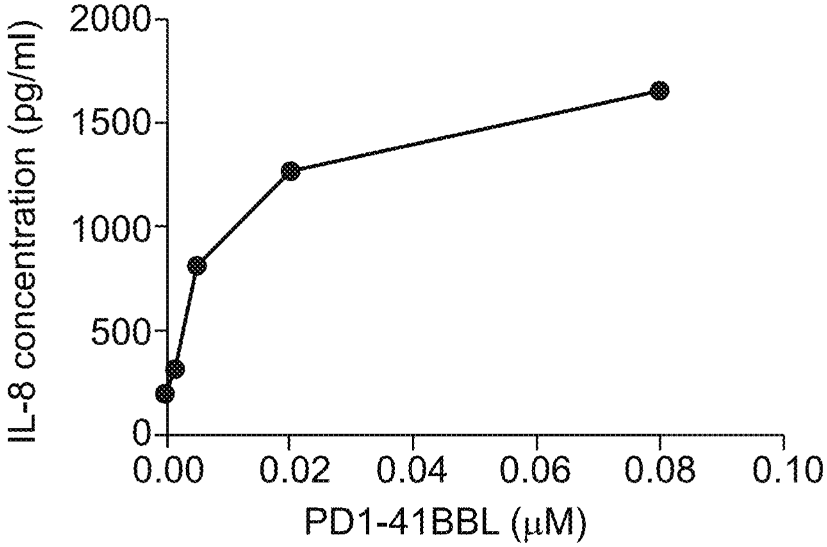
FIG. 7 is a graph demonstrating that His-tagged PD1-41BBL protein (SEQ ID NO: 5) promotes TNFR signaling as demonstrated by IL-8 secretion from HT1080-41BB cells in medium containing FBS.

Binding assays show that His-tagged PD1-41BBL (SEQ ID NO: 5) binds to HT1080-41BB cells and to DLD1-PDL1 cells in a dose dependent manner (FIGS. 5A and 6A), while it doesn't bind to the negative control HT1080-CD27 cells and to DLD1-WT cells (FIGS. 5B and 6B).

Taken together, both sides of the His-tagged PD1-41BBL protein (SEQ ID NO: 5), the N and C terminals, can bind their relevant counterparts overexpressed on the surface of cells.

Experiment 2—Activation of the 41BB Receptor by the Chimera

The activation effect of the 41BB receptor by the His-tagged PD1-41BBL is tested by using HT1080 cells or another cell line that are overexpressing the 41BB receptor. Specifically, the HT1080-41BB cell line is overexpressing 41BB and is known to secrete IL-8 upon binding of 41BBL (Wyzgol, et al, 2009, The Journal of Immunology). Upon binding of 41BBL to the 41BB receptor on the surface of these cells, a signaling pathway is activated resulting in secretion of IL8. The cells are incubated in the presence of the His-tagged-PD1-41BBL in different concentrations and IL8 secretion to the culture media is determined by ELISA. The oligomerization is tested by addition of anti-His-tag cross linking antibody in different concentrations. With the addition of the anti-His-tag Ab, the chimera molecules will be cross linked and form oligomers, resulting in an increased IL8 secretion. Anti PD1 antibody can be used for the same purpose as well (cross linking the PD1 moiety of the molecule). Recombinant PDL1 is used as negative control (recombinant PDL1 will not cross link PD1 and will not form oligomerization of the molecule).

The oligomerization is also tested by co-culturing the cells overexpressing the 41BB receptor with HT1080 cells that are overexpressing human PDL1. The PD1-41BBL binds to the PDL1 that is over expressed on the HT1080 cells and the 41BBL moiety is presented to the HT1080 that are overexpressing the 4-1BB receptor. Due to this presentation of several molecules in close vicinity, the requirement for oligomerization is fulfilled.

The activation of the 41BBL receptor by His-tagged PD1-41BBL can be compared to that of its parts, namely, recombinant PD1 or 41BBL alone or in combination.

Materials—His-tagged PD1-41BBL protein (SEQ ID NO: 5) produced as described in Experiment 1A hereinabove, HT1080-41BB cell line, IL-8 ELISA kit (cat #D8000C, R&D), DMEM (cat #01-055-1A, Biological industries), FBS (cat #10270106, Rhenium), AIM V (serum free medium) (Thermo Scientific)

Methods—HT1080-41BB cells (5000 per well) were incubated for 24 hours with different concentrations of His-tagged PD1-41BBL protein (SEQ ID NO: 5). IL-8 concentration in the supernatant was determined by IL-8 ELISA kit according to the manufacturer's protocol. Serum free medium was used for some of the experiments to eliminate relatively high background that was observed using medium with FBS.

Figure 8:
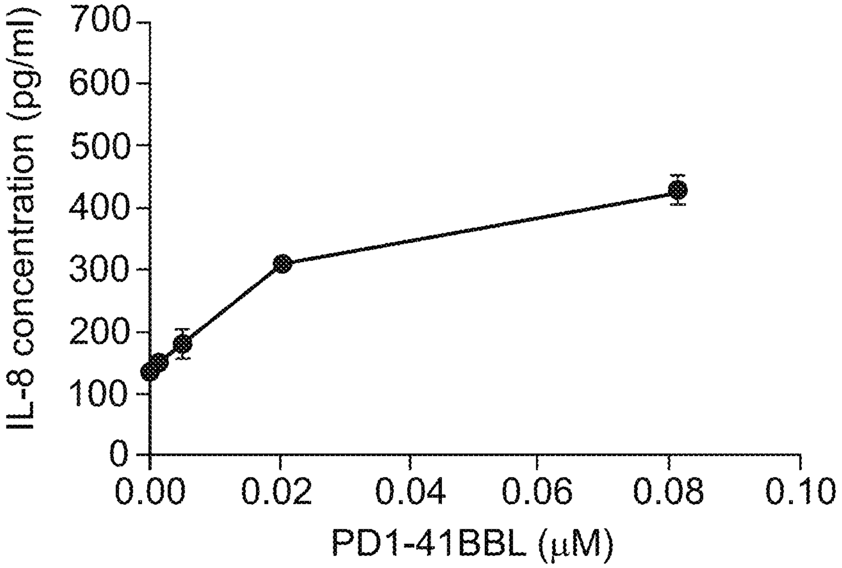
FIG. 8 is a graph demonstrating that His-tagged PD1-41BBL protein (SEQ ID NO: 5) promotes TNFR signaling as demonstrated by IL-8 secretion from HT1080-41BB cells in serum free media.

Results—Several independent experiments showed the functionality of His-tagged PD1-41BBL protein (SEQ ID NO: 5): His-tagged PD1-41BBL protein (SEQ ID NO: 5) was able to trigger TNFR signaling as determined by IL8 secretion by HT1080-41BBL cells, in a dose dependent manner both in medium containing FBS (FIG. 7) and in Serum free medium (FIG. 8).

Experiment 3—Activation of T-cells by PD1-41BBL

The effect of PD1-41BBL on the activation of T-cells is tested using either T-cells in human healthy donor PBMCs or by using human TILs. The T-cells are first co-cultured with human carcinoma cancer cells and treated with anti CD3 and anti Epcam1 bispecific antibodies to induce T-cell activation and then with the PD1-41BBL. The anti CD3/Epcam1 antibody is delivering the first signal for activation of T cells against the Epcam1 expressing cancer cells. The PD1-41BBL molecule is interacting with PDL1 expressed on the surface of cancer cells, this interaction facilitates the presentation and oligomerization of the molecule and by that, enables the interaction of the 41BBL moiety with 41BB receptor on The T cell and delivery of a second co-stimulatory signal to the T cell. The activation level of the T cells is determined by measuring several parameters; Firstly, by testing the expression of activation markers on the surface of the T cells, (for example: CD69, CD137, CD107a, PD1 etc.). Expression of activation markers is tested by staining the cells with specific antibodies and flow cytometry analysis (FACS). A second way to determine T cell activation is by measuring inflammatory cytokine secretion (for example: IL2, IL6, INF gamma etc.). Secretion of inflammatory cytokine is tested by ELISA. Proliferation of T cells is measured by pre-staining of T cells with CFSE (carboxyfluorescein succinimidyl ester) and determining deviation of cells by CFSE dilution that is determined by FACS. An additional parameter that is tested is the killing of the cancer cells that is measured by pre-labeling the cancer cells using Calcine-AM reagent and measuring Calcine release into the culture medium using luminescence plate reader.

The effect of PD1-41BBL on the activation of TILs is tested on TILs that are extracted from tumors and then co-cultured with the tumor cancer cells and treated with PD1-41BBL.

The first signal for activation of T cells is delivered by the cancer cells via MHC class I: peptide—TCR (T cell receptor) pathway. The PD1-41BBL fusion protein is interacting with PDL1 expressed on the surface of the tumor cells, this interaction facilitates the presentation and oligomerization of the molecule and accordingly enables the interaction of the 41BBL moiety with 41BB receptor on the T cell and delivery of a second co-stimulatory signal to the T cell. Activation level of the TILs and killing of tumor cells is determined in the same way as described (activation markers, cytokine secretion, proliferation and killing of tumor cells).

The activation of T-cells by His-PD1-41BBL can be compared to that of its parts, namely, recombinant PD1 or 41BBL alone or in combination.

Experiment 3A—PD1-41BBL Protein Demonstrates T Cell Co-Stimulatory Activity

Materials—His-tagged PD1-41BBL protein (SEQ ID NO: 5) produced as described in Experiment 1A hereinabove, HT1080-WT cells, HT1080-41BB cells, DLD1-PD-L1 cells, DLD1-WT cells (Lang et al 2015), freshly isolated human T cells, IL8 Elisa kit (R&D systems, cat #DY208), PD-L1:Fc (Sino Biological, cat #10084-H02H), anti-CD3/anti-CD28 activation beads (Life Technologies, cat #11131D), anti CD25 antibody (Immuno Tools, cat #21270256).

Methods and Results—The PD1-41BBL was designed to bind to PD-L1, thereby blocking PD-1/PDL1 inhibitory signaling; and at the same time trigger 41BB-mediated activation of T cells. In this experiment, the 41BBL domain of PD1-41BBL protein was evaluated for its potential to stimulate T-cells.

Figure 9A:
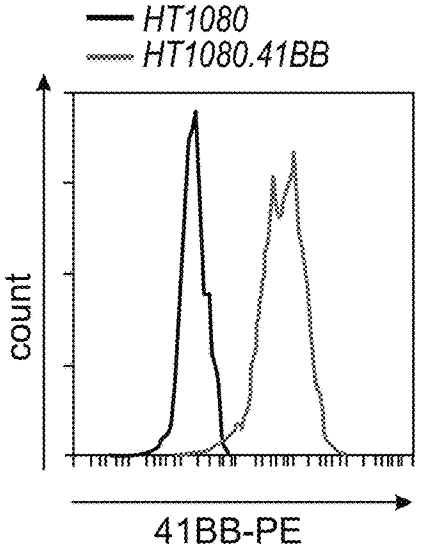
FIGS. 9A-9D demonstrate that His-tagged PD1-41BBL protein (SEQ ID NO: 5) triggers 41BB co-stimulatory signaling and potentiates T cell activation.
Figure 9B:
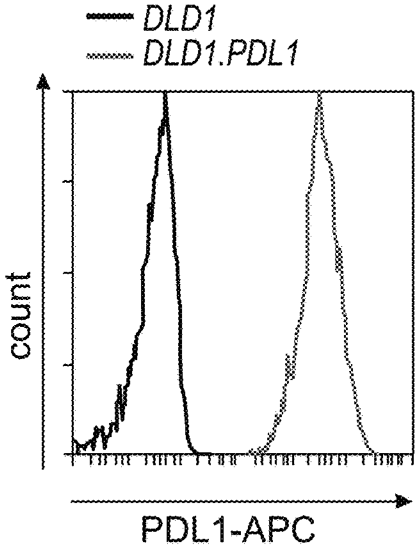
Figure 9C:
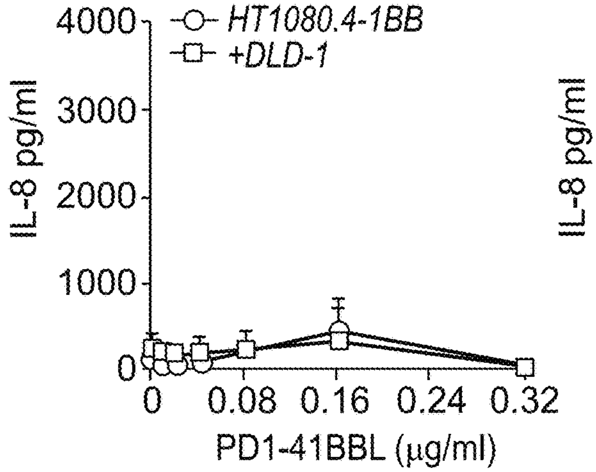
Figure 9D:
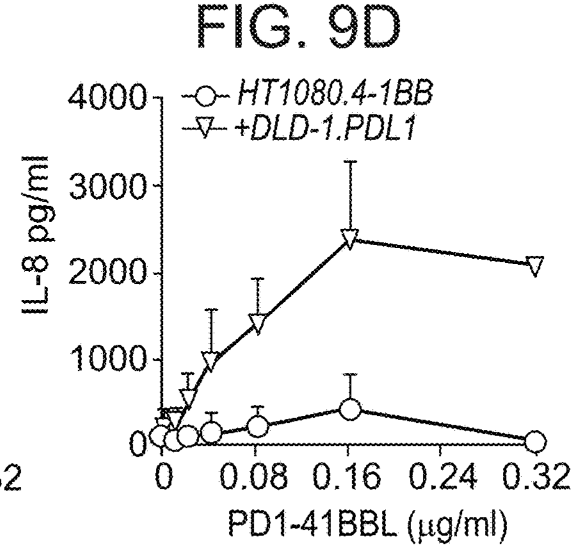

Staining of HT1080-WT cells showed that 41BB was not detected on the cells surface, while HT1080-41BB cells were positive for 41BB (FIG. 9A). Similarly, DLD1-WT cells stained for PDL1 were negative for PDL1, while DLD1-PDL1 cells were positive for PDL1 (FIG. 9B). Following, HT1080-41BB cells were mixed with DLD10PD-L1 cells or with control wild-type DLD1. Upon treatment of single cultures of HT1080-41BB with His-tagged PD1-41BBL protein (SEQ ID NO: 5), minimal production of IL-8 was detected following 24 hours of incubation (FIG. 9C). Similarly, treatment with His-tagged PD1-41BBL protein (SEQ ID NO: 5) minimally induced IL-8 secretion when HT1080-41BB cells were mixed with wild-type DLD1 cells (FIG. 9C). Thus, in the absence of PD-L1 binding, the PD1-41BBL has a minimal co-stimulatory activity. However, treatment of mixed cultures of HT1080-41BB and DLD1-PD-L1 with His-tagged PD1-41BBL protein (SEQ ID NO: 5), triggered a strong increase in IL-8 secretion that peaked at 2500 pg/mL (FIG. 9D). These results demonstrate that upon binding of the PD1 domain of His-tagged PD1-41BBLprotein (SEQ ID NO: 5) to PD-L1 expressing cells, the 41BBL domain is presented in a cross-linked form that can trigger 41BB co-stimulation. Thus, binding of the His-tagged PD1-41BBL protein (SEQ ID NO: 5) to PD-L1 is beneficial for functional 41BBL/41BB interaction.

Figure 10:
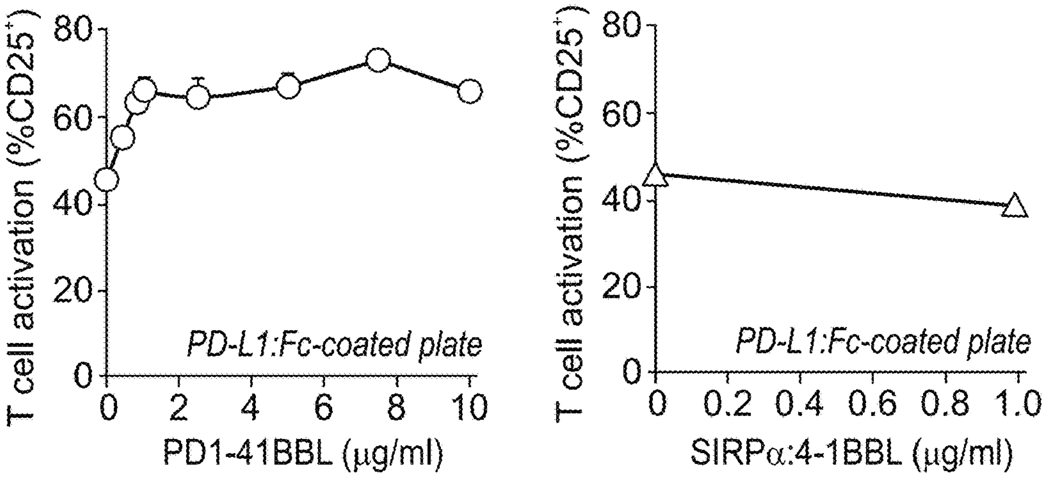
FIG. 10 demonstrates that His-tagged PD1-41BBL protein (SEQ ID NO: 5) activates freshly isolated human T cells on PDL1-Fc coated plates in the presence of sub-optimal concentrations of anti-CD3/anti-CD28 activation beads, while SIRPα:41BBL (SEQ ID NO: 6) does not induce activation. T cell activation was measured by evaluating CD25 expression by flow cytometry after 7 days of treatment.

Next, the potential induction of T cell activation by the 41BBL domain of the His-tagged PD1-41BBL protein (SEQ ID NO: 5) was evaluated. To this end, freshly isolated T cells were added to PDL1-Fc coated plates and activated with sub-optimal concentrations of anti-CD3/anti-CD28 activation beads for 7 days. Following treatment, a clear increase in the percentage of activated CD25-positive T cells was detected in the His-tagged PD1-41BBL protein (SEQ ID NO: 5) treated cells (FIG. 10), with an optimum induction at ~7.5 μg/ml. In contrast, control fusion protein SIRPα: 41BBL (SEQ ID NO: 6) did not trigger T cell activation (FIG. 10). Thus, binding of His-tagged PD1-41BBL protein (SEQ ID NO: 5) to PDL1 enables 41BBL/41BB-mediated co-stimulation and activation of T cells.

Taken together, the data provides clear evidence that upon PDL1-mediated binding, His-tagged PD1-41BBL protein (SEQ ID NO: 5) gains 41BBL-mediated co-stimulatory activity that can augment T cell activation.

Experiment 3B—PD1-41BBL Protein Augments Human PBMCs Activation

Materials—His-tagged PD1-41BBL protein (SEQ ID NO: 5) produced as described in Experiment 1A hereinabove, INF-γ ELISA Kit [cat #900-TM27, cat #900-T00—Elisa Buffer Kit (TMB)], RPMI (cat #01-100-1A, Biological industries), FBS (cat #12657-029, Gibco), L-Glutamine (cat #25030-24, Gibco), Pen/Strep (cat #15140-122, Gibco), Leaf purified anti-human CD3 (cat #BLG-317315, BioLegend), recombinant human IL2 (cat #202-IL-500, R&D Systems), human Peripheral Blood Mononuclear Cells (PBMCs), isolated from healthy donor peripheral blood by Ficoll-Paque (cat #17-1440-03, GE Healthcare), LivMet mouse pancreas cancer cells (Partecke et al, 2011).

Methods—Human PBMCs were isolated from healthy donor peripheral blood using Ficoll-Paque (Grienvic et al. 2016). Following, PBMCs were cultured for 40 hours with addition of different concentrations of His-tagged PD1-41BBL protein (SEQ ID NO: 5), in the presence of anti-CD3 (30 ng/ml) or anti-CD3 plus IL2 (1000 U/ml). The experiment was effected with or without co-culture with PDL1-expressing murine Livmet cells (E:T ratio 1:1). INF-γ concentration in the cells supernatant was evaluated by INF-γ ELISA kit according to the manufacturer's protocol.

Results—Human PBMCs, including NK cells, NKT cells, CD4+ and CD8+ effector Th1 cells, are known to secrete pro-inflammatory Interferon-γ (INF-γ) in response to activation. The activation of a T-cell requires two signals: ligation of the T-Cell Receptor (TCR) with the Major Histocompatibility Complex (MHC)/peptide complex on the Antigen Presenting Cell (APC) and cross-linking of co-stimulatory receptors on the T-cell with the corresponding ligands on the APC. 41BB, is a T-cell costimulatory receptor induced by ligation of 41BBL. 41BB transmits a potent costimulatory signal to both CD8+ and CD4+ T cells, promoting their expansion, survival, differentiation, and cytokine expression. 41BB ligand, 41BBL, is a membrane protein, which provides a co-stimulatory signal to T-cells.

In this experiment the functionality of PD1-41BBL molecule in enhancing human PBMCs activation was evaluated.

Figure 11A:
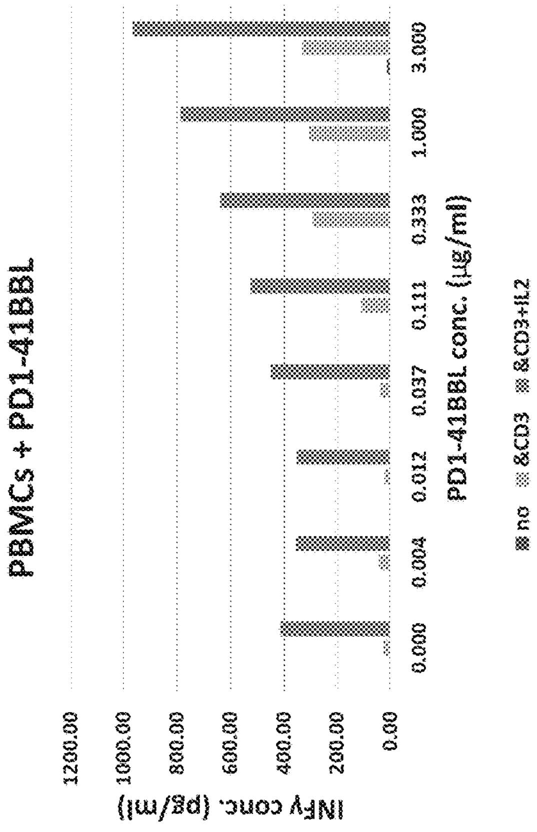
FIGS. 11A-11B demonstrate that His-tagged PD1-41BBL protein (SEQ ID NO: 5) promotes INF-γ secretion from anti-CD3 primed human PBMCs.

Addition of His-tagged PD1-41BBL protein (SEQ ID NO: 5), enhanced the activation of PBMCs in a dose depended manner, as can be seen by an increase in INF-γ secretion by PBMCs that were stimulated by anti-CD3 antibody, with or without the addition of IL2 (FIG. 11A).

Figure 11B:
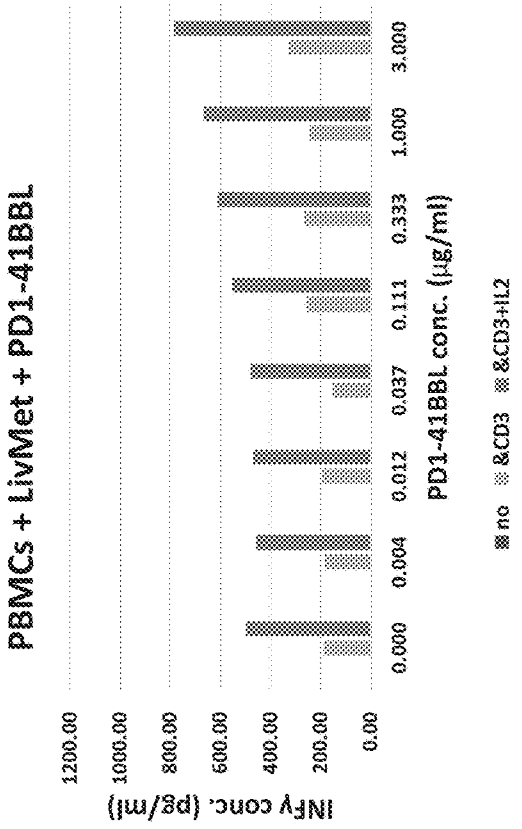

Co-culturing PBMCs with LivMet cells results in secretion of INF-γ, probably due to direct activation effect of the PBMCs by the tumor cells. Treatment with His-tagged PD1-41BBL protein (SEQ ID NO: 5) had a moderate effect when added to the co-culture; and show a more pronounced effect when added together with IL2 (FIG. 11B).

Taken together, His-tagged PD1-41BBL protein (SEQ ID NO: 5), augments activation of PBMCs, as can be seen by IFN-7 secretion.

Experiment 4—In-Vivo Proof of Concept

The effects of PD1-41BBL, both on the targeting and the activation of T, NK and B cells are tested in-vivo in mouse models. The mouse His-PD1-41BBL fusion protein is produced and purified as tagged protein in the same way as the human molecule. Mouse tumor models are generated by injecting mice with mouse cancer cells that are known to form tumors that express mouse PDL1. Mice are treated with the mouse His-tagged PD1-41BBL fusion protein molecule or the human His-tagged-PD1-41BBL fusion protein molecule. Tumor size, mice survival and inflammatory reaction in the tumor site are monitored.

Similar experiments can be performed in a humanized mouse model using human tumors. This model is constructed using mice that are lacking any mouse immune system (Nude/SCID/NSGmice). A human-like immune system is established in these mice by injection of only human T cells, PBMCs or by using genetically engineered mice that possess a fully humanized immune system. The mice are inoculated with human cancer cells and treated with the human His-tagged-PD1-41BBL molecule. Tumor size, mice survival and inflammatory reaction in the tumor site are monitored in this model as well.

The in-vivo efficacy of His-tagged-PD1-41BBL can be compared to that of its parts, namely, recombinant PD1 or 41BBL alone or in combination.

Experiment 4A—PD1-41BBL Protein Inhibits Tumor Growth in Mice Inoculated with Syngeneic Colon Carcinoma Materials—Mice autoclaved food and bedding (Ssniff, Soest, Germany), Female Balb/C mice (Janvier, Saint Berthevin Cedex, France), CT-26 mouse colon carcinoma cell line (ATCC-CRL-2638), His-tagged PD1-41BBL protein (SEQ ID NO: 5) produced as described in Experiment 1A hereinabove, PBS.

Figure 12A:
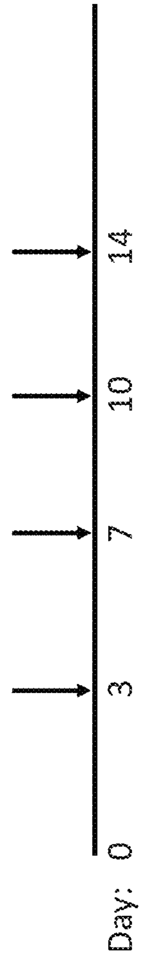
FIGS. 12A-12C demonstrate that treatment of CT-26 inoculated mice with His-tagged PD1-41BBL protein (SEQ ID NO: 5) significantly reduces tumor volume.

Methods—Mice were maintained in individually ventilated cages in groups of four mice per cage. The mice received autoclaved food and bedding and acidified (pH 4.0) tap water ad libitum. The animal facility was equipped with an automatic 12 hours light/dark regulation, temperature regulation at 22±2° C., and relative humidity of 50±10%. Female Balb/C mice were inoculated subcutaneously with $1\times10^6$ CT-26 cells and treatment started three days later. Following random assignment, 10 animals per group were administered twice weekly with four intravenous injections of His-tagged PD1-41BBL protein (SEQ ID NO: 5) (100 μg/injection) or its soluble buffer (PBS)(FIG. 12A). All administrations were performed in the morning, without anesthesia. Tumor volume was determined three times per week using caliper measurements, and the individual volumes were calculated by the formula: V=([width]2×length)/2. All animal experiments were done in accordance with the United Kingdom Coordinating Committee on Cancer Research regulations for the Welfare of Animals (Workman et al., Committee of the National Cancer Research Institute. Guidelines for the welfare of animals in cancer research. Br J Cancer 2010; 102:1555-77) and of the German Animal Protection Law and approved by the local responsible authorities (Gen0030/15).

Figure 12B:
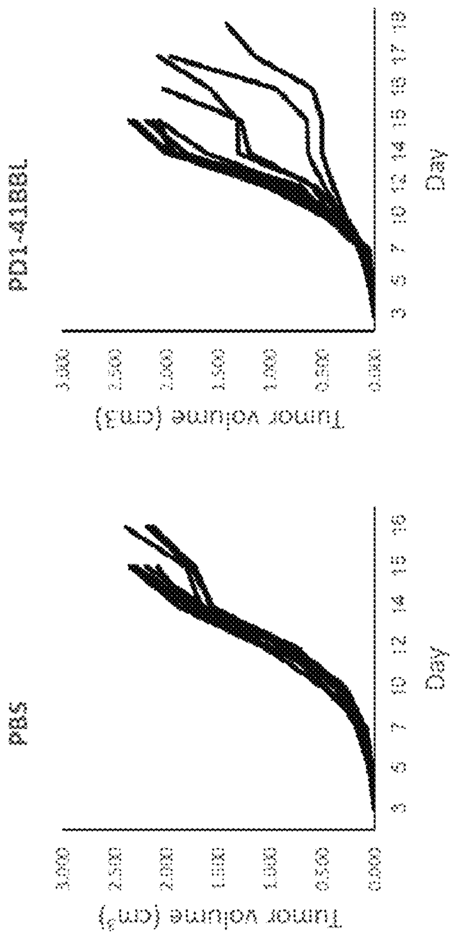
Figure 12C:
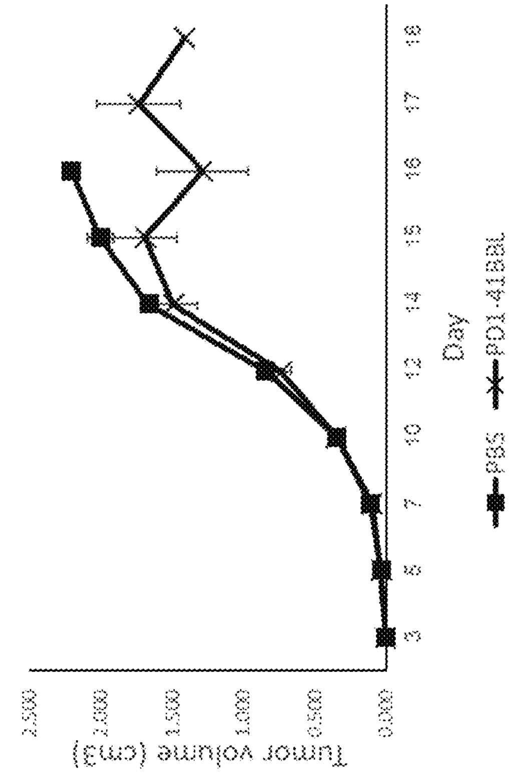

Results—In this Experiment, the in-vivo effect of PD1-41BBL was evaluated using the CT-26 mouse colon cancer model. Treatment of CT-26 inoculated mice with His-tagged PD1-41BBL protein (SEQ ID NO: 5) significantly reduced tumor volume (by about 42% at max) (FIGS. 12B-12C).

Experiment 4B—PD1-41BBL Protein is Effective for the Treatment of Mice Inoculated with a Syngeneic Leukemic Tumor Materials—Mice autoclaved food and bedding (Ssniff, Soest, Germany), Female DBA/2 mice (Janvier, Saint Berthevin Cedex, France), P388 Leukaemia cell line (Max-Delbrueck-Center for Molecular Medicine, Berlin, Germany), Anti-mouse PD-1 antibody (BioXcell, West Lebanon, USA), His-tagged PD1-41BBL protein (SEQ ID NO: 5) produced as described in Experiment 1A hereinabove, PBS.

Figure 13A:
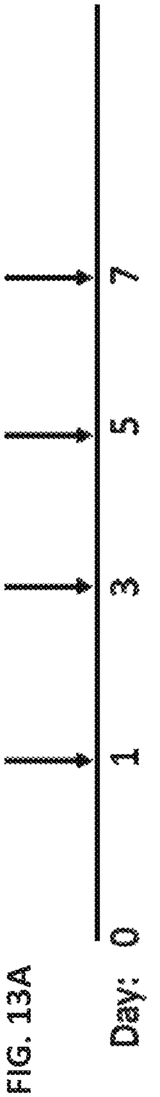
FIGS. 13A-13B demonstrate that His-tagged PD1-41BBL protein (SEQ ID NO: 5) is effective for the treatment of mice inoculated with P388 syngeneic leukemia tumor.

Methods—Mice were maintained in individually ventilated cages in groups of four mice per cage. The mice received autoclaved food and bedding and acidified (pH 4.0) tap water ad libitum. The animal facility was equipped with an automatic 12 hours light/dark regulation, temperature regulation at 22±2° C. and relative humidity of 50±10%. Female DBA/2 mice were inoculated intraperitoneally with $1\times10^6$ P388 cells and treatment started the day after. Following random assignment, 10 mice per group were administered every second day with four intravenous injections of His-tagged PD1-41BBL protein (SEQ ID NO: 5) (100 μg/injection) or its soluble buffer (PBS). 5 mg/kg anti-mouse PD-1 at the same schedule were included as a therapeutic reference (FIG. 13A). All administrations were performed in the morning, without anesthesia. Mice bearing P388 were weighed daily and once the mice became moribund, they were sacrificed; and the ascites volume was determined. Furthermore, spleens and liver from each mouse was taken and weighed.

All animal experiments were done in accordance with the United Kingdom Coordinating committee on Cancer Research regulations for the Welfare of Animals (Workman et al., committee of the National Cancer Research Institute. Guidelines for the welfare of animals in cancer research. Br J Cancer 2010; 102:1555-77) and of the German Animal Protection Law and approved by the local responsible authorities (Gen0030/1

Figure 13B:
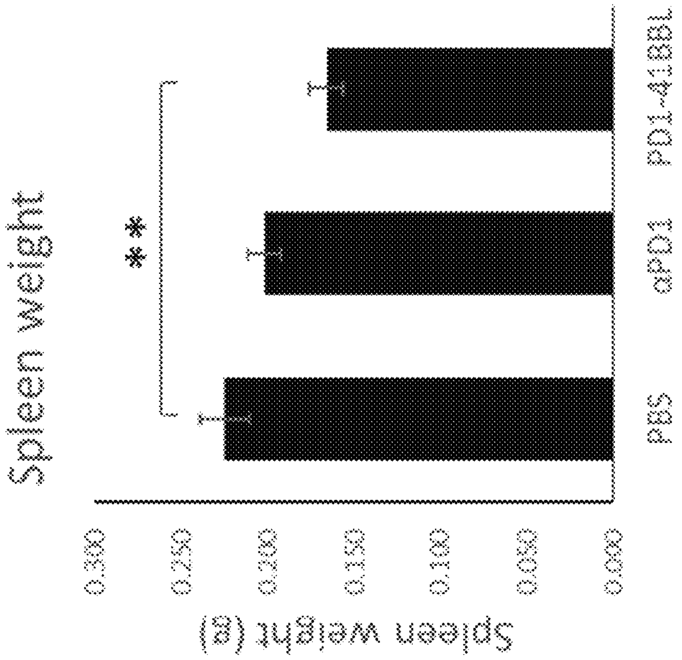

Results—In this experiment, the in-vivo effect of His-tagged PD1-41BBL protein (SEQ ID NO: 5) was evaluated using the P388 ascites mouse leukemia model. In this model, spleen weight is a marker for disease severity, due to the fact that the spleen serves as draining lymph node for the ascites. Treatment of P388 mouse leukemia inoculated mice with His-tagged PD1-41BBL protein (SEQ ID NO: 5) was effective as can be seen by significant reduction in spleen weight (27% mean, P-value=0.003) (FIG. 13B). No differences in liver weight were detected (data not shown).

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating cancer in a subject in need thereof, the method comprising administering to the subject an anti-cancer antibody and a PD1-41BBL fusion protein comprising a PD1 amino acid sequence capable of binding PD-L1 and a 4-1BBL amino acid sequence capable of binding 4-1BB, wherein said PD1 amino acid sequence is as set forth in SEQ ID NO: 2 or at least 123 amino acids in length fragment thereof, and wherein said fusion protein is characterized by a single amino acid linker between said PD1 amino acid sequence and said 4-1BBL amino acid sequence.

2. The method claim 1, wherein said linker is glycine.

3. The method of claim 1, wherein said PD1 amino acid sequence consists of SEQ ID NO: 2.

4. The method of claim 1, wherein said fusion protein is capable of at least one of:

(i) binding PD-L1 and 41BB;

(ii) activating said 41BB signaling pathway in a cell expressing said 41BB; and (iii) co-stimulating immune cells expressing said 41BB.

5. The method of claim 1, wherein said antibody is selected from the group consisting of rituximab and cetuximab.

6. The method of claim 1, wherein said cancer is selected from the group consisting of lymphoma, leukemia, colon cancer, pancreatic cancer, ovarian cancer, lung cancer and squamous cell carcinoma.

7. The method of claim 1, wherein cells of said cancer express PD-L1.

* * * * *